US008026084B2

(12) United States Patent
Ecker et al.

(10) Patent No.: US 8,026,084 B2
(45) Date of Patent: Sep. 27, 2011

(54) METHODS FOR RAPID IDENTIFICATION AND QUANTITATION OF NUCLEIC ACID VARIANTS

(75) Inventors: David J. Ecker, Encinitas, CA (US); Steven A. Hofstadler, Vista, CA (US); Thomas A. Hall, Oceanside, CA (US); Kristin Sannes Lowery, Vista, CA (US)

(73) Assignee: Ibis Biosciences, Inc., Carlsbad, CA (US)

( * ) Notice: Subject to any disclaimer, the term of this patent is extended or adjusted under 35 U.S.C. 154(b) by 756 days.

(21) Appl. No.: 11/491,376

(22) Filed: Jul. 21, 2006

(65) Prior Publication Data

US 2007/0218467 A1 Sep. 20, 2007

Related U.S. Application Data

(60) Provisional application No. 60/701,404, filed on Jul. 21, 2005, provisional application No. 60/771,101, filed on Feb. 6, 2006, provisional application No. 60/747,607, filed on May 18, 2006.

(51) Int. Cl.
*C12P 19/34* (2006.01)

(52) U.S. Cl. ........................................................ 435/91.2

(58) Field of Classification Search ........................ 435/6
See application file for complete search history.

(56) References Cited

U.S. PATENT DOCUMENTS 4,075,475 A 2/1978 Risby et al.
4,683,195 A 7/1987 Mullis et al.
4,683,202 A 7/1987 Mullis
4,965,188 A 10/1990 Mullis et al.
5,015,845 A 5/1991 Allen et al.
5,072,115 A 12/1991 Zhou
5,143,905 A 9/1992 Sivasubramanian et al.
5,213,961 A 5/1993 Bunn et al.
5,219,727 A 6/1993 Wang et al.
5,288,611 A 2/1994 Kohne
5,436,129 A 7/1995 Stapleton
5,451,500 A 9/1995 Stapleton
5,472,843 A 12/1995 Milliman
5,476,774 A 12/1995 Wang et al.
5,484,808 A 1/1996 Grinnell
5,484,908 A 1/1996 Froehler et al.
5,502,177 A 3/1996 Matteucci et al.
5,503,980 A 4/1996 Cantor
5,504,327 A 4/1996 Sproch et al.
5,504,329 A 4/1996 Mann et al.
5,523,217 A 6/1996 Lupski et al.
5,527,669 A 6/1996 Resnick et al.
5,527,675 A 6/1996 Coull et al.
5,527,875 A 6/1996 Yokoyama et al.
5,547,835 A 8/1996 Koster
5,567,587 A 10/1996 Kohne
5,576,204 A 11/1996 Blanco et al.
5,580,733 A 12/1996 Levis et al.
5,605,798 A 2/1997 Koster
5,608,217 A 3/1997 Franzen et al.
5,612,179 A 3/1997 Simons
5,622,824 A 4/1997 Koster
5,625,184 A 4/1997 Vestal et al.
5,639,606 A 6/1997 Willey
5,641,632 A 6/1997 Kohne
5,645,985 A 7/1997 Froehler et al.
5,683,869 A 11/1997 Shaw et al.
5,686,242 A 11/1997 Bruice et al.
5,691,141 A 11/1997 Koster
5,700,642 A 12/1997 Monforte et al.
5,702,895 A 12/1997 Matsunaga et al.
5,707,802 A 1/1998 Sandhu et al.
5,712,125 A 1/1998 Uhlen
5,716,825 A 2/1998 Hancock et al.
5,727,202 A 3/1998 Kucala
5,745,751 A 4/1998 Nelson et al.
5,747,246 A 5/1998 Pannetier et al.
5,747,251 A 5/1998 Carson et al.
5,753,467 A 5/1998 Jensen et al.
5,753,489 A 5/1998 Kistner et al.
5,759,771 A 6/1998 Tilanus
5,763,169 A 6/1998 Sandhu et al.
5,763,588 A 6/1998 Matteucci et al.
5,770,367 A 6/1998 Southern et al.
5,777,324 A 7/1998 Hillenkamp
5,814,442 A 9/1998 Natarajan et al.

(Continued)

FOREIGN PATENT DOCUMENTS

CN 1202204 9/1996

(Continued)

OTHER PUBLICATIONS

Hall et al. Analytical Biochemistry, vol. 344, pp. 53-69, available online Jun. 17, 2005.*
U.S. Appl. No. 09/798,007, Ibis Biosciences.
U.S. Appl. No. 10/156,608, Ibis Biosciences.
U.S. Appl. No. 10/318,463, Ibis Biosciences.
U.S. Appl. No. 10/318,881, Ibis Biosciences.
U.S. Appl. No. 10/319,290, Ibis Biosciences.
U.S. Appl. No. 10/319,342, Ibis Biosciences.
U.S. Appl. No. 10/326,047, Ibis Biosciences.
U.S. Appl. No. 10/435,307, Ibis Biosciences.
U.S. Appl. No. 10/430,253, Ibis Biosciences.
U.S. Appl. No. 10/660,122, Ibis Biosciences.
U.S. Appl. No. 10/660,996, Ibis Biosciences.
U.S. Appl. No. 10/660,997, Ibis Biosciences.
U.S. Appl. No. 10/660,998, Ibis Biosciences.
U.S. Appl. No. 11/233,630, Ibis Biosciences.
U.S. Appl. No. 11/331,978, Ibis Biosciences.
U.S. Appl. No. 11/331,987, Ibis Biosciences.
Aaserud et al., "Accurate base composition of double-strand DNA by mass spectrometry" *J. Am. Soc. Spec*. (1996) 7:1266-1269.

(Continued)

*Primary Examiner* — Gary Benzion
*Assistant Examiner* — Cynthia B Wilder
(74) *Attorney, Agent, or Firm* — Casimir Jones S.C.; Christopher C. Sappenfield

(57) ABSTRACT

There is a need for nucleic acid analysis which is both specific and rapid, and in which no nucleic acid sequencing is required. The present invention addresses this need, among others by providing a method of nucleic acid amplification of overlapping sub-segments of a nucleic acid followed by molecular mass measurement of resulting amplification products by mass spectrometry, and determination of the base compositions of the amplification products.

34 Claims, 4 Drawing Sheets

U.S. PATENT DOCUMENTS

| | | | |
|---|---|---|---|
| 5,822,824 | A | 10/1998 | Dion |
| 5,828,062 | A | 10/1998 | Jarrell et al. |
| 5,830,653 | A | 11/1998 | Froehler et al. |
| 5,830,655 | A | 11/1998 | Monforte et al. |
| 5,830,853 | A | 11/1998 | Backstrom et al. |
| 5,832,489 | A | 11/1998 | Kucala |
| 5,834,255 | A | 11/1998 | Van Gemen et al. |
| 5,845,174 | A | 12/1998 | Yasui et al. |
| 5,849,492 | A | 12/1998 | Rogan |
| 5,849,497 | A | 12/1998 | Steinman |
| 5,849,901 | A | 12/1998 | Mabilat et al. |
| 5,851,765 | A | 12/1998 | Koster |
| 5,856,174 | A | 1/1999 | Lipshutz et al. |
| 5,864,137 | A | 1/1999 | Becker et al. |
| 5,866,429 | A | 2/1999 | Bloch |
| 5,869,242 | A | 2/1999 | Kamb |
| 5,871,697 | A | 2/1999 | Rothberg et al. |
| 5,872,003 | A | 2/1999 | Koster |
| 5,876,936 | A | 3/1999 | Ju |
| 5,876,938 | A | 3/1999 | Stolowitz et al. |
| 5,885,775 | A | 3/1999 | Haff et al. |
| 5,900,481 | A | 5/1999 | Lough et al. |
| 5,928,905 | A | 7/1999 | Stemmer et al. |
| 5,928,906 | A | 7/1999 | Koster |
| 5,965,363 | A | 10/1999 | Monforte et al. |
| 5,965,383 | A | 10/1999 | Vogel et al. |
| 5,972,693 | A | 10/1999 | Rothberg et al. |
| 5,976,798 | A | 11/1999 | Parker et al. |
| 5,981,176 | A | 11/1999 | Wallace |
| 5,981,178 | A | 11/1999 | Tsui et al. |
| 5,981,190 | A | 11/1999 | Israel |
| 5,994,066 | A | 11/1999 | Bergeron et al. |
| 6,001,564 | A | 12/1999 | Bergeron et al. |
| 6,001,584 | A | 12/1999 | Karin et al. |
| 6,005,096 | A | 12/1999 | Matteucci et al. |
| 6,007,690 | A | 12/1999 | Nelson et al. |
| 6,007,992 | A | 12/1999 | Lin et al. |
| 6,015,666 | A | 1/2000 | Springer et al. |
| 6,018,713 | A | 1/2000 | Coli et al. |
| 6,024,925 | A | 2/2000 | Little et al. |
| 6,028,183 | A | 2/2000 | Lin et al. |
| 6,043,031 | A | 3/2000 | Koster et al. |
| 6,046,005 | A | 4/2000 | Ju |
| 6,051,378 | A | 4/2000 | Monforte et al. |
| 6,054,278 | A | 4/2000 | Dodge et al. |
| 6,055,487 | A | 4/2000 | Margery et al. |
| 6,060,246 | A | 5/2000 | Summerton et al. |
| 6,061,686 | A | 5/2000 | Gauvin et al. |
| 6,063,031 | A | 5/2000 | Cundari et al. |
| 6,074,823 | A | 6/2000 | Koster |
| 6,074,831 | A | 6/2000 | Yakhini et al. |
| 6,090,558 | A | 7/2000 | Butler et al. |
| 6,104,028 | A | 8/2000 | Hunter et al. |
| 6,110,710 | A | 8/2000 | Smith et al. |
| 6,111,251 | A | 8/2000 | Hillenkamp |
| 6,133,436 | A | 10/2000 | Koster et al. |
| 6,140,053 | A | 10/2000 | Koster |
| 6,146,144 | A | 11/2000 | Fowler et al. |
| 6,146,854 | A | 11/2000 | Koster et al. |
| 6,153,389 | A | 11/2000 | Haarer et al. |
| 6,159,681 | A | 12/2000 | Zebala |
| 6,180,339 | B1 | 1/2001 | Sandhu et al. |
| 6,180,372 | B1 | 1/2001 | Franzen |
| 6,187,842 | B1 | 2/2001 | Kobayashi et al. |
| 6,194,144 | B1 | 2/2001 | Koster |
| 6,197,498 | B1 | 3/2001 | Koster |
| 6,214,555 | B1 | 4/2001 | Leushner et al. |
| 6,218,118 | B1 | 4/2001 | Sampson et al. |
| 6,221,587 | B1 | 4/2001 | Ecker et al. |
| 6,221,598 | B1 | 4/2001 | Schumm et al. |
| 6,221,601 | B1 | 4/2001 | Koster et al. |
| 6,221,605 | B1 | 4/2001 | Koster |
| 6,225,450 | B1 | 5/2001 | Koster |
| 6,235,476 | B1 | 5/2001 | Bergmann et al. |
| 6,235,478 | B1 | 5/2001 | Koster |
| 6,235,480 | B1 | 5/2001 | Shultz et al. |
| 6,238,871 | B1 | 5/2001 | Koster |
| 6,238,927 | B1 | 5/2001 | Abrams et al. |
| 6,239,159 | B1 | 5/2001 | Brown et al. |
| 6,258,538 | B1 | 7/2001 | Koter et al. |
| 6,261,769 | B1 | 7/2001 | Everett et al. |
| 6,265,716 | B1 | 7/2001 | Hunter et al. |
| 6,265,718 | B1 | 7/2001 | Park et al. |
| 6,266,131 | B1 | 7/2001 | Hamada et al. |
| 6,266,144 | B1 | 7/2001 | Li |
| 6,268,129 | B1 | 7/2001 | Gut et al. |
| 6,268,131 | B1 | 7/2001 | Kang et al. |
| 6,268,144 | B1 | 7/2001 | Koster |
| 6,268,146 | B1 | 7/2001 | Shultz |
| 6,270,973 | B1 | 8/2001 | Lewis et al. |
| 6,270,974 | B1 | 8/2001 | Shultz et al. |
| 6,274,726 | B1 | 8/2001 | Laugharn, Jr. et al. |
| 6,277,573 | B1 | 8/2001 | Koster et al. |
| 6,277,578 | B1 | 8/2001 | Shultz et al. |
| 6,277,634 | B1 | 8/2001 | McCall et al. |
| 6,300,076 | B1 | 10/2001 | Koster |
| 6,303,297 | B1 | 10/2001 | Lincoln et al. |
| 6,312,893 | B1 | 11/2001 | Van Ness et al. |
| 6,312,902 | B1 | 11/2001 | Shultz et al. |
| 6,322,970 | B1 | 11/2001 | Little et al. |
| 6,361,940 | B1 | 3/2002 | Van Ness et al. |
| 6,372,424 | B1 | 4/2002 | Brow et al. |
| 6,389,428 | B1 | 5/2002 | Rigault et al. |
| 6,391,551 | B1 | 5/2002 | Shultz et al. |
| 6,393,367 | B1 | 5/2002 | Tang et al. |
| 6,419,932 | B1 | 7/2002 | Dale |
| 6,423,966 | B2 | 7/2002 | Hillenkamp et al. |
| 6,428,955 | B1 | 8/2002 | Koster et al. |
| 6,428,956 | B1 | 8/2002 | Crooke et al. |
| 6,432,651 | B1 | 8/2002 | Hughes et al. |
| 6,436,635 | B1 | 8/2002 | Fu et al. |
| 6,436,640 | B1 | 8/2002 | Simmons et al. |
| 6,453,244 | B1 | 9/2002 | Oefner et al. |
| 6,458,533 | B1 | 10/2002 | Felder et al. |
| 6,468,743 | B1 | 10/2002 | Romick et al. |
| 6,468,748 | B1 | 10/2002 | Monforte et al. |
| 6,475,143 | B2 | 11/2002 | Iliff |
| 6,475,736 | B1 | 11/2002 | Stanton, Jr. |
| 6,475,738 | B2 | 11/2002 | Shuber et al. |
| 6,479,239 | B1 | 11/2002 | Anderson et al. |
| 6,500,621 | B2 | 12/2002 | Koster |
| 6,553,317 | B1 | 4/2003 | Lincoln et al. |
| 6,558,902 | B1 | 5/2003 | Hillenkamp |
| 6,563,025 | B1 | 5/2003 | Song et al. |
| 6,566,055 | B1 | 5/2003 | Monforte et al. |
| 6,568,055 | B1 | 5/2003 | Tang et al. |
| 6,582,916 | B1 | 6/2003 | Schmidt et al. |
| 6,586,584 | B2 | 7/2003 | McMillian et al. |
| 6,589,485 | B2 | 7/2003 | Koster |
| 6,602,662 | B1 | 8/2003 | Koster et al. |
| 6,605,433 | B1 | 8/2003 | Fliss et al. |
| 6,610,492 | B1 | 8/2003 | Stanton, Jr. et al. |
| 6,613,509 | B1 | 9/2003 | Chen |
| 6,613,520 | B2 | 9/2003 | Ashby |
| 6,623,928 | B2 | 9/2003 | Van Ness et al. |
| 6,638,714 | B1 | 10/2003 | Linnen et al. |
| 6,680,476 | B1 | 1/2004 | Hidalgo et al. |
| 6,682,889 | B1 | 1/2004 | Wang et al. |
| 6,705,530 | B2 | 3/2004 | Kiekhaefer |
| 6,706,530 | B2 | 3/2004 | Hillenkamp |
| 6,716,634 | B1 | 4/2004 | Myerson |
| 6,783,939 | B2 | 8/2004 | Olmsted et al. |
| 6,800,289 | B2 | 10/2004 | Nagata et al. |
| 6,813,615 | B1 | 11/2004 | Colasanti et al. |
| 6,836,742 | B2 | 12/2004 | Brekenfeld |
| 6,852,487 | B1 | 2/2005 | Barany et al. |
| 6,856,914 | B1 | 2/2005 | Pelech |
| 6,875,593 | B2 | 4/2005 | Froehler |
| 6,906,316 | B2 | 6/2005 | Sugiyama et al. |
| 6,906,319 | B2 | 6/2005 | Hoyes |
| 6,914,137 | B2 | 7/2005 | Baker |
| 6,977,148 | B2 | 12/2005 | Dean et al. |
| 6,994,962 | B1 | 2/2006 | Thilly |
| 7,022,835 | B1 | 4/2006 | Rauth et al. |
| 7,024,370 | B2 | 4/2006 | Epler et al. |
| 7,108,974 | B2 | 9/2006 | Ecker et al. |
| 7,198,893 | B1 | 4/2007 | Köster et al. |

7,217,510 B2 5/2007 Ecker et al.
7,226,739 B2 6/2007 Ecker et al.
7,255,992 B2 8/2007 Ecker et al.
7,285,422 B1 10/2007 Little et al.
7,312,036 B2 12/2007 Sampath et al.
7,321,828 B2 1/2008 Cowsert et al.
7,349,808 B1 3/2008 Kreiswirth et al.
7,390,458 B2 6/2008 Burow et al.
7,419,787 B2 9/2008 Köster
7,501,251 B2 3/2009 Köster et al.
7,666,588 B2 2/2010 Ecker et al.
7,718,354 B2 5/2010 Ecker et al.
7,741,036 B2 6/2010 Ecker et al.
7,781,162 B2 8/2010 Ecker et al.
2001/0039263 A1 11/2001 Matthes et al.
2002/0006611 A1 1/2002 Portugal et al.
2002/0028923 A1 3/2002 Cowsert et al.
2002/0042112 A1 4/2002 Koster et al.
2002/0042506 A1 4/2002 Kristyanne et al.
2002/0045178 A1 4/2002 Cantor et al.
2002/0055101 A1 5/2002 Bergeron et al.
2002/0090320 A1 7/2002 Burow et al.
2002/0120408 A1 8/2002 Kreiswirth et al.
2002/0137057 A1 9/2002 Wold et al.
2002/0138210 A1 9/2002 Wilkes et al.
2002/0150903 A1 10/2002 Koster et al.
2002/0150927 A1 10/2002 Matray et al.
2002/0168630 A1 11/2002 Fleming et al.
2002/0187490 A1 12/2002 Tiedje et al.
2003/0017487 A1 1/2003 Xue et al.
2003/0027135 A1 2/2003 Ecker et al.
2003/0039976 A1 2/2003 Haff et al.
2003/0050470 A1 3/2003 An et al.
2003/0064483 A1 4/2003 Shaw et al.
2003/0073112 A1 4/2003 Zhang et al.
2003/0082539 A1 5/2003 Ecker et al.
2003/0084483 A1 5/2003 Simpson et al.
2003/0101172 A1 5/2003 De La Huerga
2003/0104410 A1 6/2003 Mittmann
2003/0104699 A1 6/2003 Minamihaba et al.
2003/0113738 A1 6/2003 Liu et al.
2003/0113745 A1 6/2003 Monforte et al.
2003/0119018 A1 6/2003 Omura et al.
2003/0124556 A1 7/2003 Ecker et al.
2003/0125192 A1 7/2003 Moon
2003/0129589 A1 7/2003 Koster et al.
2003/0134312 A1 7/2003 Burgyone et al.
2003/0148281 A1 8/2003 Glucksmann
2003/0148284 A1 8/2003 Vision et al.
2003/0167133 A1 9/2003 Ecker et al.
2003/0167134 A1 9/2003 Ecker et al.
2003/0175695 A1 9/2003 Ecker et al.
2003/0175696 A1 9/2003 Ecker et al.
2003/0175697 A1 9/2003 Ecker et al.
2003/0175729 A1 9/2003 Van Eijk et al.
2003/0186247 A1 10/2003 Smarason
2003/0187588 A1 10/2003 Ecker et al.
2003/0187593 A1 10/2003 Ecker et al.
2003/0187615 A1 10/2003 Epler et al.
2003/0190605 A1 10/2003 Ecker et al.
2003/0190635 A1 10/2003 McSwiggen
2003/0194699 A1 10/2003 Lewis et al.
2003/0203398 A1 10/2003 Bramucci et al.
2003/0220844 A1 11/2003 Marmellos et al.
2003/0224377 A1 12/2003 Wengel et al.
2003/0225529 A1 12/2003 Ecker et al.
2003/0228571 A1 12/2003 Ecker et al.
2003/0228597 A1 12/2003 Cowsert et al.
2003/0228613 A1 12/2003 Bornarth et al.
2004/0005555 A1 1/2004 Rothman et al.
2004/0006611 A1 1/2004 Yi
2004/0013703 A1 1/2004 Ralph et al.
2004/0014957 A1 1/2004 Eldrup et al.
2004/0023207 A1 2/2004 Polansky
2004/0023209 A1 2/2004 Jonasson
2004/0029129 A1 2/2004 Wang et al.
2004/0038206 A1 2/2004 Zhang et al.
2004/0038208 A1 2/2004 Fisher et al.
2004/0038234 A1 2/2004 Gut et al.
2004/0038385 A1 2/2004 Langlois et al.
2004/0081993 A1 4/2004 Cantor et al.
2004/0101809 A1 5/2004 Weiss et al.
2004/0110169 A1 6/2004 Ecker et al.
2004/0111221 A1 6/2004 Beattie et al.
2004/0117129 A1 6/2004 Ecker et al.
2004/0117354 A1 6/2004 Azzaro et al.
2004/0121309 A1 6/2004 Ecker et al.
2004/0121310 A1 6/2004 Ecker et al.
2004/0121311 A1 6/2004 Ecker et al.
2004/0121312 A1 6/2004 Ecker et al.
2004/0121313 A1 6/2004 Ecker et al.
2004/0121314 A1 6/2004 Ecker et al.
2004/0121315 A1 6/2004 Ecker et al.
2004/0121329 A1 6/2004 Ecker et al.
2004/0121335 A1 6/2004 Ecker et al.
2004/0121340 A1 6/2004 Ecker et al.
2004/0122598 A1 6/2004 Ecker et al.
2004/0122857 A1 6/2004 Ecker et al.
2004/0126764 A1 7/2004 Lasken et al.
2004/0137013 A1 7/2004 Katinger et al.
2004/0161770 A1 8/2004 Ecker et al.
2004/0180328 A1 9/2004 Ecker et al.
2004/0185438 A1 9/2004 Ecker
2004/0191769 A1* 9/2004 Marino et al. .................... 435/6
2004/0202997 A1 10/2004 Ecker et al.
2004/0209260 A1 10/2004 Ecker et al.
2004/0219517 A1 11/2004 Ecker et al.
2004/0253583 A1 12/2004 Ecker et al.
2004/0253619 A1 12/2004 Ecker et al.
2005/0026147 A1 2/2005 Walker et al.
2005/0026641 A1 2/2005 Hokao
2005/0027459 A1 2/2005 Ecker et al.
2005/0065813 A1 3/2005 Mishelevich et al.
2005/0130196 A1 6/2005 Hofstadler et al.
2005/0130216 A1 6/2005 Becker et al.
2005/0142584 A1 6/2005 Willson et al.
2005/0250125 A1 11/2005 Novakoff
2005/0266397 A1 12/2005 Ecker et al.
2005/0266411 A1 12/2005 Hofstadler et al.
2006/0020391 A1 1/2006 Kreiswirth et al.
2006/0057605 A1 3/2006 Sampath et al.
2006/0121520 A1 6/2006 Ecker et al.
2006/0172330 A1 8/2006 Osborn et al.
2006/0205040 A1 9/2006 Sampath
2006/0240412 A1 10/2006 Hall et al.
2006/0259249 A1* 11/2006 Sampath et al. ................ 702/20
2006/0275788 A1 12/2006 Ecker et al.
2007/0048735 A1 3/2007 Ecker et al.
2008/0160512 A1 7/2008 Ecker et al.
2008/0311558 A1 12/2008 Ecker et al.
2009/0004643 A1 1/2009 Ecker et al.
2009/0023150 A1 1/2009 Koster et al.
2009/0042203 A1 2/2009 Koster
2009/0092977 A1 4/2009 Koster
2009/0125245 A1 5/2009 Hofstadler et al.
2009/0148829 A1 6/2009 Ecker et al.
2009/0148836 A1 6/2009 Ecker et al.
2009/0148837 A1 6/2009 Ecker et al.
2009/0182511 A1 7/2009 Ecker et al.
2009/0239224 A1 9/2009 Ecker et al.
2009/0280471 A1 11/2009 Ecker et al.
2010/0070194 A1 3/2010 Ecker et al.
2010/0145626 A1 6/2010 Ecker et al.
2010/0184035 A1 7/2010 Hall et al.

FOREIGN PATENT DOCUMENTS

DE 19732086 A1 1/1999
DE 19802905 7/1999
DE 19824280 12/1999
DE 19852167 5/2000
DE 19943374 A1 3/2001
DE 10132147 B4 2/2003
EP 281390 A2 9/1988
EP 633321 A1 1/1995
EP 0620862 4/1998
EP 1035219 A1 9/2000
EP 1138782 A2 10/2001
EP 1234888 A2 8/2002

| | | | |
|---|---|---|---|
| EP | 02709785 | | 9/2002 |
| EP | 1138782 | | 2/2003 |
| EP | 1308506 | A1 | 5/2003 |
| EP | 1310571 | A2 | 5/2003 |
| EP | 1333101 | | 8/2003 |
| EP | 1364064 | A2 | 11/2003 |
| EP | 1365031 | A1 | 11/2003 |
| EP | 1234888 | | 1/2004 |
| EP | 1234888 | A3 | 1/2004 |
| EP | 1748072 | A1 | 1/2007 |
| FR | 2811321 | A1 | 1/2002 |
| GB | 2325002 | | 11/1998 |
| GB | 2339905 | | 2/2000 |
| IN | 01136/KOLNP/2003 | | 2/2003 |
| JP | 5276999 | A2 | 10/1993 |
| JP | 11137259 | A | 5/1999 |
| JP | 24024206 | A2 | 1/2004 |
| JP | 2004000200 | A2 | 1/2004 |
| JP | 24201641 | A2 | 7/2004 |
| JP | 24201679 | A2 | 7/2004 |
| WO | WO8803957 | A1 | 6/1988 |
| WO | WO9015157 | A1 | 12/1990 |
| WO | WO9205182 | A1 | 4/1992 |
| WO | WO9208117 | A1 | 5/1992 |
| WO | WO9209703 | A1 | 6/1992 |
| WO | WO9219774 | A1 | 11/1992 |
| WO | WO 93/03186 | | 2/1993 |
| WO | WO9305182 | A1 | 3/1993 |
| WO | WO 93/08297 | | 4/1993 |
| WO | WO 94/16101 | | 7/1994 |
| WO | WO 94/21822 | | 9/1994 |
| WO | WO9419490 | A1 | 9/1994 |
| WO | WO 95/04161 | | 2/1995 |
| WO | WO 95/13396 | | 5/1995 |
| WO | WO9511996 | A1 | 5/1995 |
| WO | WO9513395 | A1 | 5/1995 |
| WO | WO9531997 | A1 | 11/1995 |
| WO | WO9606187 | A1 | 2/1996 |
| WO | WO9616186 | A1 | 5/1996 |
| WO | WO 96/29431 | | 9/1996 |
| WO | WO 96/32504 | | 10/1996 |
| WO | WO 96/37630 | | 11/1996 |
| WO | WO9635450 | A1 | 11/1996 |
| WO | WO 97/33000 | | 9/1997 |
| WO | WO9734909 | A1 | 9/1997 |
| WO | WO 97/37041 | | 10/1997 |
| WO | WO9747766 | A1 | 12/1997 |
| WO | WO 98/03684 | | 1/1998 |
| WO | WO 98/12355 | | 3/1998 |
| WO | WO 98/14616 | | 4/1998 |
| WO | WO 98/15652 | | 4/1998 |
| WO | WO 98/20020 | | 5/1998 |
| WO | WO 98/20157 | | 5/1998 |
| WO | WO 98/20166 | | 5/1998 |
| WO | WO 98/26095 | | 6/1998 |
| WO | WO 98/31830 | | 7/1998 |
| WO | WO9835057 | A1 | 8/1998 |
| WO | WO 98/40520 | | 9/1998 |
| WO | WO 98/54751 | | 12/1998 |
| WO | WO9854571 | A1 | 12/1998 |
| WO | WO 99/05319 | | 2/1999 |
| WO | WO 99/12040 | | 3/1999 |
| WO | WO 99/14375 | | 3/1999 |
| WO | WO9913104 | A1 | 3/1999 |
| WO | WO 99/29898 | | 6/1999 |
| WO | WO 99/31278 | | 6/1999 |
| WO | WO 99/57318 | | 11/1999 |
| WO | WO9958713 | A2 | 11/1999 |
| WO | WO9960183 | A1 | 11/1999 |
| WO | WO0032750 | A1 | 6/2000 |
| WO | WO0038636 | A1 | 7/2000 |
| WO | WO0063362 | A1 | 10/2000 |
| WO | WO0066762 | A2 | 11/2000 |
| WO | WO0066789 | A2 | 11/2000 |
| WO | WO0077260 | A1 | 12/2000 |
| WO | WO0100828 | A2 | 1/2001 |
| WO | WO 01/07648 | | 2/2001 |
| WO | WO0112853 | A1 | 2/2001 |
| WO | WO0120018 | A2 | 3/2001 |
| WO | WO 01/23604 | | 4/2001 |
| WO | WO0123608 | A2 | 4/2001 |
| WO | WO 01/32930 | | 5/2001 |
| WO | WO0140497 | A2 | 6/2001 |
| WO | WO0146404 | A1 | 6/2001 |
| WO | WO 01/51661 | | 7/2001 |
| WO | WO0151662 | A1 | 7/2001 |
| WO | WO 01/57263 | | 8/2001 |
| WO | WO 01/57518 | | 8/2001 |
| WO | WO 01/73199 | | 10/2001 |
| WO | WO0173119 | A2 | 10/2001 |
| WO | WO0177392 | A2 | 10/2001 |
| WO | WO0196388 | A2 | 12/2001 |
| WO | WO0202811 | A2 | 1/2002 |
| WO | WO 02/10186 | | 2/2002 |
| WO | WO 02/10444 | | 2/2002 |
| WO | WO 02/18641 | | 3/2002 |
| WO | WO 02/21108 | | 3/2002 |
| WO | WO 02/22873 | | 3/2002 |
| WO | WO0224876 | A2 | 3/2002 |
| WO | WO 02/50307 | | 6/2002 |
| WO | WO 02/057491 | | 7/2002 |
| WO | WO 02/070664 | | 9/2002 |
| WO | WO02070728 | A2 | 9/2002 |
| WO | WO02070737 | A2 | 9/2002 |
| WO | WO 02/077278 | | 10/2002 |
| WO | WO 02/099034 | | 12/2002 |
| WO | WO02099095 | A2 | 12/2002 |
| WO | WO02099129 | A2 | 12/2002 |
| WO | WO02099130 | A2 | 12/2002 |
| WO | WO 03/002750 | | 1/2003 |
| WO | WO 03/008636 | | 1/2003 |
| WO | WO2003001976 | A2 | 1/2003 |
| WO | WO 03/016546 | | 2/2003 |
| WO | WO200314382 | A2 | 2/2003 |
| WO | WO2003012058 | A2 | 2/2003 |
| WO | WO2003012074 | A2 | 2/2003 |
| WO | WO2003018636 | A2 | 3/2003 |
| WO | WO2003020890 | A2 | 3/2003 |
| WO | WO200303373 | A2 | 4/2003 |
| WO | WO 03/060163 | | 7/2003 |
| WO | WO2003054162 | A2 | 7/2003 |
| WO | WO2003054755 | A2 | 7/2003 |
| WO | WO2003075955 | A1 | 9/2003 |
| WO | WO 03/088979 | | 10/2003 |
| WO | WO 03/093506 | | 11/2003 |
| WO | WO 03/097869 | | 11/2003 |
| WO | WO2003100035 | A2 | 12/2003 |
| WO | WO2003100068 | A1 | 12/2003 |
| WO | WO2003102191 | A1 | 12/2003 |
| WO | WO2003104410 | A2 | 12/2003 |
| WO | WO2003106635 | A2 | 12/2003 |
| WO | WO2004003511 | A2 | 1/2004 |
| WO | WO2004009849 | A1 | 1/2004 |
| WO | WO2004011651 | A1 | 2/2004 |
| WO | WO2004013357 | A2 | 2/2004 |
| WO | WO2004040013 | A1 | 5/2004 |
| WO | WO2004044123 | A2 | 5/2004 |
| WO | WO2004044247 | A2 | 5/2004 |
| WO | WO 2004/052175 | | 6/2004 |
| WO | WO2004052175 | A3 | 6/2004 |
| WO | WO2004053076 | A2 | 6/2004 |
| WO | WO2004053141 | A2 | 6/2004 |
| WO | WO2004053164 | A1 | 6/2004 |
| WO | WO2004060278 | A2 | 7/2004 |
| WO | WO2004070001 | A2 | 8/2004 |
| WO | WO2004072230 | A2 | 8/2004 |
| WO | WO2004072231 | A2 | 8/2004 |
| WO | WO2004101809 | A2 | 11/2004 |
| WO | WO2005003384 | A1 | 1/2005 |
| WO | WO2005009202 | A2 | 2/2005 |
| WO | WO2005012572 | A1 | 2/2005 |
| WO | WO2005024046 | A2 | 3/2005 |
| WO | WO2005036369 | A2 | 4/2005 |
| WO | WO 2005/053141 | | 6/2005 |
| WO | WO2005054454 | A1 | 6/2005 |
| WO | WO2005075686 | A1 | 8/2005 |
| WO | WO2005086634 | A2 | 9/2005 |
| WO | WO2005091971 | A2 | 10/2005 |

| | | | |
|---|---|---|---|
| WO | WO2005098047 | A2 | 10/2005 |
| WO | WO2005116263 | A2 | 12/2005 |
| WO | WO2006089762 | A1 | 8/2006 |
| WO | WO2006094238 | A2 | 9/2006 |
| WO | WO2006116127 | A2 | 11/2006 |
| WO | WO2006135400 | A2 | 12/2006 |
| WO | WO2007014045 | A2 | 2/2007 |
| WO | WO2007086904 | A2 | 8/2007 |
| WO | WO2008104002 | A2 | 8/2008 |
| WO | WO2008118809 | A1 | 10/2008 |

OTHER PUBLICATIONS

Alves-Silva, J. et al., "The Ancestry of Brazilian mtDNA Lineages," *Am. J. Hum. Genet*. (2000) 67:444-461.

Anderson et al., "Sequence and organization of the human mitochondrial genome," *Nature* (1981) 290:457-465.

Bahrmand et al., "Polymerase chain reaction of bacterial genomes with single universal primer: application to distinguishing mycobacteria species" *Molecular and Cellular Probes* (1996) 10:117-122.

Bahrmand et al., "Use of restriction enzyme analysis of amplified DNA coding for the hsp65 gene and polymerase chain reaction with universal primer for rapid differentiation of *mycobacterium* species in the clinical laboratory" *Scandinavian Journal of Infectious Diseases* (1998) 30:477-480.

Baker et al., "Review and re-analysis of domain-specific 16S primers" *J. Microbiol. Methods* (2003) 55:541-555.

Bastia et al., "Organelle DNA analysis of *Solanum* and *Brassica* somatic hybrids by PCR with 'universal primers'." *Theoretical and Applied Genetics* (2001) 102:1265-1272.

Batey et al., "Preparation of Isotopically Labeled Ribonucleotides for Multidimensional NMR Spectroscopy of RNA", NAR, 20 (17) 4515-4523, 1992.

Baumer et al., "Age-related Human mtDNA Deletions: A Heterogeneous Set of Deletions Arising at a Single Pair of Directly Repeated Sequences" *Am. J. Hum. Genet*. (1994) 54:618-630.

Benson et al., "Advantages of *Thermococcus kodakaraenis* (KOD) DNA polymerase for PCR-mass spectrometry based analyses" *J. Am. Soc. Mass Spectrom*. (2003) 14:601-604.

Black et al., "Detection of trace levels of tricothecene mycotoxins in human urine by gas chromatography-mass spectrometry" *J. Chromatog* (1986) 367:103-115.

BLAST Search results (Mar. 2006).

Boivin-Jahns et al., "Bacterial Diversity in a Deep-Subsurface Clay Environment" *Applied and Environmental Microbiology* (1996) 62:3405-3412.

Borrow et al., "SiaD PCR Elisa for confirmation and identification of serogroup Y and W135 *meningococcal* infections" *FEMS Microbiological Letters* (1998) 159:209-214.

Bowen et al., "The native virulence plasmid combination affects the segregational stability of a theta-replicating shuttle vector in *bacillus anthracis* var, New Hampshire" *J. Appl. Microbiol*. (1999) 87:270-278.

Campbell et al., "Detection of California serogroup Bunyaviruses in tissue culture and mosquito pools by PCR" *J. Virol. Methods* (1996) 57:175-179.

Carracedo et al., "DNA commission of the international society for forensic genetics: guidelines for mitochondrial DNA typing" *Forensic Science International* (2000) 110:79-85.

Case et al., "Maternal inheritance of mitochondrial DNA polymorphisms in cultured human fibroblasts," *Somatic Cell Genetics* (1981) 7:103-108.

Cespedes et al., "Polymerase chain reaction restriction fragment length polymorphism analysis of a short fragment of the cytochrome b gene for identification of flatfish species" *J. Food Protection* (1998) 61:1684-1685.

Chang, P.-K. et al., "aflT, a MFS transporter-encoding gene located in the aflatoxin gene cluster, does not have a significant role in aflatoxin secretion," Fungal Genet.Biol. (2004) 41:911-920.

Chen et al., "Universal primers for amplification of mitochondrial small subunit ribosomal RNA-encoding gene in scleractinian corals" *Marine Biotechnology* (2000) 2:146-153.

Chen et al., "A universal PCR primer to detect members of the *Potyviridae* and its use to examine the taxonomic status of several members of the family" *Archives of Virology* (2001) 146:757-766.

Chen, N. et al., "The genomic sequence of ectromelia virus, the causative agent of mousepox," *Virology* (2003) 317:165-186.

Cho et al., "Application of the ribonuclease P (RNase P) RNA gene sequence for phylogenetic analysis of the gene *Saccharomonospora" International Journal of Systematic Bacteriology* (1998) 48:1223-1230.

Conrads et al., "16S-23S rDNA internal transcribed spacer sequences for analysis of the phylogenetic relationships among species of the genus *Fusobacterium" International Journal of Systematic and Evolutionary Microbiology* (2002) 52:493-499.

Cornel et al., "Polymerase chain reaction species diagnostic assay for *Anopheles quadrimaculatus* cryptic species (Diptera: Culicidae) based on ribosomal DNA ITS2 sequences" *Journal ofMedical Entomology* (1996) 33:109-116.

Crain et al., "Applications of mass spectrometry of the characterization of oligonucleotides and nucleic acids" *Curr. Opin. Biotechnol*. (1998) 9:25-34.

Crespillo et al., "Mitochondrial DNA sequences for 118 individuals from northeastern Spain" *Int. J. Legal Med*. (2000) 114:130-132.

Dasen et al., "Classification and identification of Propionibacteria based on 16S ribosomal RNA genes and PCR" *Systematic and Applied Microbiology* (1998) 21:251-259.

Deforce et al., "Analysis of oligonucleotides by ESI-MS" *Advances in Chromatography* (2000) 40:539-566.

Deforce et al., "Characterization of DNA Oligonucleotides by Coupling of Capillary Zone Electrophoresis to Electrospray Ionization Q-TOF Mass Spectrometry" *Analytical Chemistry* (1998) 70:3060-3068.

Demesure et al., "A set of universal primers for amplification of polymorphic non-coding regions of mitochondrial and chloroplast DNA in plants" *Molecular Ecology* (1995) 4:129-131.

Dias Neto et al., "Shotgun sequencing of the human transcriptome with ORF expressed sequence tags" *PNAS* (2000) 97:3491-3496.

Dinauer et al., "Sequence-based typing of HLA class II DQB1" *Tissue Anigens* (2000) 55:364-368.

Dubernet et al., "A PCR-based method for identification of *Lactobacilli* at the genus level" *FEMS Microbiology Letters* (2002) 214:271-275.

Elnifro et al., "PCR and Restriction Endonuclease Analysis for Rapid Identification of Adenovirus Subgenera" *Journal of Clinical Microbiology* (2000) 38:2055-2061.

EMBL Accession No. S90302, Human, Muscle, Mitochondrial Mutant, 22 nt, segment 2 of 2 (XP002436791) Nov. 26, 1993.

Esmans et al., "Liquid Chromatography-Mass Spectrometry in Nucleoside, nucleotide and modified nucleotide characterization" *J. of Chromatography A* (1998) 794:109-127.

European Search Report for 02709785.6 dated Oct. 10, 2005.

Figueiredo et al., "Identification of Brazilian flaviviruses by a simplified reverse transcription-polymerase chain reaction method using Flavivirus universal primers" *American Journal of Tropical Medicine and Hygiene* (1998) 59:357-362.

Flora, et al., "Dual-micro-ESI source for precise mass determination on a quadrupole time-of-flight mass spectrometer for genomic and proteomic applications" *Anal. Bioanal. Chem*. (2002) 373:538-546.

Fox et al., "Identification and Detection of Bacteria: Electrospray MS-MS Versus Derivatization/GC-MS" *Proceedings of the ERDEC Scientific Conference on Chemical and Biological Defense Research* (1994) 39-44.

Fox et al., "Identification of Brucella by Ribosomal-spacer-region PCR and differentiation of, *Brucella canis* from other *Brucella* spp. pathogenic for humans by carbohdrate profiles" *Journal of Clinical Microbiology* (1998) 36:3217-3222.

Fox et al., "Report of the 'Bioterrorism Workshop' Duke University Thomas Center on Apr. 24, 2002 organized by US Army Research Office" *Journal of Microbiological Methods* (2002) 51:247-254.

Fraser et al., "The Minimal Gene Complement of *Mycoplasma genitalium" Science* (1995) 270:397-403.

Fuerstenau et al., "Molecular Weight Determination of Megadalton DNA Electrospray Ions Using Charge Detection Time-of-flight Mass Spectrometry" *Rapid Comm. Mass Spec*. (1995) 90:4961-4972.

Fujioka et al., "Analysis of enterovirus genotypes using single-strand conformation polymorphisms of polymerase chain reaction products" *J. Virol. Meth.* (1995) 51:253-258.
Gabriel et al., "Improved mtDNA sequence analysis of forensic remains using a "mini-primer set" amplification strategy" *Journal of Forensic Sciences* (2001) 46:247-253.
Gattermann et al., "Heteroplasmic Point Mutations of Mitochondrial DNA Affecting Subunit I of Cytochrome c Oxidase in Two Patients with Acquired Idiopathic Sideroblastic Anemia" *Blood* (1997) 90:4961-4972.
Ginther et al., "Identifying individuals by sequencing mitochondrial DNA from teeth," *Nature Genetics* (1992) 2:135-138.
Giles et al., "Maternal inheritance of human mitochondrial DNA," *Proc. Natl. Acad. Sci.* (1980) 77:6715-6719.
Golden, M.R. et al., "Classification of European mtDNAs from an Analysis of Three European Populations," *Genetics* (1996) 144:1835-1850.
Goto et al., "Applications of the partial 16S rDNA sequence as an index for rapid identification of species in the genus *Bacillus" J. Gen. Appl. Microbiol.* (2000) 46:1-8.
Greenberg et al., "Intraspecific nucleotide sequence variability surrounding the origin of replication in human mitochondrial DNA," *Gene* (1983) 21:33-49.
Griffey et al., "Detection of base pair mismatches in duplex DNA and RNA oligonucleotides using electrospray mass spectrometry" *Proceedings of SPIE—The International Society for Optical Engineering* (1997) 2985:82-86.
Griffin et al., "Direct genetic analysis by matrix-assisted laser desorption/ionization mass spectrometry" *PNAS* (1999) 96:6301-6306.
Griffin et al., "Single-nucleotide polymorphism analysis by MALDI-TOF mass spectrometry" *Trends in Biotechnology* (2000) 18:77-84.
Grzybowski "Extremely high levels of human mitochondrial DNA heteroplasmy in single hair roots" *Electrophoresis* (2000) 21:548-553.
Hahner et al., "Analysis of short tandem repeat polymorphisms by electrospray ion trap mass spectrometry" *Nucleic Acids Research* (2000) 28:E82.
Hannis et al., "Accurate characterization of the tyrosine hydroxylase forensic allele 9.3 through development of electrospray ionization Fourier transform ion cyclotron resonance mass spectrometry" *Rapid Communications in Mass Spectrometry* (1999) 13:954-962.
Hannis et al., "Detection of double-stranded PCR amplicons at the attomole level electrosprayed from low nanomolar solutions using FT-ICR mass spectrometry" *Fresenius Journal of Analytical Chemistry* (2001) 369: 246-251.
Hannis et al., "Genotyping short tandem repeats using flow injection and electrospray ionization Fourier transform ion cyclotron resonance mass spectrometry" *Rapid Communications in Mass Spectrometry* (2001) 15:348-350.
Hannis et al., "Genotyping complex short tandem repeats using electrospray ionization Fourier transform ion cyclotron resonance multistage mass spectrometry" *Proceedings of SPIE—The International Society for Optical Engineering* (2000) 3926:36-47.
Haugland et al., "Identification of putative sequence specific PCR primers for detection of the toxigenic fungal species *Stachybotrys chartarum" Mol. Cell. Probes* (1998) 12:387-396.
Hayashi et al., "Phylogenetic analysis of the human gut microbiota using 16S rDNA clone libraries and strictly anaerobic culture-based methods" *Microbiology and Immunology* (2002) 46:535-548.
Henchal et al., "Sensitivity and specificity of a universal primer set for the rapid diagnosis of dengue virus infections by polymerase chain reaction and nucleic acid hybridization" *American Journal of Tropical Medicine and Hygiene* (1991) 45:418-428.
Herrmann et al., "Differentiation of Chlamydia spp. By Sequence Determination and Restriction Endonuclease Cleavage of RNase P RNA Genes" *J. Clin. Microbiol.* (1996) 34:1897-1902.
Higgins et al., "Competitive oligonucleotide single-base extension combined with mass spectrometric detection for mutation screening" *BioTechniques* (1997) 23:710-714.
Hoffman et al., "Universal primer set for the full-length amplification of all influenza A viruses" *Archives of Virology* (2001) 146:2275-2289.
Holland et al., "Mitochondrial DNA Sequence Analysis of Human Skeletal Remains: Identification of Remains from the Vietnam War," *Journal of Forensic Sciences* (1993) 38:542-553.
Holm et al., "Removing near-neighbour redundancy from large protein sequence collections" *Bioinformatics* (1998) 14:423-429.
Honda et al., "Universal method of hypersensitive nested PCR toward forensic DNA typing" *International Congress Series* (1998) 7:28-30.
Howell et al., "Persistent Heteroplasmy of a Mutation in the Human mtDNA Control Region: Hypermutation as an Apparent Consequence of Simple-Repeat Expansion/Contraction" *Am. J. Hum. Genet.* (2000) 66:1589-1598.
Hurst et al., "Detection of bacterial DNA polymerase chain reaction products by matrix-assisted laser desorption/ionization mass spectrometry" *Rapid Commun. Mass. Spec.* (1996) 10:377-382.
Hurst et al., "MALDI-TOF Analysis of Polymerase Chain Reaction Products from Methanotrophic Bacteria" *Anal. Chem.* (1998) 70:2693-2698.
Hutchison et al., "Maternal inheritance of mammalian mitochondrial DNA," *Nature* (1974) 251:536-538.
International Search Report for PCT/US02/20336 dated Feb. 3, 2003.
International Search Report for PCT/US03/38795 dated Apr. 19, 2004.
International Prelim. Exam. Report for PCT/US02/20336 dated May 12, 2004.
International Search Report for PCT/US03/38757 dated Jun. 24, 2004.
International Search Report for PCT/US03/38830 dated Aug. 25, 2004.
International Search Report for PCT/US03/38505 dated Apr. 12, 2005.
International Search Report for PCT/US03/38761 dated Dec. 30, 2005.
International Search Report for PCT/US2004/011877 dated Apr. 20, 2006.
International Search Report for PCT/US2005/000386 dated May 9, 2006.
International Search Report for PCT/US2005/018031 dated Jun. 28, 2006.
Isola et al., "MALDI-TOF mass spectrometric method for detection of hybridized DNA oligomers" *Analytical Chemistry* (2001) 73:2126-2131.
Jankowski et al., "Mass spectrometry of DNA. Part 2. Quantitative estimation of base composition" *European Journal of Mass Spectrometry in Biochemistry, Medicine, and Environmental Research* (1980) 1:45-52.
Jensen et al., "Rapid Identification of Bacteria on the Basis of Polymerase Chain Reaction-Amplified Ribosomal DNA Spacer Polymorphisms" *Appl. Environ. Microbiol.* (1993) 59:945-952.
Jensen et al., "Genotype-by-environment Interaction in Genetic Mapping of Multiple Quantitative Trait Loci" *Theor. Appl. Genet.* (1995) 91:33-37.
Jiang et al., "Multiple Trait Analysis of Genetic Mapping for Quantitative Trait Loci Genetics" *Genetics* (1995) 140:1111-1127.
Jiang et al., "A highly efficient and automated method of purifying and desalting PCR products for analysis by electrospray ionization mass spectrometry. "*Anal. Biochem.* (2003) 316:50-57.
Johnson et al., "Precise molecular weight determination of CPR products of the rRNA intergenic spacer region using electrospray quadrupole mass spectroemtry for differentiation of *B. subtilis* and *B. atrophaeus*, closely related species of *bacilli" Journal of Microbiological Methods* (2000) 40:241-254.
Jurinke et al., "Detection of hepatitis B virus DNA in serum samples via nested PCR and MALDI-TOF mass spectrometry" *Genetic Analysis: Biomolecular Engineering* (1996) 13:67-71.
Kageyama et al., "Rapid detection of human fecal *Eubacterium* species and related genera by nested PCR method" *Microbiology and Immunology* (2001) 45:315-318.
Ke et al., "Development of a PCR Assay for Rapid Detection of Enterococci" *Journal of Clinical Microbiology* (1999) 37:3497-3503.
Keller et al., "Empirical Statistical Model to Estimate the Accuracy of Peptide Identifications Made by MS/MS and Database Search" *Anal. Chem* (2002) 74:5383-5392.

Kilpatrick et al., "Group-Specific Identification of Polioviruses by PCR Using Primer Containing Mixed-Base or Deoxyinosine Residues at Positions of Codon Degeneracy" *J. Clin. Microbiol.* (1996) 34:2990-2996.
Krahmer et al., "Electrospray quadrupole mass spectrometry analysis of model oligonucleotides and polymerase chain reaction products: determination of base substitutions, nucleotide additions/deletions, and chemical modifications" *Anal. Chem.* (1999) 71:2893-2900.
Krahmer et al., "MS for identification of single nucleotide polymorphisms and MS/MS for discrimination of isomeric PCR products" *Anal. Chem.* (2000) 72:4033-4040.
Kupke et al., "Molecular Characterization of Lantibiotic-synthesizing Enzyme EpiD Reveals a Function for Bacterial Dfp Proteins i Coenzyme A Biosynthesis" *Journal of Biological Chemistry* (2000) 275:31838-31846.
Lacroix et al., "PCR-Based Technique for the Detection of Bacteria in Semen and Urine" *J. Microbiol. Meth.* (1996) 26:61-71.
Leif et al., "Isolation and characterization of the proton-translocating NADH: ubiquinone oxidoreductase from *Escherichia coli" Eur. J. Biochem.* (1995) 230:538-548.
Lewers et al., "Detection of Linked QTL for Soybean Brown Stem Rot Resistance in 'BSR 101' as Expressed in a Growth Chamber Environment" *Molecular Breeding* (1999) 5:33-42.
Li et al., "Single nucleotide polymorphism determination using primer extension and time of flight mass spectrometry" *Electrophoresis* (1999) 20:1258-1265.
Little, et al., "Rapid Sequencing of Oligonucleotides by High-Resolution Mass Spectrometry" *J. Am. Chem. Soc.* (1994) 116:4893-4897.
Little et al., "MALDI on a Chip: Analysis of Arrays of Low-Femtomole to Subfemtomole Quantities of Synthetic Oligonucleotides and DNA Diagnostic Products Dispensed by a Piezoelectric Pipet" *Analytical Chemistry* (1997) 69:4540-4546.
Liu et al., "Improving the microdialysis procedure for electrospray ionization mass spectrometry of biological samples" *Journal ofMass Spectrometry* (1997) 32:425-431.
Liu et al., "An unusual gene arrangement for the putative chromosome replication origin and circadian expression of dnaN in *Synechococcus* sp. Strain PCC 7942" *Gene* (1996) 172:105-109.
Loakes et al., "Nitroindoles as universal bases" *Nucleosides and Nucleotides* (1995) 14:1001-1003.
Love et al., "Cloning and sequence of the groESL heat-shock operon of *Pasteurella multocida" Gene* (1995) 166:179-180.
Maiwald et al., "Characterization of contaminating DNA in Taq polymerase which occurs during amplification with a primer set for Legionella 5S ribosomal RNA" *Molecular and Cellular Probes* (1994) 8:11-14.
Mangrum et al., "Solution composition and thermal denaturation for the production of single-stranded PCR amplicons: piperdine-induced destabilization of the DNA duplex?" *Journal of the American Society for Mass Spectrometry* (2002) 13:232-240.
Martemyanov et al., "Extremely Thermostable Elongation Factor G from *Aquifex aeolicus*: Cloning, Expression, Purification, and Characterization in a Heterologous Translation System" *Protein Expr. Purif.* (2000) 18:257-261.
Matray et al., "Synthesis and properties of RNA analogs—oligoribonucleotide N3'->P5' phosphoramidates" *Nucleic Acids Res* (1999) 3976-3985.
McCabe et al., "Bacterial Species Identification after DNA Amplification with a Universal Primer Pair" *Molecular Genetics and Metabolism* (1999) 66:205-211.
McLafferty et al., "Comparison of Algorithms and Databases for Matching Unknown Mass Spectra" *J. Am. Soc. Mass Spectrom.* (1998).
Meiyu et al., "Detection of flaviviruses by reverse transcriptase-polymerase chain reaction with the universal primer set" *Microbiology and Immunology* (1997) 41:209-213.
Messmer et al., "Discrimination of *Streptococcus pneumoniae* from other upper respiratory tract streptococci by arbitrarily primed PCR" *Clinical Biochemistry* (1995) 28:567-572.
Miller et al., "A compendium of human mitochondrial DNA control region: development of an international standard forensic database," Croat Med. J. (2001) 42:315-327.
Moricca et al., "Detection of *Fusarium oxysporum* f.sp. Vasinfectum in cotton tissue by polymerase chain reaction" *Plant Pathology* (1998) 47:486-494.
Morse et al., "Nucleotide Sequence of Part of the ropC Gene Encoding the B Subunit of DNA-Dependent RNA Polymerase from some Gram-Positive Bacteria and Comparative Amino Acid Sequence Analysis" *System Appl. Microbiol.* (1996) 19:150-157.
Muddiman et al., "Application of secondary ion and matrix-assisted laser desorption-ionization time-of-flight mass spectrometry for the quantitative analysis of biological molecules" *Mass Spectrometry Reviews* (1996) 14:383-429.
Muddiman et al., "Important aspects concerning the quantification of biomolecules by time-of-flight secondary-ion mass spectrometry" *Applied Spectroscopy* (1996) 50:161-166.
Muddiman et al., "Characterization of PCR Products from Bacilli Using Electrospray Ionization FTICR Mass Spectrometry" *Anal. Chem.* (1996) 68:3705-3712.
Muddiman et al., "Length and base composition of PCR-amplified nucleic acids using mass measurements from electrospray ionization mass spectrometry" *Anal. Chem.* (1997) 69:1543-1549.
Muddiman et al., "Sequencing and Characterization of Larger Oligonucleotides by Electrospray Ionization Fourier Transform Ion Cyclotron Resonance Mass Spectrometry" *Reviews in Analytical Chemistry* (1998) 17:1-68.
Muddiman et al., "Precise mass measurement of a double-stranded 500 base-pair (309 kDa) polymerase chain reaction product by negative ion electrospray ionization fourier transform ion cyclotron resonance mass spectrometry" *Rapid Commun. Mass Spec.* (1999) 13:1201-1204.
Muhammad et al., "Electrospray ionization quadrupole time-of-flight mass spectrometry and quadrupole mass spectrometry for genotyping single nucleotide substitutions in intact polymerase chain reaction products in K-ras and p53" *Rapid Commun. Mass Spectrom.* (2002) 16:2278-2285.
Mushegian et al., "A minimal gene set for ceullular life derived by comparison of complete bacterial genomes" Proc. Natl. Acad. Sci. USA (1996) 93:10268-10273.
Nagpal et al., "Utility of 16S-23S RNA spacer region methodology: how similar are interspace regions within a genome and between strains for closely related organisms?" *Journal of Microbiological Methods* (1998) 33:211-219.
Nakao et al., "Development of a Direct PCR Assay for Detection of the Diphtheria Toxin Gene" *J. Clin. Microbiol.* (1997) 35:1651-1655.
Naumov et al., "Discrimination of the Soil Yest Species *Williopsis saturnus* and *Williopsis suaveolens* by the Polymerase Chain Reaction with the Universal Primer N21" *Microbiology (Moscow)(Translation of Mikrobiologiya)* (2000) 69:229-233.
Nishikawa et al., "Reconstitution of active recombinant Shiga toxin (Stx)1 from recombinant Stxl-A and Stxl-B subunits independently produced by *E. coli* clones" *FEMS* (1999) 178:13-18.
Norder et al., "Typing of Hepatitis B Virus Genomes by a Simplified Polymerase Chain Reaction" *J. Med. Virol.* (1990) 31:215-221.
Null et al., "Preparation of single-stranded PCR products for electrospray ionization mass spectrometry using the DNA repair enzyme lambda exonuclease" *Analyst* (2000) 125:619-626.
Null et al., "Genotyping of Simple and Compound Short Tandem Repeat Loci Using Electrospray Ionization Fourier Transform Ion Cyclotron Resonance Mass Spectrometry" Analytical Chemistry (2001) 73:4514-4521.
Null et al., "Perspectives on the use of electrospray ionization Fourier transform ion cyclotron resonance mass spectrometry for short tandem repeat genotyping in the post-genome era" *Journal of Mass Spectrometry* (2001) 36:589-606.
Null et al., "Evaluation of sample preparation techniques for mass measurements of PCR products using ESI-FT-ICR mass spectrometry" *Journal of the American Society for Mass Spectrometry* (2002) 13:338-344.
Null et al., "Determination of a correction to improve mass measurement accuracy of isotopically unresolved polymerase chain reaction amplicons by electrospray ionization Fourier transform ion cyclotron resonance mass spectrometry" *Rapid Comm. Mass Spectrom.* (2003) 17:1714-1722.

Null et al., "Implications of hydrophobicity and free energy of solvation for characterization of nucleic acids by electrospray ionization mass spectrometry" *Anal. Chem.* (2003) 75:1331-1339.
Parson et al., "Population data for 101 Austrian Caucasian mitochondrial DNA d-loop sequences: Application of mtDNA sequence analysis to a forensic case" *Int. J. Legal Med.* (1998) 111:124-132.
Paterson et al., "Fine Mapping of Quantitative Trait Loci Using Selected Overlapping Recombinant Chromosomes, in an Interspecies Cross of Tomato" *Genetics* (1990) 124:735-742.
Peng et al., "Rapid detection of *Shigella* species in environmental sewage by an immunocapture PCR with universal primers" *Applied and Environmental Microbiology* (2002) 68:2580-2583.
Pomerantz et al., "Determination of oligonucleotide composition from mass spectrometrically measured molecular weight" *Journal of the American Society for Mass Spectrometry* (1993) 4:204-209.
Raaum, R. L. et al., "Catarrhine primate divergence dates estimated from complete mitochondrial genomes: concordance with fossil and nuclear DNA evidence," *J. Hum. Evol.* (2005) 48:237-257.
Reid et al., "Primary diagnosis of foot-and-mouth disease by reverse transcription polymerase chain reaction" *Journal of Virological Methods* (2000) 89:167-176.
Reilly et al., "Design and use of 16S ribosomal DNA-directed primers in competitive PCRs to enumerate proteolytic bacteria in the rumen" *Microb. Ecol.* (2002) 43:259-270.
Ross et al., "Discrimination of Single-Nucleotide Polymorphisms in Human DNA Using Peptide Nucleic Acid Probes Detected by MALDI-TOF Mass Spectrometry" *Anal. Chem.* (1997) 69:4197-4202.
Ross et al., "Analysis of DNA fragments from conventional and microfabricated PCR devices using delayed extraction MALDI-TOF mass spectrometry" *Anal. Chem.* (1998) 70:2067-2073.
Sala et al., "Ambiguous base pairing of the purine analogue 1-(20deoxy-B-D-ribofuranosyl)-imidazole-4-carboxamide during PCR" *Nucl. Acids Res.* (1996) 24:3302-3306.
Sauer et al., "A novel procedure for efficient genotyping of single nucleotide polymorphisms" *Nucleic Acids Research* (2000) 28:E13.
Scaramozzino et al., "Comparison of Flavivirus universal primer pairs and development of a rapid, highly sensitive heminested reverse transcription-PCR assay for detection of flaviviruses targeted to a conserved region of the NS5 gene sequences" *J. Clin. Microbiol.* (2001) 39:1922-1927.
Schram et al., "Mass Spectrometry of Nucleic Acid Components" *Biomedical Applications of Mass Spectrometry* (1990) 34:203-280.
Schultz et al., "Polymerase chain reaction products analyzed by charge detection mass spectrometry" *Rapid Communications in Mass Spectrometry* (1999) 13:15-20.
Senko et al., "Determination of Monoisotopic Masses and Ion Populations for Large Biomolecules from Resolved Isotopic Distributions," *J. Am. Soc. Mass Spectrom.* (1995) 6:229.
Seshardi et al., "Differential Expression of Translational Elements by Life Cycle Variants of *Coxiella burnetii" Infect. Immun.* (1999) 67:6026-6033.
Shaver et al., "Variation in 16S-23S rRNA intergenic spacer regions among *Bacillus subtilis* 168 isolates" *Molecular Microbiology* (2001) 42:101-109.
Shaver et al., "Restriction fragment length polymorphism of rRNA operons for discrimination and intergenic spacer sequences for cataloging *Bacillus subtilis* sub-groups" *J. Microbiol Methods* (2002) 50:215223.
Srinivasan et al., "Matrix-assisted laser desorption/ionization time-of-flight mass spectrometry as a rapid screening method to detect mutations causing Tay-Sachs disease" *Rapid Communications in Mass Spectrometry* (1997) 11:1144-1150.
Steffens et al., "Sequence analysis of mitochondrial DNA hybervariable regions using infrared fluorescence detection" *BioTechniques* (1999) 24:1044-1046.
Stoneking et al., "Population variation of human mDNA control region sequences detected by enzymatic amplification and sequence-specific oligonucleotide probes," American Journal of Human Genetics (1991) 48:370-382.
Takahashi et al., "Characterization of gryA, gryB, gr1A and gr1B mutations in fluoroquinolone-resistant clinical isolates of *Staphylococcus aureus" J. Antimicrob. Chemother* (1998) 41:49-57.
Takeuchi et al., "Serotyping of Adenoviruses on Conjunctival Scrapings by PCR and Sequence Analysis" *Journal of Clinical Microbiology* (1999) 37:1839-1845.
Tatuch et al., "Heteroplasmic mtDNA mutation (T-G) at 8993 can cause Leigh disease when the percentage of abnormal mtDNA is high" *Am. J. Hum. Genet.* (1992) 50:852-858.
Tong et al., "Ligation reaction specificities of an Nad+-dependent DNA ligase from the hyperthermophile *Aquifex aeolicus" Nucleic Acids Res* (2000) 28:1447-1454.
Torroni et al., "Classification of European mtDNAs from an Analysis of Three European Populations" *Genetics* (1996) 144:1835-1850.
Van Aerschot et al., "In search of acyclic analogues as universal nucleosides in degenerate probes" *Nucleosides and Nucleotides* (1995) 14:1053-1056.
Van Baar et al., "Characterization of Bacteria by Matrix Assisted Laser Desorption/Ionization and Electrospray Mass Spectrometry" *FEMS Microbiol. Review* (2000) 24:195-219.
Van Camp et al., "Amplification and sequencing of variable regions in bacteria 23S ribosomal RNA genes with conserved primer sequences" *Current Microbiology* (1993) 27:147-151.
Van Der Vossen et al., "DNA based typing, identification and detection systems for food spoilage microorganisms: development and implementation" *Int. J. Food Microbiol.* (1996) 33:35-49.
Van Ert et al., "Mass spectrometry provides accurate characterization of two genetic marker types in *Bacillus anthracis" Biotechniques* (2004) 37:642-651.
Vanderhallen et al., "Identification of Encephalomyocarditis Virus in Clinical Samples by Reverse Transcription-PCR Followed by Genetic Typing Using Sequence Analysis" *J. Clin. Microbiol.* (1998) 36:3463-3467.
Walters et al., "Genotyping single nucleotide polymorphisms using intact polymerase chain reaction products by electrospray quadrupole mass spectrometry" *Rapid Communications in Mass Spectrometry* (2001) 15:1752-1759.
Welham et al., "The Characterization of Micro-organisms by Matrix-assisted Laser Desorption/Ionization Time-of-flight Mass Spectrometry" *Rapid Communications in Mass Spectrometry* (1988) 12:176-180.
Widjojoatmodjo et al., "Rapid Identification of Bacteria by PCR-Single-Strand Conformation Polymorphism" *Journal of Clinical Microbiology* (1994) 3002-3007.
Wolter et al., "Negative Ion FAB Mass Spectrometric Analysis of Non-Charged Key Intermediates in Oligonucleotide Synthesis: Rapid Identification of Partially Protected Dinucleoside Monophosphates" *Biomed. Environ. Mass Spectrom.* (1987) 14:111-116.
Woo et al., "Identification of Leptospira inadai by continuous monitoring of fluorescence during rapid cycle PCR" *Systematic and Applied Microbiology* (1998) 21:89-96.
Wunschel et al., "Discrimination Among the B. Cereus Group, in Comparison to B. Subtilis, by Structural Carbohydrate Profiles and Ribosomal RNA Spacer Region PCR" *System. Appl. Microbiol.* (1994) 17:625-635.
Wunschel et al., "Analysis of double-stranded polymerase chain reaction products from the Bacillus cereus group by electrospray ionization Fourier transform ion cyclotron resonance mass spectrometry" *Rapid Communications in Mass Spectrometry* (1996) 10:29-35.
Wunschel et al., "Mass spectrometric characterization of DNA for molecular biological applications: Advances using MALDI and ESI" *Advances in Mass Spectrometry* (1998) 14:Chapter 15/377-Chapter 15/406.
Wunschel et al., "Heterogeneity in baciullus cereus PCR products detected by ESI-FTICR mass spectrometry" *Anal. Chem.* (1998) 70:1203-1207.
Yao et al., "Mass Spectrometry Based Proteolytic Mapping for Rapid Virus Detection" *Anal. Chem.* (2002) 74:2529-2534.
Yasui et al., "A specific oligonucleotide primer for the rapid detection of *Lactobacillus lindneri* by polymerase chain reaction" *Can. J. Microbiol.* (1997) 43:157-163.

Zeng et al., "Precision Mapping of Quantitative Trait Loci" *Genetics* (1994) 136:1457-1468.
Andreasson et al., "Mitochondrial Sequence Analysis for Forensic Identification Using Pyrosequencing Technology" *BioTechniques* (2002) 32:124-133.
Ingman et al., "Mitochondrial genome variation and the origin of modern humans" *Nature* (2000) 408:708-713.
Nilsson et al., "Evaluation of mitochondrial DNA coding region assays for increased discrimination in forensic analysis" *Forensic Science International: Genetics* (2008) 2:1-8.
Aaserud D.J., et al., "DNA Sequencing with Balckbody Infrared Radioactive Dissociation of Electrosprayed Ions," International Journal of Mass Spectrometry and Icon Processes, 1997, vol. 167-168, pp. 705-712.
Adam E., et al., "Characterization of Intertype Specific Epitopes on Adenovirus Hexons," Archives of Virology, 1998, vol. 143 (9), pp. 1669-1682.
Adam E., et al., "Intertype Specific Epitope Structure of Adenovirus Hexon," Acta Microbiologica et Immunologica Hungarica, 1998, vol. 45 (3-4), pp. 311-316.
Adam E., et al., "Molecular Structure of the Two-Dimensional Hexon Crystalline Array and of Adenovirus Capsid," Acta Microbiologica et Immunologica Hungarica, 1998, vol. 45 (3-4), pp. 305-310.
Adrian T., et al., "DNA Restriction Analysis of Adenovirus Prototypes 1 to 41," Archives of Virology, 1986, vol. 91 (3-4), pp. 277-290.
Adzhar A., et al., "Universal Oligonucleotides for the Detection of Infectious Bronchitis Virus by Thepolymerase Chain Reaction," Avian Pathology : Journal of the W.V.P.A, 1996, vol. 25 (4), pp. 817-836.
Agostini H.T., et al., "Complete Genome of a JC Virus Genotype Type 6 from the Brain of an African American with Progressive Multifocal Leukoencephalopathy," Journal of Human Virology, 1998, vol. 1 (4), pp. 267-272.
Aires De Sousa M., et al., "Bridges from Hospitals to the Laboratory: Genetic Portraits of Methicillin-Resistant Staphylococcus Aureus Clones," FEMS Immunology and Medical Microbiology, 2004, vol. 40 (2), pp. 101-111.
Akalu A., et al., "Rapid Identification of Subgenera of Human Adenovirus by Serological and PCR Assays," Journal of Virological Methods, 1998, vol. 71 (2), pp. 187-196.
Alba M.M., et al., "Vida: A Virus Database System for the Organization of Animal Virus Genome Open Reading Frames," Nucleic Acids Research, vol. 29 (1), pp. 133- 136., 2001.
Allaouchiche B., et al., "Clinical Impact of Rapid Oxacillin Susceptibility Testing Using a PCR Assay in Staphylococcus Aureus Bactaeremia," The Journal of Infection, 1999, vol. 39 (3), pp. 198-204.
Allawi H.T., et al., "Thermodynamics and Nmr of Internal G.T. Mismatches in DNA," Biochemistry, 1997, vol. 36 (34), pp. 10581-10594.
Altschuel S.F., et al., "Basic Local Alignment Search Tool," Journal of Molecular Biology, 1990, vol. 215 (3), pp. 403-410.
Altschuel S.F., et al., "Gapped BLAST and PSI-BLAST: A New Generation of Protein Database Search Programs," Nucleic Acids Research, 1997, vol. 25 (17), pp. 3389-3402.
Amano Y., et al., "Detection of Influenza Virus: Traditional Approaches and Development of Biosensors," Analytical and Bioanalytical Chemistry, 2005, vol. 381 (1), pp. 156-164.
Amexis G., et al., "Quantitative Mutant Analysis of Viral Quasispecies by Chip-Based Matrix Assisted LaserDesorption Ionization Time-of-Flight Mass Spectrometry," Proceedings of the National Academy of Sciences, 2001, vol. 98 (21), pp. 12097-12102.
Anderson M.L.M., "Quantitative Filter Hybridization" in: Nucleic Acid Hybridization, Hames B.D. ed., IRL Press, 1985, pp. 73-111.
Anthony R.M., et al., "Use of the Polymerase Chain Reaction for Rapid Detection of High- Level Mupirocin Resistance in Staphylococci," European Journal of Clinical Microbiology & Infectious Diseases, 1999, vol. 18 (1), pp. 30-34.
Arbique J., et al., "Comparison of the Velogene Rapid MRSA Identification Assay, Denka MRSAScreen Assay, and BBL Crystal MRSA ID System for Rapid Identification of Methicillin-Resistant Staphylococcus Aureus," Diagnositic Microbiology and Infectious Diseases, 2001, vol. 40 (1-2), pp. 5-10.
Archer G.L., et al., "Detection of Methicillin Resistance in Staphylococci by Using a DNA Probe," Antimicrobial Agents and Chemotherapy, 1990, vol. 34 (9), pp. 1720-1724.
Armstrong P., et al., "Sensitive and Specific Colorimetric Dot Assay to Detect Eastern Equine Encephalomyelitis Viral RNA in Mosquitoes After PCR Amplification," Journal of Medicinal Entomology, 1995, vol. 32 (1), pp. 42-52.
Arnal C., et al., "Quantification of Hepatitis A virus in shellfish by competitive reverse transcription PCRwith coextraction of standard RNA," Applied and Environmental Microbiology, 1999, vol. 65 (1), pp. 322-326.
Aronsson F., et al., "Persistence of the influenza A/WSN/33 virus RNA at midbrain levels of immunodefective mice," Journal of Neurovirology, 2001, vol. 7 (2), pp. 117-124.
Ausubel F.M., et al., eds., Current Protocols in Molecular Biology, vol. 1, John Wiley & Sons Inc., 2004, Table of Contents.
Ausubel F.M., et al., eds., Short Protocols in Molecular Biology: A Compendium of Methods from Current Protocols in Molecular Biology, 2nd Edition, John Wiley & Sons, 1992, Units 2.9, 3.4-3.17, 4.6-4.10, and 10.8.
Ausubel F.M., et al., "Unit 2.11 "Synthesis and Purification of Oligonucleotides," in: Current Protocols in Molecular Biology," 1998, John Wiley & Sons, Inc., pp. 2.11-2.11.21.
Avellon A., et al., "Rapid and Sensitive Diagnosis of Human Adenovirus Infections by a Generic Polymerase Chain Reaction," Journal of Virological Methods, 2001, vol. 92 (2), pp. 113-120.
Azevedo A.M., et al., "Detection of Influenza, Parainfluenza, Adenovirus and Respiratory Syncytial Virus during Asthma Attacks in Children Older than 2 Years Old," Allergologia Immunopathologia, 2003, vol. 31 (6), pp. 311-317.
Baba T., et al., "Genome and Virulence Determinants of High Virulence Community-Acquired MRSA," Lancet, 2002, vol. 359 (9320), pp. 1819-1827.
Bai J., et al., "Matrix-Assisted Laser Desorption/Ionization Mass Spectrometry of Restriction Enzyme-Digested Plasmid DNA Using an Active Nafion Substrate," Rapid Communications in Mass Spectrometry, 1994, vol. 8 (9), pp. 687-691.
Banik U., et al., "Multiplex PCR Assay for Rapid Identification of Oculopathogenic Adenoviruses by Amplification of the Fiber and Hexon Genes," Journal of Clincal Microbiology, 2005, vol. 43 (3), pp. 1064-1068.
Barbour A.G., et al., "Identification of an Uncultivatable Borrelia Species in the hard tick Amblyomma Americanum: Possible Agent of a Lyme disease-like illness," The Journal of Infectious Diseases, 1996, vol. 173 (2), pp. 403-409.
Barns S.M., et al., "Detection of Diverse New Francisella-like Bacteria in Environmental Samples," Applied and Environmental Microbiology, 2005, vol. 71 (9), pp. 5494-5500.
Baron E.J., "Genetic Aspects of Methicillin Resistance in Staphylococcus aureus and MethodsUsed for its Detection in Clinical Laboratories in the United States," Journal of Chemotherapy, 1995, vol. 7 (Supl.3), pp. 87-92.
Barr I.G., et al., "An Influenza A(H3) Reassortant Was Epidemic in Australia and New Zealand in 2003," Journal of Medical Virology, 2005, vol. 76 (3), pp. 391-397.
Barski P., et al., "Rapid Assay for Detection of Methicillin-Resistant Staphylococcus Aureus Using Multiplex PCR," Molecular and Cellular Probes, 1996, vol. 10 (6), pp. 471-475.
Beall B., et al., "Sequencing emm-Specific PCR Products for Routine andAccurate Typing of Group A Streptococci," Journal of Clincal Microbiology, 1996, vol. 34 (4), pp. 953-958.
Beall B., et al., "Survey of emm Gene Sequences and T-Antigen Types fromSystemic *Streptococcus pyogenes* nfection Isolates Collected in San Francisco, California; Atlanta, Georgia; and Connecticut in 1994 and 1995," Journal of Clincal Microbiology, 1997, vol. 35 (5), pp. 1231-1235.
Benko, M. et al., "Family Adenoviridae," Virus taxonomy. VIIIth report of the International Committee on Taxonomy of Viruses, 2004, Academic Press, New York, pp. 213-228.
Benson D.A., et al., "GenBank," Nucleic Acids Research, 1999, vol. 27 (1), pp. 12-17.

Berencsi G., et al., "Molecular Biological Characterization of Adenovirus DNA," Acta Microbiologica et Immunologica Hungarica, 1998, vol. 45 (3-4), pp. 297-304.
Bishop M.J., et al., "Molecular Sequence Databases" in: Nucleic Acid and Protein Sequence Analysis, 4th Chapter, Bishop M.J., et al., eds, IRL Press, 1987, pp. 83-113.
Bisno A.L., "Streptococcus Pyogenes in Infectious Diseases and Their Etiologic Agents "Principles and Practice of Infectious Diseases, 1995, vol. 2, pp. 1786-1799.
Blaiotta G., et al., "PCR Detection of Staphylococcal Enterotoxin Genes in Staphyiococcus Spp. Strains Isolated from Meat and Dairy Products. Evidence for New Variants of seG and Sel in S. Aureus AB-8802," Journal of Applied Microbiology, 2004, vol. 97 (4), pp. 719-730.
Bolton E.T., et al., "A general method for the isolation of RNA complementary to DNA," Proceedings of the National Academy of Sciences of the USA, 1962, vol. 48, pp. 1390-1397.
Bonk T., et al., "Matrix-Assisted Laser Desorption/Ionization Time-of-Flight Mass Spectrometry-Based Detection of Microsatellite Instabilities in Coding DNA Sequences: A Novel Approach to Identify DNA-Mismatch Repair-Deficient Cancer Cells," Clinical Chemistry, 2003, vol. 49 (4), pp. 552-561.
Boubaker K., et al., "Panton-Valentine Leukocidin and Staphyloccoccal Skin Infections in Schoolchildren," Emerging Infectious Diseases, 2004, vol. 10 (1), pp. 121- 124.
Bowers K.M., et al., "Screening for Methicillin Resistance in Staphylococars Aureus and coagulasenegative Staphylococci: Evaluation of Three Selective and Mastalex-MRSA latex Agglutination," British Journal of Biomedical Science, 2003, vol. 60 (2), pp. 71-74.
Brakstad O.G., et al., "Direct Identification of Staphylococcus Aureus in Blood Cultures Bydetection of the Gene, Encoding the Thermostable Nuclease or the Gene Product," Acta Pathologica, Microbiologica et Immunologica Scandinavica, 1995, vol. 103 (3), pp. 209-218.
Brakstad O.G., et al., "Multiplex Polymerase Chain Reaction for Detection of Genes for Staphylococcus Aureus Themonuclease and Methicillin Resistance and Correlation with Oxacillin Resistance," Acta Pathologica, Microbiologica et Immunologica Scandinavica, 1993, vol. 101 (9), pp. 681-688.
Brandt C.D., et al., "Infections in 18,000 Infants and Children in a Controlled Study of Respiratory Tract Disease. I. Adenovirus Pathogenicity in Relation to Serologic Type and Illness Syndrome," American Journal of Epidemiology, 1969, vol. 90 (6), pp. 484-500.
Brayshaw D.P., "Methicillin-Resistant Staphylococcus Aureus: Evaluation of Detection Techniques on Laboratory-Passaged Organisms," British Journal of Biomedical Science, 1999, vol. 56 (3), pp. 170-176.
Brightwell G., et al., "Development of Internal Controls for PCR Detection of Bacillus Anthracis," Molecular and Cellular Probes, 1998, vol. 12 (6), pp. 367-377.
Brightwell G., et al., "Genetic Targets for the Detection and Identifiaction of Venezuelan Equine Encephalitis Viruses," Archives of Virology, 1998, vol. 143 (4), pp. 731-742.
Bronzoni R.V.M., et al., "Duplex Reverse Transcription-PCR Followed by Nested PCR Assays for Detection and Identification of Brazilian Alphaviruses and Flaviviruses," Journal of Clincal Microbiology, 2005, vol. 43 (2), pp. 696-702.
Bronzoni R.V.M., et al., "Multiplex Nested PCR for Brazilian Alphavirus Diagnosis," Transactions of the Royal Society of Tropical Medicine and Hygiene, 2004, vol. 98 (8), pp. 456-461.
Brown I.H., "Advances in Molecular Diagnostics for Avian Influenza," Developments in Biologicals, 2006, vol. 124, pp. 93-97.
Brownstein M.J., et al., "Modulation of Non-Templated Nucleotide Addition by Taq DNA Polymerase: Primer Modifications that Facilitate Genotyping," BioTechniques, 1996, vol. 20 (6), pp. 1004-1010. DNA Polymerase: Primer Modifications that Facilitate Genotyping, BioTechniques, 1996, vol. 20 (6), pp. 1004-1010.
Brunaud V., et al., "T-DNA Integration into the Arabidopsis Genome Depends on Sequence of Pre-Insertion Sites," EMBO Reports, 2002, vol. 3 (12), pp. 1152-1157.
Buck G.A., et al., "Design Strategies and Performance of Custom DNA Sequencing Primers," BioTechniques, 1999, vol. 27 (3), pp. 528-536.
Buetow K.H., et al., "High-Throughput Development and Characterization of a Genomewide Collection of Gene-Based Single Nucleotide Polymorphism Markers by Chip-Based Matrix-Assisted Laser Desorption/Ionization Time-of-Flight Mass Spectrometry," Proceedings of the National Academy of Sciences, 2001, vol. 98 (2), pp. 581-584.
Butel J.S., et al., "Cell and Molecular Biology of Simian Virus 40: Implications for Human Infections and Disease," Journal of the National Cancer Institute, 1999, vol. 91 (2), pp. 119-134.
Butler J., "DNA Profiling and Quantitation of Human DNA," CCQM Bio Analysis Working Group, 2005.
Carroll K.C., et al., "Rapid Detection of the Staphylococcal mecA Gene from BACTEC BloodCulture Bottles by the Polymerase Chain Reaction," American Journal of Clincal Pathology, 1996, vol. 106 (5), pp. 600-605.
Cattoli G., et al., "Comparison of Three Rapid Detection Systems for Type A Influenza Virus on Tracheal Swabs of Experimentally and Naturally Infected Birds," Avian Pathology, 2004, vol. 33 (4), pp. 432-437.
Cavassini M., et al., "Evaluation of MRSA-Screen, a Simple Anti-PBP 2a Slide Latex AgglutinationKit, for Rapid Detection of Methicillin Resistance in *Staphylococcus aureus*," Journal of Clincal Microbiology, 1999, vol. 37 (5), pp. 1591-1594.
Certificate of Correction mailed Mar. 31, 2008 for U.S. Appl. No. 09/891,793, filed Jun. 26, 2001.
Certificate of Correction mailed Mar. 31, 2008 for U.S. Appl. No. 10/156,608 filed May 24, 2002.
Certificate of Correction mailed Mar. 31, 2008 for U.S. Appl. No. 10/660,997 filed Sep. 12, 2003.
Chamberlin M., et al., "New RNA Polymerase from Escerichia Coli Infected with Bacteriophage T7," Nature, 1970, vol. 228 (5268), pp. 227-231.
Chandra S., et al., "Virus Reduction in the Preparation and Intravenous Globulin: In Vitro Experiments," Transfusion, 1999, vol. 39 (3), pp. 249-257.
Chaves F., et al., "Molecular Characterization of Resistance to Mupirocin in Methicillin- Susceptible and -Resistant Isolates of *Staphylococcus aureus* from Nasal Samples," Journal of Clincal Microbiology, 2004, vol. 42 (2), pp. 822-824.
Chelly J., et al., "Transcription of the Dystrophin Gene in Human Muscle and Non-Muscle Tissue," Nature, 1988, vol. 333 (6176), pp. 858-860.
Chen C.H., et al., Laser Desorption Mass Spectrometry for FastDNA Sequencing [online], Nov. 1994, Retrieved from the Internet< URL:http://www.ornl.gove/sci/techresources/Human_Genome/publicat/94SANTA/sequencing/segtoc.shtml>.
Chen R., et al., "Trapping, Detection, and Charge and Mass Measurement of Large Individual Ions (up to 1.1 X 108 Daltons) by Electrospray Ionization FTICR MS," 42nd ASMS Conference on Mass Spectrometry, 1994.
Chen Y.Z., et al., "A BAC-Based STS-Content Map Spanning a 35-Mb Region of Human Chromosome 1p35-36," Genomics, 2001, vol. 74 (1), pp. 55-70.
Chen Z., et al., "Genetic Mapping of the Cold-Adapted Phenotype of B/Ann Arbor/1/66, the Master Donor Virus for Live Attenuated Influenza Vaccines (FluMist)," Virology, 2006, vol. 345 (2), pp. 416-423.
Chinese Application No. CN1202204 filed Dec. 16, 1998, Sequenom Inc.
Chiu N. H., et al., "Mass Spectrometry of Single-Stranded Restriction Fragments Captured by an Undigested Complementary Sequence," Nucleic Acids Research, 2000, vol. 28 (8), pp. E31.
Chmielewicz B., et al., "Development of a PCR-Based Assay for Detection, Quantification, and Genotyping of Human Adenoviruses," Clinical Chemistry, 2005, vol. 51 (8), pp. 1365-1373.
Choi S., et al., "Real-Time PCR Quantification of Human Adenoviruses in Urban Rivers Indicates Genome Prevalence but Low Infectivity," Applied and Environmental Microbiology, 2005, vol. 71 (11), pp. 7426-7433.
Choi Y.K., et al., "Detection and Subtying of Swine Influenza H1N1, H1 N2 and H3N2 Viruses in Clinical Samples Using Two Multiplex RT-PCR Assays," Journal of Virological Methods, 2002, vol. 102 (1-2), pp. 53-59.

Christel L.A., et al., "Rapid, Automated Nucleic Acid Probe Assays Using Silicon Microstructures forNucleic Acid Concentration," Journal of Biomechanical Engineering, 1999, vol. 121 (1), pp. 22-27.
Claas E.C., et al., "Internally Controlled Real-Time PCT Monitoring of Adenovirus DNA Load inSerum or Plasma of Transplant Recipients," Journal of Clincal Microbiology, 2005, vol. 43 (4), pp. 1738-1744.
Cloney L., et al., "Rapid Detection of mecA in Methicillin Resistant Staphylococcus Aureus Using Cycling Probe Technology," Molecular and Cellular Probes, 1999, vol. 13 (13), pp. 191-197.
Collins D.W., et al., "Numerical Classification of Coding Sequences," Nucleic Acids Research, 1992, vol. 20 (6), pp. 1405-1410.
Contreras-Salazar B., et al., "Up Regulation of the Epstein-Barr Virus (EBV)-Encoded Membrane Protein LMP in the Burkitt's Lymphoma Line Daudi after Exposure to N-Butyrate and after EBV Superinfection," Journal of Virology, 1990, vol. 64 (11), pp. 5441-5447.
Co-pending U.S. Appl. No. 10/318,681.
Co-pending U.S. Appl. No. 10/323,186.
Co-pending U.S. Appl. No. 10/323,187.
Co-pending U.S. Appl. No. 10/324,721.
Co-pending U.S. Appl. No. 10/521,662.
Co-pending U.S. Appl. No. 10/754,415.
Co-pending U.S. Appl. No. 10/807,019.
Co-pending U.S. Appl. No. 10/845,052.
Co-pending U.S. Appl. No. 10/964,571.
Co-pending U.S. Appl. No. 11/209,439.
Co-pending U.S. Appl. No. 11/674,538.
Co-pending U.S. Appl. No. 11/682,259.
Co-pending U.S. Appl. No. 11/929,910.
Co-pending U.S. Appl. No. 11/930,108.
Co-pending U.S. Appl. No. 11/930,741.
Co-pending U.S. Appl. No. 90/010,209.
Co-pending U.S. Appl. No. 90/010,210.
Co-pending U.S. Appl. No. 90/010,447.
Co-pending U.S. Appl. No. 90/010,448.
Co-pending U.S. Appl. No. 11/233,630, filed on Sep. 21, 2005.
Co-pending U.S. Appl. No. 60/639,068, filed on Dec. 22, 2004.
Co-pending U.S. Appl. No. 60/648,188, filed on Jan. 28, 2005.
Couto I., et al., "Development of Methicillin Resistance in Clinical Isolates of Staphylococcus Sciuri by Transcriptional Activation of the mecA Homologue Native to the Species," Journal of Bacteriology, 2003, vol. 185 (2), pp. 645-653.
Crawford-Miksza L., et al., "Analysis of 15 Adenovirus Hexon Proteins Reveals the Location and Structure of Seven Hypervariable Regions Containing Serotype-Specific Residues," Journal of Virology, 1996, vol. 70 (3), pp. 1836-1844.
Crawford-Miksza L.K., et al., "Adenovirus Serotype Evolution is Driven by Illegitimate Recombination in the Hypervariable Regions of the Hexon Protein," Virology, 1996, vol. 224 (2), pp. 357-367.
Crawford-Miksza L.K., et al., "Strain Variation in Adenovirus Serotypes 4 and 7a Causing Acute Respiratory Disease," Journal of Clincal Microbiology, 1999, vol. 37 (4), pp. 1107-1112.
Cui L., et al., "Contribution of a Thickened Cell Wall and Its Glutamine Nonamidated Component to the Vancomycin Resistance Expressed by *Staphylococcus aureus* Mu50," Antimicrobial Agents and Chemotherapy, 2000, vol. 44 (9), pp. 2276-2285.
De Jong J.C., et al., "Adenoviruses from Human Immunodeficiency Virus-Infected Individuals,Including Two Strains That Represent New Candidate Serotypes Ad50 and Ad51 of Species B1 and D, Respectively," Journal of Clincal Microbiology, 1999, vol. 37 (12), pp. 3940-3945.
De La Puente-Redondo V.A., et al., "Comparison of Different PCR Approaches for Typing of Francisella Tularensis Strains," Journal of Clinical Microbiology, 2000, vol. 38 (3), pp. 1016-1022.
Del Blanco Garcia N., et al., "Genotyping of Francisella Tularensis Strains by Pulsed-field gel Electrophoresis, Amplified Fragment Length Polymorphism Fingerprinting, and 16S rRNA gene Sequencing," Journal of Clinical Microbiology, 2002, vol. 40 (8), pp. 2964-2972.
Del Vecchio V.G., et al., "Molecular Genotyping of Methicillin-Resistant *Staphylococcus aureus* via Fluorophore-Enhanced Repetitive-Sequence PCR," Journal of Clincal Microbiology, 1995, vol. 33 (8), pp. 2141-2144.
Denis M., et al., "Development of a Semiquantitative PCR Assay Using Internal Standard and Colorimetricdetection on Microwell Plate for Pseudorabies Virus," Molecular and Cellular Probes, 1997, vol. 11 (6), pp. 439-448.
Deurenberg R.H., et al., "Rapid Detection of Panton-Valentine Leukocidin from Clinical Isolates of Staphylococcus Aureus Strains by Real-Time PCR," FEMS Microbiology Letters, 2004, vol. 240 (2), pp. 225-228.
Deurenberg R.H., et al., "The Prevalence of the Staphylococcus Aureus tst Gene among Community— and Hospital-Acquired Strains and Isolates from Wegener's Granulomatosis Patients," FEMS Microbiology Letters, 2005, vol. 245 (1), pp. 185-189.
Di Guilmi A.M., et al., "Human Adenovirus Serotype 3 (Ad3) and the Ad3 fiber Protein Bind to a 130-kDa Membrane Protein on HLa Cells," Virus Research, 1995, vol. 38 (1), pp. 71-81.
Diep B.A., et al., "Complete Genome Sequence of USA300, an Epidemic Clone of Community Acquired Meticillin-Resistant Staphylococcus Aureus," Lancet, 2006, vol. 367 (9512), pp. 731-739.
Ding C., et al., "A High-Throughput Gene Expression Analysis Technique using Competiive PCR and Matrixassisted Laser Desorption Ionization time-of-Flight MS," Proceedings of the National Academy of Sciences, 2003, vol. 100 (6), pp. 3059-3064.
Donehower L.A., et al., "The Use of Primers from Highly Conserved Pol Regions to Identify Uncharacterized Retroviruses by the Polymerase Chain Reaction," Journal of Virological Methods, 1990, vol. 28 (1), pp. 33-46.
Donofrio J.C., et al., "Detection of Influenza A and B in Respiratory Secretions with the Polymerase Chain Reaction," PCR Methods and Applications, 1992, vol. 1 (4), pp. 263-268.
Doty P., et al., "Strand Separation and Specific Recombination in Deoxyribonucleic Acids: Physical Chemical Studies," Proceedings of the National Academy of Sciences of USA, 1960, vol. 46 (4), pp. 461-476.
Drosten C., et al., "Identification ofa Novel Coronavirus in Patients with Severe Acute Respiratory Syndrome," New England Journal of Medicine, 2003, vol. 348 (20), pp. 1967-1976.
Ebner K., et al., "Molecular Detection and Quantitative Analysis of the Entire Spectrum of Human Adenoviruses by a Two-Reaction Real-Time PCR Assay," Journal of Clinical Microbiology, 2005, vol. 43 (7), pp. 3049-3053.
Ebner K., et al., "Typing of Human Adenoviruses in Specimens from Immunosuppressed Patients by PCR-Fragment Length Analysis and Real-Time Quantitative PCR," Journal of Clinical Microbiology, 2006, vol. 44 (8), pp. 2808-2815.
Echavarria M., et al., "Detection of Adenoviruses (AdV) in Culture-Negative EnvironmentalSamples by PCR During an AdV-Associated Respiratory Disease Outbreak," Journal of Clinical Microbiology, 2000, vol. 38 (8), pp. 2982-2984.
Echavarria M., et al., "PCR Method for Detection of Adenovirus in Urine of Healthy and Human Immunodeficiency Virus-Infected Individuals," Journal of Clinical Microbiology, 1998, vol. 36 (11), pp. 3323-3326.
Echavarria M., et al., "Prediction of Severe Disseminated Adenovirus Infection by Serum PCR," Lancet, 2001, vol. 358 (9279), pp. 384-385.
Echavarria M., et al., "Rapid Detection of Adenovirus in Throat Swab Specimens by PCR DuringRespiratory Disease Outbreaks among Military Recruits," Journal of Clinical Microbiology, 2003, vol. 41 (2), pp. 810-812.
Echavarria M., et al., "Use of PCR to Demonstrate Presence of Adenovirus Species B, C, or F as Well as Coinfection with Two Adenovirus Species in Children with Flu-Like Symptoms," Journal of Clinical Microbiology, 2006, vol. 44 (2), pp. 625-627.
Ecker D. J., et al., "Rapid Identification and Strain-Typing of Respiratory Pathogens for Epidemic Surveillance," Proceedings of the National Academy of Sciences, 2005, vol. 102 (22), pp. 8012-8017.

Ecker D. J., et al., "The Ibis T5000 Universal Biosensor. An Automated Platform for Pathogen Identification and Strain Typing," Journal of the Association for Laboratory Automation, 2006, vol. 11 (6), pp. 341-351.
Ecker D.J., et al., "Ibis T5000: a universal biosensor approach for microbiology," Nature Reviews Microbiology, 2008, vol. 6 (7), pp. 553-558.
Edwards K.M., et al., "Adenovirus Infections in Young Children," Pediatrics, 1985, vol. 76 (3), pp. 420-424.
Ellis J. S., et al., "Molecular Diagnosis of Influenza," Reviews in Medical Virology, 2002, vol. 12 (6), pp. 375-389.
Ellis J.S., et al., "Multiplex Reverse Transcription-PCR for Surveillance of Influenza A and B Viruses in England and Wales in 1995 and 1996," Journal of Clinical Microbiology, 1997, vol. 35(8), pp. 2076-2082.
Elsayed S., et al., "Development and Validation of a Molecular Beacon Probe-Based Real-Time Polymerase Chain Reaction Assay for Rapid Detection of Methicillin Resistance in *Staphylococcus aureus*," Archives of pathology and laboratory medicine, 2003, vol. 127 (7), pp. 845-849.
EMBL "*Arabidopsis thaliana* T-DNA flanking sequence, left border, clone 346C06," Accession No. AJ552897, Mar. 29, 2003.
EMBL "Dog (Clone: CXX.147) primer for STS 147, 3' end, sequence tagged site," Accession No. L15697, Mar. 4, 2000.
EMBL "Sequence 10 from patent US 6563025," Accession No. AR321656, Aug. 31, 2006.
EMBL, "Synthetic construct DNA, reverse primer for human STS sts-AA031654 at 1p36", Accession No. AB068711, May 21, 2003.
Enright M.C., et al., "A multilocus sequence typing scheme for *Streptococcus pneumoniae*: identification of clones associated with serious invasive disease," Microbiology, 1998, vol. 144 (Pt 11), pp. 3049-3060.
Enright M.C., et al., "Multilocus Sequence Typing for Characterization of Methicillin-Resistant and Methicillin-Susceptible Clones of Staphylococcus Aureus," Journal of Clinical Microbiology, 2000, vol. 38(3), pp. 1008-1015.
Enright M.C., et al., "Multilocus Sequence Typing of *Streptococcus pyogenes* and theRelationships between Emm Type and Clone," Infection and Immunity, 2001, vol. 69 (4), pp. 2416-2427.
Enright M.C., et al., "The Evolutionary History of Methicillin-Resistant Staphylococcus Aureus(MRSA)," Proceedings of the National Academy of Sciences of USA, 2002, vol. 99 (11), pp. 7687-7692.
Enright M.C., "The Evolution of a Resistant Pathogen—the Case of MRSA," Current Opinion inPharmacology, 2003, vol. 3 (5), pp. 474-479.
Eremeeva M.E., et al., "Evaluation of a PCR Assay for Quantitation of Rickettsia rickettsii and Closely Related Spotted Fever Group Rickettsiae," Journal of Clinical Microbiology, 2003, vol. 41 (12), pp. 5466-5472.
Erlich H.A., ed., PCR Technology: Principles and Applications for DNA Amplification, , W.H. Freeman and Company, 1989.
Eugene-Ruellan G., et al., "Detection of Respiratory Syncytial Virus A and B and Parainfluenzavirus 3 Sequences in Respiratory Tracts of Infants by a Single PCR with Primers Targeted to the L-Polymerase Gene and Differential Hybridization," Journal of Clinical Microbiology, 1998, vol. 36 (3), pp. 796-801.
Evans P., et al., "Practical Algorithms for Universal DNA Primer Design: An Exercise in Algorithm Engineering," Currents in Computational Molecular Biology, 2001, Les Publications CRM, pp. 25-26.
Ex Parte Re-Examination Certificate for U.S. Appl. No. 90/010,209 mailed Jul. 7, 2009.
Ex Parte Re-Examination Certificate for U.S. Appl. No. 90/010,210, mailed Dec. 28, 2010.
Examiner Interview Summary Record mailed Oct. 29, 2009 for U.S. Appl. No. 10/660,122 filed Sep. 11, 2003.
Examiner Interview Summary Record mailed Nov. 30, 2009 for U.S. Appl. No. 10/660,122 filed Sep. 11, 2003.
Facklam R., et al., "Emm Typing and Validation of Provisional M Types for Group A Streptococci," Emerging Infectious Diseases, 1999, vol. 5 (2), pp. 247-253.
Fang H., et al., "Rapid Screening and Identification of Methicillin-Resistant Staphylococcus Aureus from Clinical Samples by Selective-Broth and Real-Time PCR Assay," Journal of Clinical Microbiology, 2003, vol. 41 (7), pp. 2894-2899.
Farlow J., et al., "Francisella Tularensis Strain Typing Using Multiple-Locus, Variable-Number Tandem Repeat Analysis," Journal of Critical Microbiology, 2001, vol. 39 (9), pp. 3186-3192.
Farrell D. J., "The Reliability of Microscan Conventional and Rapid Panels to Identify Staphylococcus Aureus and Detect Methicillin Resistance: An Evaluation Using the Tube Coagulase Test and mecA PCR," Pathology, 1997, vol. 29 (4), pp. 406-410.
Fedele C.G., et al., "Multiplex Polymerase Chain Reaction for the Simultaneous Detection and Typing of Polyomavirus JC, BK and SV40 DNA in Clinical Samples," Journal of Virological Methods, 1999, vol. 82 (2), pp. 137-144.
Fedele C.G., et al., "Quantitation of Polyomavirus DNA by a Competitive Nested Polymerase Chain Reaction," Journal of Virological Methods, 2000, vol. 88 (1), pp. 51-61.
Feng P., "Impact of Molecular Biology on the Detection of Food Pathogens," Molecular Biotechnology, 1997, vol. 7 (3), pp. 267-278.
Final Office Action mailed Aug. 6, 2010 for U.S. Appl. No. 11/929,910 filed Oct. 30, 2007.
Final Office Action mailed Jul. 8, 2010 for U.S. Appl. No. 12/326,800 filed Dec. 2, 2008.
Final Office Action mailed May 12, 2010 for U.S. Appl. No. 11/674,538 filed Feb. 13, 2007.
Final Office Action mailed Nov. 17, 2009 for U.S. Appl. No. 11/582,875 filed Oct. 17, 2006.
Final Office Action mailed Feb. 18, 2010 for U.S. Appl. No. 10/754,415 filed Jan. 9, 2004.
Final Office Action mailed Nov. 20, 2009 for U.S. Appl. No. 11/331,987 filed Jan. 13, 2006.
Final Office Action mailed Jul. 23, 2009 for U.S. Appl. No. 11/070,632 filed Mar. 2, 2005.
Final Office Action mailed Jun. 23, 2010 for U.S. Appl. No. 11/930,017 filed Oct. 30, 2007.
Final Office Action mailed Feb. 26, 2009 for U.S. Appl. No. 11/582,863 filed Oct. 17, 2006.
Final Office Action mailed Jan. 30, 2009 for U.S. Appl. No. 10/844,938 filed May 12, 2004.
Final Office Action mailed Jun. 30, 2008 for U.S. Appl. No. 11/070,632 filed Mar. 2, 2005.
Final Rejection mailed Oct. 14, 2009 for U.S. Appl. No. 10/943,344 filed Sep. 17, 2004.
Fong W.K., et al., "Rapid Solid-Phase Immunoassay for Detection of Methicillin-ResistantStaphylococcus Aureus Using Cycling Probe Technology," Journal of Clinical Microbiology, 2000, vol. 38 (7), pp. 2525-2529.
Fox J.P., et al., "The Virus Watch Program: A Continuing Surveillance of Viral Infections in Metropolitan New York Families," American Journal of Epidemiology, 1969, vol. 89 (1), pp. 25-50.
Francois J-C., et al., "Sequence-Specific Recognition and Cleavage of Duplex DNA via Triple-Helix Formation by Oligonucleotides Covalently Linked to a Phenanthroline-Copper Chelate," Proceedings of the National Academy of Sciences of USA, 1989, vol. 86 (24), pp. 9702-9706.
Francois P., et al., "Rapid Detection of Methicillin-Resistant Staphylococcus Aureus Directly from Sterile or Nonsterile Clinical Samples by a New Molecular Assay," Journal of Clinical Microbiology, 2003, vol. 41 (1), pp. 254-260.
Freiberg C., et al., "Genome-Wide mRNA Profiling: Impact on Compound Evaluation and Target Identification in Anti-Bacterial Research," Targets, 2002, vol. 1 (1), pp. 20-29.
Freymuth F., et al., "Comparison of Multiplex PCR Assays and Conventional Techniques for the Diagnostic of Respiratory Virus Infections in Children Admitted to Hospital With an Acute Respiratory Illness," Journal of Medical Virology, 2006, vol. 78 (11), pp. 1498-1504.
Freymuth F., et al., "Detection of Respiratory Syncytial Virus, Parainfluenzavirus 3, Adenovirus Andrhinovirus Sequences in Respiratory Tract of Infants by Polymerase Chain Reaction and Hybridization," Clinical and Diagnostic Virology, 1997, vol. 8 (1), pp. 31-40.

Fujimoto T., et al., "Single-Tube Multiplex. PCR for Rapid and Sensitive Diagnosis of Subgenus B and Other Subgenera Adenoviruses in Clinical Samples," Microbiology and Immunology, 2000, vol. 44 (10), pp. 821-826.
Fujimura S., et al., "Characterization of the mupA Gene in Strains of Methicillin-Resistant *Staphylococcus aureus* with a Low Level of Resistance to Mupirocin," Antimicrobial Agents and Chemotheraphy, 2001, vol. 45 (2), pp. 641-642.
Fujimura S., et al., "Isoleucyl-tRNA Synthetase Mutations in Staphylococcus Aureus Clinicallsolates and In Vitro Selection of Low-Level Mupirocin-Resistant Strains," Antimicrobial Agents and Chemotheraphy, 2003, vol. 47 (10), pp. 3373-3374.
Gall J. G. D., et al., "Construction and Characterization of Hexon-Chimeric Adenoviruses: Specification of Adenovirus Serotype," Journal of Virology, 1998, vol. 72 (12), pp. 10260-10264.
Gammelin M., et al., "Two Subtypes of Nucleoproteins (NP) of Influenza A Viruses," Virology, 1989, vol. 170 (1), pp. 71-80.
Garcia S., et al., "Quantitative Real-Time PCR Detection of Rift Valley Fever Virus and Its Application to Evaluation of Antiviral Compounds," Journal of Clinical Microbiology, 2001, vol. 39 (12), pp. 4456-4461.
Garcia-Martinez J., et al., "Use of the 16s-23s Ribosomal Genes Spacer Region in Studies of Prokaryotic Diversity," Journal of Microbiological Methods, 1999, vol. 36 (1-2), pp. 55-64.
Gaydos C.A., et al., "Adenovirus Vaccines in the U.S. Military," Military Medicine, 1995, vol. 160 (6), pp. 300-304.
Geha D.J., et al., "Multiplex PCR for Identification of Methicillin-Resistant Staphylococci in the Clinical Laboratory," Journal of Clinical Microbiology, 1994, vol. 32 (7), pp. 1768-1772.
Genbank, "{Deletion 6} [Human, Muscle, Mitochondrial Mutant, 22 nt, Segment 2 of 2]," Accession No. S90302.1, Jun. 10, 1992.
Genbank "Acinetobacter genomosp. 10 strain CIP 70.12 RNA polymerase subunit B (rpoB) gene, complete cds," Accession No. 78099429, Mar. 11, 2006.
Genbank, "Bovine parainfluenza virus 3 strain Shipping Fever, complete genome," Accesion No. AF178655, Sep. 19, 2000.
Genbank, "Clostridium tetani E88, complete genome," Accession No. AE015927.1, Feb. 4, 2003.
Genbank "E. coli operon rpoBC coding for the beta- and beta'-subunits of RNA polymerase (genes rpoC and rpoB), and genes rplL, rlpJ, rplA, and rplK coding for 50S ribosomal subunit proteins L7/L12, L10, L1, and L11, respectively. (Map position 89-90 min.)," Accession No. 42813, Feb. 28, 1992.
Genbank, "E.coli 16S ribosomal RNA," Accession No. 174375, Aug. 11, 1995.
Genbank, "E.coli Open Reading Frame Upstream of Leu Operon," Accession No. M21150, Sep. 15, 1990.
Genbank "E.coli rRNA operon (rrnB) coding for Glu-tRNA-2, 5S, 16S and 23S rRNA," Accession No. 147581, Sep. 14, 1992 .
Genbank, "*Enterococcus malodoratus* strain ATCC43197 elongation factor Tu (tufA) gene, partial cds," Accession No. AF274728, Dec. 11, 2000.
Genbank "Escherichia Coli str. K-12 substr. MG1655, Complete Genome," Accession No. NC000913, Oct. 15, 2001.
Genbank, "Homo Sapiens Haplotype V Mitochondrion, Complete Genome", Accession No. AF381990.1, Dec. 28, 2001.
Genbank, "Human Adenovirus Type 4 Hexon Gene," for Accession No. X84646, Jun. 30, 1995.
Genbank, "Human coronavirus 229E, complete genome," Accession No. AF304460, Jul. 11,2001.
Genbank, "Human Isolate L34 Mitochondrion D-loop Region", Accession No. U08081.1, Aug. 16, 1994.
GenBank, "il11b08.y1 Human insulinoma Homo sapiens cDNA clone Image:6029534 5- similar to SW:COX3_HUMAN P00414 Cytochrome C Oxidase Polypeptide III;, mRNA sequence", Accession No. BQ581956.1, Jun. 20, 2002.
Genbank, "Influenza B Virus B/Panama/45/90 Polymerase (PB2) mRNA, Complete Cds", Accession No. AF005737, pp. 1-3, Oct. 4, 1997.
Genbank, "Mastadenovirus h7 hexon gene," Accession No. Z48571, Apr. 18, 2005.
GenBank, "or72a01.s1 NCI_CGAP_Lu5 Homo sapiens cDNA Clone Image:1601352 3— similar to Sw:COX1_HUMAN P00395 Cytochrome C Oxidase Polypeptide I ;, mRNA sequence", Accession No. A1002209.1, Jun. 10, 1998.
Genbank "*Staphylococcus aureus* RN4220 ErmC gene, partial cds," Accession No. 18542231, Sep. 16, 2003.
Genbank "Staphylococcus Aureus Strain MSSA476, Complete Genome," Accession No. BX571857.1, Jun. 24, 2004.
Genbank, "*Staphylococcus aureus* subsp. aureus Mu50, complete genome," Accession No. 15922990, Oct. 4, 2001.
Genbank "Staphylococcus Aureus Subsp. Aureus MW2, Complete Genome," Accession No. 21281729, May 31, 2002.
Genbank, "*Staphylococcus epidermidis* ATCC 12228, complete genome," Accession No. AE015929.1, Jan. 2, 2003.
Genbank "*Streptococcus agalactiae* 2603V/R, complete genome," Accession No. AE009948.1, Aug. 28, 2002.
Genbank, "Streptococcus Anginosus Elongation Factor Tu (tuf) Gene, Partial cds," Accession No. AF276257.1, Jul. 1, 2001.
Genbank "*Streptococcus pneumoniae* isolate 95.11nOOS DNA gyrase subunit B (gyrB) gene, complete cds," Accession No. 73916349, Sep. 30, 2005.
Genbank, "*Streptococcus pyogenes* strain MGAS8232, complete genome," Accession No. AE009949.1, Apr. 3, 2002.
Genbank, "*Venezuelan equine encephalitis* virus nonstructural polyprotein and structural polyprotein genes, complete cds," Accession No. AF375051.1, Jun. 26, 2001.
Gendel S.M., "Computational Analysis of the Specificity of 16S rRNA-Derived Signature Sequencesfor Identifying Food-Related Microbes," Food Microbiology, 1996, vol. 13, pp. 1-15.
Gibb T.R., et al., "Development and Evaluation of a 5 Fluorogenic Nuclease Assay to Detect and Differentiate Between Ebola Virus Subtypes Zaire and Sudan," Journal of Clinical Microbiology, 2001, vol. 39 (11), pp. 4125-4130.
Gilbert N., et al., "Comparison of Commercial Assays for the Quantitation of HBV DNA Load in Healthcare Workers: Calibration Differences," Journal of Virological Methods, 2002, vol. 100 (1-2), pp. 37-47.
Gill S.R., et al., "Insights on Evolution of Virulence and Resistance from the Complete Genome Analysis of an Early Methicillin-Resistant Staphylococcus Aureus Strain and a Biofilm-Producing Methicillin-Resistant Staphylococcus Epidemidis Strain," Journal of Bacteriology, 2005, vol. 187(7), pp. 2426-2438.
Gilliland G., et al., "Analysis of Cytokine mRNA and DNA: Detection and Quantitation by Competitive Polymerase Chain Reaction," Proceedings of the National Academy of Sciences of USA, 1990, vol. 87 (7), pp. 2725-2729.
Gjoen K.V., et al., "Specific Detection of Coxsackie Viruses A by the Polymerase Chain Reaction," Clinical and Diagnostic Virology, 1997, vol. 8 (3), pp. 183-188.
Golden M. R., et al., "Pilot Study of COBAS PCR and Ligase Chain Reaction for Detection of Rectal Infections Due to *Chlamydia trachomatis*," Journal of Clinical Microbiology, 2003, vol. 41 (5), pp. 2174-2175.
Gravet A., et al., "Characterization of a Novel Structural Member, LukE-LukD, of the Bi-Component Staphylococcal Leucotoxins Family," FEBS Letters, 1998, vol. 436 (2), pp. 202-208.
Gray G.C., et al., "Adult Adenovirus Infections: Loss of Orphaned Vaccines Precipitates Military Respiratory Disease Epidemics," Clinical Infectious Diseases, 2000, vol. 31, pp. 663-670.
Grondahl B., et al., "Rapid Identification of Nine Microorganisms Causing Acute Respiratory TractInfections by Single-Tube Multiplex Reverse Transcription-PCR: Feasibility Study," Journal of Clinical Microbiology, 1999, vol. 37 (1), pp. 1-7.
Grundmann H., et al., "Emergence and Resurgence of Meticillin-Resistant Staphylococcus Aureus as a Public-Health Threat," Lancet, 2006, vol. 368 (9538), pp. 874-885.
Gu Z., et al., "Multiplexed, Real-Time PCR for Quantitative Detection of Human Adenovirus," Journal of Clinical Microboilogy, 2003, vol. 41 (10), pp. 4636-4641.
Guatelli J.C., et al., "Nucleic Acid Amplification In Vitro: Detection of Sequences with Low Copy Numbers and Application to Diagnosis of Human Immunodeficiency Virus Type 1 Infection," Clinical Microbiology Reviews, 1989, vol. 2 (2), pp. 217-226.

Haff L.A., et al., "Multiplex Genotyping of PCR Products with Mass Tag-Labeled Primers," Nucleic Acids Research, 1997, vol. 25 (18), pp. 3749-3750.
Haines J.D., et al., "Medical Response to Bioterrorism: Are we Prepared," Journal of Oklahoma State Medical Association, 2000, vol. 93, pp. 187-196.
Hamdad F., et al., "Detection of Methicillin/Oxacillin Resistance and Typing in Aminoglycoside-Susceptible Methicillin-Resistant and Kanamycin-Tobramycin-Resistant Methicillin-Susceptible," Microbial Drug Resistance, 2006, vol. 12 (3), pp. 177-185.
Hamel S., et al., "Consensus PCR and Microarray for Diagnosis of the Genus Staphylococcus, Species, and Methicillin Resistance," Biotechniques, 2001, vol. 31 (6), pp. 1364-1372.
Hammerle T., et al., "A Sensitive PCR Assay System for the Quantitation of Viral Genome Equivalents:Hepatitis C Virus (HCV)," Archives of Virology, 1996, vol. 141 (11), pp. 2103-2114.
Hannis J.C., et al., "Nanoelectrospray Mass Spectrometry Using Non-Metalized, Tapered (50-10 .mu.m) Fused-silica Capillaries," Rapid Communication in Mass spectrometry, 1998, vol. 12, pp. 443-448.
Hanssen A.M., et al., "Sccmecin Staphylococci: Genes on the Move," FEMS Immuol Medical Microbiol, 2006, vol. 46, pp. 8-20.
Hasebe F. et al., "Combined Detection and Genotyping of Chikungunya Virus by a Specific Reverse Transcription-Polymerase Chain Reaction," Journal of Medical Virology, 2002, vol. 67 (3), pp. 370-374.
Hassan A.A., et al., "Inter— and Intraspecies Variations of the 16S-23S rDNA Intergenic Spacer Region of Various Streptococcal Species," Systematic and Applied Microbiology, 2003, vol. 26 (1), pp. 97-103.
He L., et al, "Development of a Capillary High-performance Liquid Chromatography Tandem Mass Spectrometry System Using SWIFT Technology in an Ion Trap/Reflectron Time-of-flight Mass Spetrometer," Biochemical and Biophysical Research Communications, 1997, vol. 11, pp. 1739-1748.
Heim A., et al., "Rapid and Quantitative Detection of Human Adenovirus DNA by Real-Time PCR," Journal of Medical Viral, 2003, vol. 70, pp. 228-239.
Higgins J.A., et al., "Sensitive and Rapid Identification of Biological Threat Agents," Annals of the New York Academy of Sciences, 1999, vol. 894, pp. 130-148.
Hill F., et al., "Polymerase Recognition of Synthetic Oligodeoxyribonucleotides Incorporating Degenerate Pyrimidine and Purine Bases," Proceedings of the National Academy of Sciences, 1998, vol. 95, pp. 4258-4263.
Hiramatsu K., et al., "The Emergence and Evolution of Methicillin-Resistant Staphylococcusaures," Trends Microbiology, 2001, vol. 9 (10), pp. 486-493.
Hodgson J.E., et al., "Molecular Characterization of the Gene Encoding High-Level Mupirocin Resistancein *Staphylococcus aureus* J2870," Antimicrobial Agents and Chemotherapy, 1994, vol. 38 (5), pp. 1205-1208.
Hoffman E., et al., "Rescue of Influenza B Virus from Eight Plasmids," Proceedings of the National Academy of Sciences, 2002, vol. 99 (17), pp. 11411-11416.
Hofstadler S.A., et al., "TIGER: The Universal Biosensor," International Journal of Mass Spectrometry, 2005, vol. 242, pp. 23-41.
Holden M.T., et al., "Complete Genomes of Two Clinical Staphylocuccus Aureus Strain: Evidence for the Rapid Evolution of Virulence and Drug Resistance," Proceedings of the National Academy of Sciences, 2004, vol. 101 (26), pp. 9786-9791.
Holland M.M., et al., "Mitochondrial DNA Sequence Analsysis—Validation and Use for Forensic Casework," Forensic Science Review, 1999, vol. 11 (1), pp. 22-50.
Holmes E.C., et al., "Whole-Genome Analysis of Human Influenza A Virus Reveals Multiple Persistent Lineages and Reassortment among Recent H3N2 Viruses," Public Library of Science Biology, 2005, vol. 3 (9), pp. 1579-1589.
Hongoh Y., et al., "Evaluation of Primers and PCR Conditions for the Analysis of 16s rRNA Genes from a Naturalenvironment," FEMS Microbiology Letters, 2003, vol. 221 (2), pp. 299-304.
Hood E., et al., "Chemical and Biological Weapons: New Questions, New Answers," Environmental Health Perspectives, 1999, vol. 107 (12), pp. 931-932.
Houng H.S., et al., "Rapid Type-Specific Diagnosis of Adenovirus Type 4 Infection Using a Hexon- Based Quantitative Fluorogenic Pcr," Diagnostic Microbiology and Infectious Disease, 2002, vol. 42 (4), pp. 227-236.
Huber C.G., et al., "On-Line Cation Exchange for Suppression of Adduct Formation in Negative-Ion Electrospray Mass Spectrometry of Nucleic Acids," Analytical Chemistry, 1998, vol. 70 (24), pp. 5288-5295.
Huletsky A., et al., "New Real-Time Pcr Assay for Rapid Detection of Methicillin-Resistantstaphylococcus Aureus Directly from Specimens Containing a Mixture of Staphylococci," Journal of Clinical Microbiology, 2004, vol. 42 (5), pp. 1875-1884.
Hunag C., et al., "Detection of Arboviral RNA Directly from Mosquito Homogenates by Reverse Transcription-Polymerase Chain Reaction," Journal of Virological Methods, 2001, vol. 94 (1-2), pp. 121-128.
Hung E.C., et al., "Detection of SARS coronavirus RNA in the cerebrospinal fluid of a patient with severe acute respiratory syndrome," Clinical Chemistry, 2003, vol. 49 (12), pp. 2108-2109.
Hurdle J.G., et al., "Analysis of Mupirocin Resistance and Fitness in *Staphylococcus aureus* by Molecular Genetic and Structural Modeling Techniques," Antimicrobial Agents and Chemotherapy, 2004, vol. 48 (11), pp. 4366-4376.
Hyde-Deruyscher R., et al., "Polyomavirus Early-Late Switch is not Regulated at the Level of Transcription Initiation and is associated with changes in RNA Processing," Proceedings of the National Academy of Sciences, 1988, vol. 85, pp. 8993-8997.
Ieven M., et al., "Rapid Detection of Methicillin Resistance in Coagulase-Negative Staphylococci by Commercially Available Fluorescence Test," Journal of Clinical Microbiology, 1995, vol. 33 (8), pp. 2183-2185.
Ihle O., et al., "Efficient Purification of DNA Fragments using a Protein Binding Membrane," Nucleic Acids Research, 2000, vol. 28 (16), pp. e76.
Inglis T.J., et al., "Rapid Genotypic Confirmation of Methicillin Resistance," Pathology, , 1996, vol. 28 (3), pp. 259-261.
International Preliminary Examination Report and Written Opinion for Application No. PCT/US2005/00386, mailed on May 9, 2006, 6 pages.
International Preliminary Examination Report for Application No. PCT/US2002/06763, mailed on Jun. 11, 2003, 6 pages.
International Preliminary Examination Report for Application No. PCT/US2003/09802, mailed on Apr. 8, 2005, 7 pages.
International Preliminary Examination Report for Application No. PCT/US2003/22835, mailed on Mar. 5, 2005, 4 pages.
International Preliminary Examination Report for Application No. PCT/US2003/38505, mailed on Mar. 3, 2006, 5 pages.
International Preliminary Examination Report for Application No. PCT/US2003/38757, mailed on Feb. 2, 2007, 5 pages.
International Preliminary Examination Report for Application No. PCT/US2003/38761, mailed on Jun. 27, 2006, 6 pages.
International Preliminary Report on Patentability and Written Opinion for Application No. PCT/US2005/030058, mailed on Aug. 20, 2007, 6 pages.
International Preliminary Report on Patentability and Written Opinion for Application No. PCT/US2005/033707, mailed on Mar. 20, 2007, 6 pages.
International Preliminary Report on Patentability for Application No. PCT/US2004/033742, mailed on Jun. 20, 2006, 1 page.
International Preliminary Report on Patentability for Application No. PCT/US2006/028397, mailed on Jan. 22, 2008, 1 page.
International Preliminary Report on Patentability for Application No. PCT/US2008/054926, mailed on Aug. 26, 2009 , 1 page.
International Preliminary Report on Patentability, Written Opinion and International Search Report for Application No. PCT/US2004/015123, mailed on Oct. 3, 2005, 8 pages.
International Search Report and Written Opinion for Application No. PCT/US2006/007747, mailed on Sep. 5, 2006, 13 pages.
International Search Report and Written Opinion for Application No. PCT/US2006/015160, mailed on Oct. 10, 2006, 13 pages.

International Search Report and Written Opinion for Application No. PCT/US2006/028397, mailed on Mar. 5, 2007, 14 pages.
International Search Report and Written Opinion for Application No. PCT/US2006/040747, mailed on Mar. 17, 2009, 19 pages.
International Search Report and Written Opinion for Application No. PCT/US2006/061307, mailed on Jan. 9, 2008, 21 pages.
International Search Report and Written Opinion for Application No. PCT/US2007/20045 mailed on Jan. 9, 2009, 18 pages.
International Search Report and Written Opinion for Application No. PCT/US2008/054926, mailed on Jan. 26, 2009, 15 pages.
International Search Report and Written Opinion for Application No. PCT/US2008/057717, mailed on Jan. 13, 2009, 18 pages.
International Search Report and Written Opinion for Application No. PCT/US2008/057901, mailed on Aug. 28, 2008, 14 pages.
International Search Report for Application No. PCT/US2002/06763, mailed on Oct. 23, 2002, 4 pages.
International Search Report for Application No. PCT/US2003/009802, mailed on Aug. 3, 2004, 2 pages.
International Search Report for Application No. PCT/US2003/038505 mailed on Apr. 12, 2005.
International Search Report for Application No. PCT/US2003/22835, mailed on Dec. 12, 2003, 1 page.
International Search Report for Application No. PCT/US2004/012671, mailed on Sep. 28, 2007, 2 pages.
International Search Report for Application No. PCT/US2004/015123, mailed on Oct. 3, 2005, 2 pages.
International Search Report for Application No. PCT/US2004/015196, mailed on Jul. 1, 2005, 3 pages.
International Search Report for Application No. PCT/US2004/028869, mailed on Jul. 17, 2006, 4 pages.
International Search Report for Application No. PCT/US2004/033742, mailed on May 15, 2006, 2 pages.
International Search Report for Application No. PCT/US2005/005356, mailed on Aug. 7, 2007, 5 pages.
International Search Report for Application No. PCT/US2005/006133, mailed on Jul. 26, 2007, 4 pages.
International Search Report for Application No. PCT/US2005/007022, mailed on Oct. 20, 2006, 1 page.
International Search Report for Application No. PCT/US2005/009557, mailed on Sep. 19, 2005, 1 page.
International Search Report for Application No. PCT/US2005/018337, mailed on Oct. 10, 2006, 2 pages.
International Search Report for Application No. PCT/US2005/024799, mailed on Dec. 28, 2006, 4 pages.
International Search Report for Application No. PCT/US2005/030058, mailed on Aug. 4, 2007, 1 page.
International Search Report for Application No. PCT/US2005/033707, mailed on Feb. 6, 2006, 3 pages.
International Search Report for Application No. PCT/US2007/066194, mailed on Jan. 15, 2008, 5 pages.
International Search Report for Application No. PCT/US2007/087091, mailed on Jan. 15, 2008, 13 pages.
International Search Report for Application No. PCT/US2008/057901, mailed on Jun. 29, 2009, 15 pages.
International Search Report for Application No. PCT/US2008/064891, mailed on Aug. 28, 2008.
International Search Report for Application No. PCT/US2008/065332, mailed on Nov. 28, 2008, 5 pages.
International Search Report for Application No. PCT/US2009/045635, mailed on Oct. 7, 2009, 9 pages.
International Search Report for Application No. PCT/US04/007236, mailed on Feb. 24, 2006, 3 pages.
Interview Summary Report mailed May 19, 2003 for U.S. Appl. No. 09/891,793 filed Jun. 26, 2001.
Inyaku K., et al., "Rapid Detection and Identification of Mycobacteria in Sputum Samples by NestedPolymerase Chain Reaction and Restriction Fragment Length Polymorphisms of dnaJ Heat ShockProtein Gene," Journal of Medical Sciences, 1993, vol. 42 (1), pp. 21-31.
Iqbal S.S., et al., "A Review of Molecular Recognition Technologies for Detection of Biological Threat Agents," Biosensors & Bioelectronics, 2000, vol. 15 (11-12), pp. 549- 578.
Iteman I., et al., "Comparison of Conserved Structural and Regulatory Domains within Divergent 16S rRNA-235 rRNA Spacer Sequences of Cyanobacteria," Microbiology, vol. 146 (Pt 6), pp. 1275-1286.
Ito T., et al., "Insights on Antibiotic Resistance of Staphylococcus Aureus from its Whole Genome: Genomic Island Scc," Drug Resistance Updates, 2003, vol. 6 (1), pp. 41-52.
Ito T., et al., "Structural Comparison of Three Types of Staphylococcal Cassette Chromosome mecIntegrated in the Chromosome in Methicillin-Resistant *Staphylococcus aureus*, " Antimicrobial Agents and chemotherapy, 2001, vol. 45 (5), pp. 1323-1336.
Jackson P.E., et al., "Mass Spectrometry for Genotyping: an Emerging Tool for Molecular Medicine," Molecular Medicine Today, 2000, vol. 6 (7), pp. 271-276.
James A.M., et al., "Borelia Lonestari Infection after a Bite by an Amblyomma Americanum Tick," The Journal of Infectious Diseases, 2001, vol. 183 (12), pp. 1810-1814.
Jaulhac B., et al., "Specific Detection of the Toxic Shock Syndrome Toxin-1 Gene Using the Polymerase Chain Reaction," Molecular and Cellular Probes, 1991, vol. 5, pp. 281-284.
Jaulhac B., et al., "Synthetic DNA Probes for Detection of Genes for Enterotoxins A, B, C, D, E and for Tsst-1 in Staphylococcal Strains," Journal of Applied Bacterial, 1992, vol. 72 (5), pp. 386-392.
Jeong J., et al., "Early Screening of Oxacillin-Resistant Staphylococcus Aureus and Staphylococcus Epidermidis From Blood Culture," Journal of Korean Medical Science, 2002, vol. 17, pp. 168-172.
Johansson A., et al., "Evaluation of PCR-based Methods for Discrimination of Francisella species and Subspecies and Development of a Specific PCR that Distinguishes the two Major Subspecies of Francisella Tularensis," Journal of Clinical Microbiology, 2000, vol. 38 (11), pp. 4180-4185.
Johnson W.M., et al., "Detection of Genes for Enterotoxins, Exfoliative Toxins, and Toxic Shock Syndrome Toxin 1 in Staphylococcus Aureus by the Polymerase Chain Reaction," Journal of Clinical Microbiology, 1991, vol. 29 (3), pp. 426-430.
Jonas D., et al., "Rapid PCR-Based Identification of Methicillin-Resistant *Staphylococcus aureus*from Screening Swabs," Journal of Clinical Microbiology, 2002, vol. 40 (5), pp. 1821-1823.
Jurinke C., et al., "Application of Nested PCR and Mass Spectrometry for DNA Based Virus Detection: HBV-DNA Detected in the Majority of Isolated Anti-Hbc Positive Sera," Genetic Analysis: Biomolecular Engineering, 1998, vol. 14 (3), pp. 97-102.
Jurinke C., et al., "MALDI-TOF Mass Spectrometry. A Versatile Tool for High-Performance DNA Analysis," Molecular Biotechnology, 2004, vol. 26 (2), pp. 147-163.
Kacian D.L., et al., "A Replicating RNA Molecule Suitable for a Detailed Analysis of Extracellular Evolution and Replication," Proceeding of the National Academy of Sciences, 1972, vol. 69 (10), pp. 3038-3042.
Kajon A.E., et al., "Genome Type Analysis of Brazilian Adenovirus Strains of Serotypes 1, 2, 3, 5,and 7 Collected Between 1976 and 1995," Journal of Medical, 1999, vol. 58 (4), pp. 408-412.
Kasai H., et al., "Construction of the gyrB Database for the Identification and Classification of Bacteria," Genome Informatics. Workshop on Genome Informatics, 1998, pp. 13-21.
Katano H., et al., "Identification of Adeno-Associated Virus Contamination In Cell And Virus Stocks by PCR," Biotechniques, 2004, vol. 36 (4), pp. 676-680.
Katayama Y., et al., "Genetic Organization of the Chromosome Region Surrounding mecA inClinical Staphylococcal Strains: Role of IS431 -Mediated mecI Deletion in Expression of Resistance inmed-Canying, Low-Level Methicillin-Resistant *Staphylococcus haemolyticus*," Antimicrobial Agents and Chemotherapy, 2001, vol. 45 (7), pp. 1955-1963.
Kearns A.M., et al., "Rapid Detection of Methicillin-Resistant Staphylococci by Multiplex PCR," The Journal of Hospital Inspection 1999, vol. 43 (1), pp. 33-37.
Khan A.S., et al., "An Outbreak of Crimean-Congo Haemorrhagic Fever in the United Arab Emirates, 1994-1995," The American Journal of Tropical Medicine and Hygiene, 1997, vol. 57 (5), pp. 519-525.

Khan S.A., et al., "Simultaneous Detection of Erythromycin-Resistant Methylase Genes ermA and ermC from Staphylococcus Spp. By Multiplex-PCR," Molecular and Cellular Probes, 1999, vol. 13 (5), pp. 381-387.
Kidd A.H., et al., "Rapid Subgenus Identification of Human Adenovirus Isolates by a General PCR," Journal of Clinical Microbiology, 1996, vol. 34 (3), pp. 622-627.
Kidd-Ljunggren K., et al., "The hepatitis B virus X gene: analysis of functional domain variation and gene phylogeny using multiple sequences," Journal of General Virology, 1995, vol. 76 (pt 9), pp. 2119-2130.
Kikuchi K., et al., "Restriction Fragment Length Polymorphism Analysis of Clinical Isolates of Mycobacterium Haemophilum," Journal of Clinical Microbiology, vol. 32 (7), pp. 1763-1767.
Kilbourne E.D., "Influenza Pandemics of the 20th Century," Emerging Infectious Diseases Journal, 2006, vol. 12 (1), pp. 9-14.
Kilbourne E.D., "Influenza Pandemics: Can We Prepare for the Unpredictable," Viral Immunology, 2004, vol. 17 (3), pp. 350-357.
Kim B.J., et al., "Identification of Mycobacterial Species by Comparative Sequence Analysis of the RNA Polymerase Gene (rpoB)," Journal of Clinical Microbiology, 1999, vol. 37 (6), pp. 1714-1720.
Kinney R.M., et al., "Nucleotide Sequences of the 26S mRNAs of the Viruses Defining the Venezuelan Equine Encephalitis Antigenic Complex," The American Journal of Tropical Medicine and Hygiene, 1998, vol. 59 (6), pp. 952-964.
Kirpekar F., et al., "Matrix Assisted Laser Desorption/Ionization Mass Spectrometry of Enzymatically Synthesized RNA up to 150 kDa," Nucleic Acids Research, vol. 22 (19), pp. 3866-3870.
Kitagawa Y., et al., "Rapid Diagnosis of Methicillin-Resistant Staphylococcus Aureus Bacteremia by Nested Polymerase Chain Reaction," Annals of Surgery, 1996, vol. 224 (5), pp. 665-671.
Knoth K., et al., "Highly Degenerate, Inosine-Containing Primers Specifically Amplify Rare cDNA using the Polymerase Chain Reaction," Nucleic Acids Research, 1988, vol. 16 (22), pp. 10932.
Kolbert C.P., et al., "Branched-DNA Assay for Detection of the mecA Gene in Oxacillin-Resistant and Oxacillin-Sensitive Staphylococci," Journal of Clinical Microbiology, 1998, vol. 36 (9), pp. 2640-2644.
Kowalak J.A., et al., "A Novel Method for the Determination of Post-Transcriptional Modification in RNA by Mass Spectrometry," Nucleic Acids Research, 1993, vol. 21 (19), pp. 4577-4585.
Krafft A.E., et al., "Evaluation of PCR Testing of Ethanol-Fixed Nasal Swab Specimens as anAugmented Surveillance Strategy for Influenza Virus and Adenovirus Identification," Journal of Clincal Microbiology, 2005, vol. 43 (4), pp. 1768-1775.
Kramer L.D., et al., "Dection of Encephalitis Viruses in Mosquitoes (Diptera: Culicidea) and Avian Tissues," Journal of Medical Entomology, 2002, vol. 39 (2), pp. 312-323.
Kramer L.D., et al., "Dection of St. Louis Encephalitis and Western Equine Encephalomyelitis RNAin Mosquitoes Tested Without Maintainance of a Cold Chain," Journal of the American Mosquito Control Association, 2001, vol. 17 (4), pp. 213-215.
Kresken M., et al., "Prevalence of Mupirocin Resistance in Clinical Isolates of Staphylococccus Aureus and Staphylococcus Epidermidis: Results of the Antimicrobial Resistance Surveillance Study of the Paul-Ehrlich-Society for Chemotherapy, 2001," International Journal of Antimicrobial Agents, 2004, vol. 23 (6), pp. 577-581.
Krishnan P.U., et al., "Detection of Methicillin and Mupirocin Resistance in Staphylococcus Aureusisolates Using Conventional and Molecular Methods: A Descriptive Study from a Burns Unit with Highprevalence of MRSA," Journal of Clinical Pathology, 2002, vol. 55 (10), pp. 745-748.
Kroes I., et al., "Bacterial Diversity Within the Human Subgingival Crevice," Proceeding of the National Academy of Sciences, 1999, vol. 96 (25), pp. 14547-14552.
Krossoy B., et al., "The Putative Polymerase Sequence of Infectious Salmon Anemia Virus Suggests a New Genus within the Orthomyxoviridae," Journal of Virology, 1999, vol. 73 (3), pp. 2136-2142.
Ksiaxek T.G., et al., "A Novel Coronavirus Associated with Severe Acute Respiratory Syndrome," The New England Journal of Medicine, 2003, vol. 348 (20), pp. 1953-1966.
Kuroda M., et al., "Whole Genome Sequencing of Meticillin-Resistant Staphylococcus Aureus," The Lancet, 2001, vol. 357 (9264), pp. 1225-1240.
Kwok S., et al., "Avoiding False Positives with PCR," Nature, 1989, vol. 339 (6221), pp. 237-238.
Labandeira-Rey, M. et al., "*Staphylococcus aureus* Panton Valentine Leukocidin CausesNecrotizing Pneumonia," Sciencexpress, 2007, pp. 1-8.
Lacroix L., et al., "Triplex Formation by Oligonucleotides Containing 5-(1-Propynyl)-2-deoxyuridine: Decreased Magnesium Dependence and Improved Intracellular Gene Targeting," Biochemistry, 1999, vol. 38 (6), pp. 1893-1901.
Laken S.J., et al., "Genotyping by Mass Spectrometric Analysis of Short DNA Fragments," Nature Biotechnology, 1998, vol. 16 (13), pp. 1352-1356.
Lamb R.A., et al., "Sequence of Interrupted and Uninterrupted mRNAs and Cloned DNA Coding for the Two Overlapping Nonstructural Proteins of Influenza Virus," Cell, 1980, vol. 21 (2), pp. 475-485.
Lambert A.J., et al., "Detection of North American Eastern and Western Equine EncephalitisViruses by Nucleic Acid Amplification Assays," Journal of Clinical Microbiology, 2003, vol. 41 (1), pp. 379-385.
Lau L.T., et al, "A Real-Time PCR for SARS-Coronavirus Incorporating Target Gene Pre-Amplification," Biochemical and Biophysical Research Communications, 2003, vol. 312 (4), pp. 1290-1296.
Lau L.T., et al., "Nucleic Acid Sequence-Based Amplification Methods to Detect Avian Influenza Virus," Biochemical and Biophysical Research Communications, 2004, vol. 313 (2), pp. 336-342.
Le Cann P., et al., "Quantification of Human Astroviruses in Sewage Using Real-Time RT-PCR," Research in Microbiology, 2004, vol. 155 (1), pp. 11-15.
Lebedev Y., et al., "Oligonucleotides Containing 2-Aminoadenine and 5-Methycytosine are More Effective as Primers for PCR Amplification than their Nonmodified Counterparts," Genetic Analysis: Biomolecular Engineering, 1996, vol. 13 (1), pp. 15-21.
Lednicky J.A., et al., "Polyomaviruses and Human Tumors: A Brief Review of Current Concepts and Interpretations," Frontiers Bioscience, 1999, vol. 4, pp. D153-164.
Lee J.A., et al., "Rapid Identification of Human Adenovirus Types 3 and 7 from Respiratory Specimens via Multiplex Type-Specific PCR," Journal of Clinical Microbiology, 2005, vol. 43 (11), pp. 5509-5514.
Lee J.H., et al., "Simultaneous Detection of Three Mosquito-Borne Encephalitis Viruses (Eastern equine, La Crosse, and St. Louis) with a Single-Tube Multiplex Reverse Transcriptase Polymerase Chaine Reaction Assay," Journal of the American Mosquito Control Association, 2002, vol. 18 (1), pp. 26-31.
Lengyel A., et al., "Characterization of the Main Protein Components of Adenovirus Virion and itsPossible Use in Laboratory Diagnostics," Acta Microbiologica Immunologica Hungarica, 1998, vol. 43 (3-4), pp. 281-283.
Leroy E.M., et al., "Diagnosis of Ebola Haemorrhagic Fever by RT-PCR in an Epidemic Setting," Journal of Medicinal Virology, 2000, vol. 60 (4), pp. 463-467.
Levi K., et al., "Evaluation of an Isothermal Signal Amplification Method for Rapid Detection of Methicillin-Resistant Staphylococcus Aureus from Patient-Screening Swabs," Journal of Clinical Microbiology, 2003, vol. 41 (7), pp. 3187-3191.
Levine S.M., et al., "PCR-Based Detection of Bacillus Anthracis in Formalin-Fixed Tissue from a Patient Receiving Ciprofloxacin," Journal of Clinical Microbiology, 2002, vol. 40 (11), pp. 4360-4362.
Levison P.R., et al., "Recent Developments of Magnetic Beads for Use in Nucleic Acid Purification," Journal of Chromatography, 1998, vol. A816, pp. 107-111.
Li C., et al., "Evolution of H9N2 Influenza Viruses from Domestic Poultry in Mainland China," Virology, 2005, vol. 340 (1), pp. 70-83.
Li Q., et al., "Genetic Variability of Hexon Loops 1 and 2 between Seven Genome Types of Adenovirus Serotype 7," Archives of Virology, 1999, vol. 144 (9), pp. 1739-1749.
Li Q., et al., "Screening of the High Yield Influenza B Virus on MDCK c14d Cloning of its Whole Genome," International Congress Series, 2004, pp. 610-614.

Li Q.G., et al., "Analysis of 15 Different Genome Types of Adenovirus Type 7 Isolated on FiveContinents," Journal of Virology, 1986, vol. 60 (1), pp. 331-335.
Li Q.G., et al., "Comparison of 17 Genome Types of Adenovirus Type 3 Identified among Strains Recovered from Six Continents," Journal of Clinical Microbiology, 1988, vol. 26 (5), pp. 1009-1015.
Liebermann H., et al., "Mapping of Epitopes on the Fiber Knobs of Human Adenovirus Serotypes 8 and 15," Intervirology, 2002, vol. 45 (1), pp. 59-66.
Liebermann H., et al., "Mapping of Linear Epitopes on Fibre Knob of Human Adenovirus Serotype 5," Virus Research, 2001, vol. 73 (2), pp. 145-151.
Lim L.P., et al., "The MicroRNAs of Caenorhabditis Elegans," Genes and Development, 2003, vol. 17 (8), pp. 991-1008.
Limbach P.A., et al., "Enzymatic Sequencing of Oligonucleotides with Electrospray Mass Spectrometry," 42nd ASMS Conference on Mass Spectrometry, 1994.
Limoncu M.H., et al., "Emergence of Phenotypic Resistance to Ciprofloxacin and Levofloxacin Inmethicillin-Resistant and Methicillin-Sensitive Staphylococcus Aureus Strains," International Journal of Antimicrobial Agents, 2003, vol. 21 (5), pp. 420-424.
Lin B., et al., "Use of Oligonucleotide Microarrays for Rapid Detection and Serotyping of Acute Respiratory Disease-Associated Adenoviruses," Journal of Clinical Microbiology, 2004, vol. 42 (7), pp. 3232-3239.
Lin P.H., et al., "Oxidative Damage to Mitochondrial Dna in Atrial Muscle of Patients with Atrial Fibrillation," Free Radical Biology and Medicine, 2003, vol. 35 (10), pp. 1310-1318.
Lina G., et al., "Bacterial Competition for Human Nasal Cavity Colonization: Role of Staphylococcalagr Alleles," Applied and Environmental Microbiology, 2003, vol. 69 (1), pp. 18-23.
Lina G., et al., "Involvement of Panton-Valentine Leukocidin-Producing Staphylococcus Aureus in Primary Skin Infections and Pneumonia," Clinical Infectious Diseases, 1999, vol. 29 (5), pp. 1128-1132.
Linssen B., et al., "Development of Reverse Transcription-PCR Assays Specific for Detection of Equine Encephalitis Viruses," Journal of Clinical Microbiology, 2000, vol. 38 (4), pp. 1527-1535.
Liu J.H., et al., "Interregional Transmission of the Internal Protein Genes of H2 Influenza Virus in Migratory Ducks from North America to Eurasia," Virus Genes, 2004, vol. 29 (1), pp. 81-86.
Livermore D.M., "The Threat from the Pink Corner," Annals of Medicine, 2003, vol. 35 (4), pp. 226-234.
Loo J.A., et al., "Applying Charge Discrimination with Electrospray Ionization-Mass Spectrometry to Protein Analysis," Journal of American Society for Mass Spectrometry, 1995, vol. 6, pp. 1098-1104.
Lott T.J., et al., "Nucleotide Sequence Analysis of the 5-8s rDNA and Adjacent ITS2 Region of Candidaalbicans and Related Species," Yeast, 1993, vol. 9, pp. 1199-1206.
Louie L., et al., "Evaluation of Three Rapid Methods for Detection of Methicillin Resistance in Staphylococcus Aureus," Journal of Clinical Microbiology, 2000, vol. 38 (6), pp. 2170-2173.
Lovseth A., et al., "Modified Multiplex PCR Method for Detection of Pyrogenic Exotoxin Genes in Staphylococcal Isolates," Journal of Clinical Microbiology, 2004, vol. 42 (8), pp. 3869-3872.
Lowe T., et al., "A Computer Program for Selection of Oligonucleotide Primers for Polymerase Chain Reactions," Nucleic Acids Research, 1990, vol. 18 (7), pp. 1757- 761.
Lu X., et al., "Molecular Typing of Human Adenoviruses by PCR and Sequencing of a Partial Region of the Hexon Gene," Archives of Virology, 2006, vol. 151 (8), pp. 1587-1602.
Lubman D.M., Application for Continuation Grant by David Mitchell Lubmann dated Jun. 4, 1996 and Jun. 14, 1996.
Lubman D.M., Application for Continuation Grant by David Mitchell Lubmann dated Jun. 10, 1994 and Jun. 24, 1994.
Lubman D.M., Application for Grant by David Mitchell Lubmann dated Sep. 1, 1994 and Sep. 27, 1994.
Lubman D.M., Application for Grant by David Mitchell Lubmann dated Oct. 25, 1992 and Oct. 29, 1992.
Ludwig S.L., et al., "Prevalence of Antibodies to Adenovirus Serotypes 4 and 7 among Unimmunized US Army Trainees: Results of a Retrospective Nationwide Seroprevalence Survey," The Journal of Infectious Diseases, 1998, vol. 178 (6), pp. 1776-1778.
Ludwig W., et al., "Bacterial Phylogeny Based on 16S and 23S rRNA Sequence Analysis," FEMS Microbiolofy Reviews, 1994, vol. 15 (2-3), pp. 155-173.
Lukashov V.V., et al., "Evolutionary Relationships among Parvoviruses: Virus-Host Coevolution among Autonomous Primate Parvoviruses and Links between Adeno-Associated and Avian Parvoviruses," Journal of Virology, 2001, vol. 75 (6), pp. 2729- 2740.
Ma X.X., et al., "Novel Type of Staphylococcal Cassette Chromosome mec Identified in Community-Acquired Methicillin-Resistant *Staphylococcus aureus* Strains," Antimicrobial Agents and Chemotherapy, 2002, vol. 46 (4), pp. 1147-1152.
Mack D.H., et al., "A Sensitive Method for the Identification of Uncharacterized Viruses Related Toknown Virus Groups: Hepadnavirus Model System," Proceedings of the National Academy of Sciences, 1988, vol. 85 (18), pp. 6977-6981.
Magnuson V.L., et al., "Substrate Nucleotide-Determined Non-Templated Addition of Adenine by TagDNA Polymerase: Implications for PCR-Based Genotyping and Cloning," BioTechniques, 1996, vol. 21 (4), pp. 700-709.
Malasig M.D., et al., "Simplified Microneutralization Test for Serotyping Adenovirus Isolates," Journal of Clinical Microbiology, 2001, vol. 39 (8), pp. 2984-2986.
Manian F.A., "Asymptomatic Nasal Carriage of Mupirocin-Resistant, Methicillin-Resistant *Staphylococcus aureus* (MRSA) in a Pet Dog Associated with MRSA Infection in Household Contacts," Clinical Infectious Diseases, 2003, vol. 36 (2), pp. e26-e28.
Marks F., et al., "Genotyping of Plasmodium Falciparum Pyrimethamine Resistance by Matrix-Assisted Laser Desorption-Ionization Time-of-Flight Mass Spectrometry," Antimicrobial Agents and Chemotherapy, 2004, vol. 48 (2), pp. 466-472.
Marmur J., et al., "Strand Separation and Specific Recombination in Deoxyribonucleic Acids: Biological Studies," Proceedings of the National Academy of Sciences, 1960, vol. 46 (4), pp. 453-461.
Martineau F., et al., "Development of a PCR Assay for Identification of Staphylococci at Genus andSpecies Levels," Journal of Clinical Microbiology, 2001, vol. 39 (7), pp. 2541-2547.
Martineau F., et al., "Species-Specific and Ubiquitous-DNA-Based Assays for Rapid Identification of Staphylococcus Aureus," Journal of Clinical Microbiology, 1998, vol. 36 (3), pp. 618-623.
Martin-Lopez J.V., et al., "Simultaneous PCR Detection of ica Cluster and Methicillin and Mupirocinresistance Genes in Catheter-Isolated Staphylococcus," International Microbiology, 2004, vol. 7 (1), pp. 63-66.
Mason V.P., et al., "Diversity and linkage of Replication and Mobilisation Genes in Bacillus Rolling Irclereplicating Plasmids from Diverse Geographical Origins," FEMS Microbiology Ecology, 2002, vol. 42 (2), pp. 235-241.
Matsuoka M., et al., "Characteristic Expression of Three Genes, msr(A), mph(C) and erm(Y), Thatconfer Resistance to Macrolide Antibiotics on Staphylococcus Aureus," FEMS Microbiology Letters, 2003, vol. 220 (2), pp. 287-293.
May A.C., "Percent Sequence Identity: The Need to be Explicit," Structure, 2004, vol. 12 (5), pp. 737-738.
McLuckey S.A., et al., "Ion Trap Tandem Mass Spectrometry Applied to Small Multiply Charged Oligonucleotides with a Modified Base," Journal of the American Society for Mass Spectrometry, 1994, vol. 5, pp. 740-747.
Mehrotra M., et al., "Multiplex PCR for Detection of Genes for Staphylococcus Aureus Enterotoxins, Exfoliative Toxins, Toxic Shock Syndrome Toxin 1, and Methicillin Resistance," Journal of Clinical Microbiology, 2000, vol. 38 (3), pp. 1032-1035.
Mellor J., et al., "Genotype Dependence of Hepatitis C Virus Load Measurement in Commercially Available Quantitative Assays," Journal of Clinical Microbiology, 1999, vol. 37 (8), pp. 2525-2532.
Merlino J., et al., "New Chromogenic Identification and Detection of Staphylococcus Aureus andMethicillin-Resistant S. Aureus," Journal of Clinical Microbiology, 2000, vol. 38 (6), pp. 2378-2380.
Merlino J., et al., "Rapid Detection of Non-Multidrug-Resistant and Multidrug-Resistant Methicillin- Resistant Staphylococcus Aureus Using Cycling Probe Technology for the mecA Gene," European Journal of Clinical Microbiology & Infectious Diseases, 2003, vol. 22 (5), pp. 322-323.
Metzgar D., et al., "PCR Analysis of Egyptian Respiratory Adenovirus Isolates, Including Identification of Species, Serotypes and Coinfections," Journal of Clinical Microbiology, 2005, vol. 43 (11), pp. 5743-5752.
Miragaia M., et al., "Genetic Diversity among Methicillin-Resistant *Staphylococcus epidemidis*(MRSE," Microbial Drug Resistance, 2005, vol. 11 (2), pp. 83-93.
Miura-Ochiai R., et al., "Quantitative Detection and Rapid Identification of Human Adenoviruses," Journal of Clinical Microbiology, 2007, vol. 45 (3), pp. 958-967.
Mollet C., et al., "rpoB Sequence Analysis as a Novel Basis for Bacterial Identification," Molecular Microbiology, 1997, vol. 26 (5), pp. 1005-1011.
Monroy A.M., et al., "Exvaluation of Reverse Transcriptase Polymerase Chain Reaction for theDetection of Eastern Equine Encephalumyelitis Virus during Vector Surveillance," Journal of Medical Entomology, 1996, vol. 33 (3), pp. 449-457.
Moore C., et al., "Development and Evaluation of a Real-Time Nucleic Acid Sequence Based Amplification Assay for Rapid Detection of Influenza A," Journal of Medical Virology, 2004, vol. 74 (4), pp. 619-628.
Morinaga N., et al., "Purification, Cloning and Charactarizarion of Variant LukE-LukD with Strong Leukocidal Activity of Staphylococcal Bi-Component Leukotoxin Family," Microbiology and Immunology, 2003, vol. 47 (1), pp. 81-90.
Murakami K., et al., "Identification of Methicillin-Resistant Strains of Staphylococci by PolymeraseChain Reaction," Journal of Clinical Microbiology, 1991, vol. 29 (10), pp. 2240-2244.
Na B.K., et al., "Detection and Typing of Respiratory Adenoviruses in a Single-Tube Multiplex Polymerase Chain Reaction," Journal of Medical Virology, 2002, vol. 66 (4), pp. 512-517.
Nagy M., et al., "Sequence Analysis of Porcine Adenovirus Serotype 5 Fibre Gene: Evidence for Recombination," Virus Genes, 2002, vol. 24 (2), pp. 181-185.
Naito Y., et al., "Molecular Mass Measurement of Polymerase Chain Reaction Products Amplified from Human Blood DNA by Electrospray Ionization Mass Spectrometry," Rapid Communications in Mass Spectrometry, 1995, vol. 9 (15), pp. 1484-1486.
Nakagawa S., et al., "Gene sequences and specific detection for Panton-Valentine leukocidin," Biochemical and Biophysical Research Communications, 2005, vol. 328 (4), pp. 995-1002.
Narita S., et al., "Phage conversion of Panton-Valentine leukocidin in *Staphylococcus aureus*: molecular analysis of a PVL-converting phage, cpSLT," Gene, 2001, vol. 268 (1-2), pp. 195-206.
NEB Catalog. 1998/1999 pp. 1, 79, 121 and 284.
Neumann G., et al., "Host Range Restriction and Pathogenicity in the Context of Influenza Pandemic," Emerging Infectious Diseases, 2006, vol. 12 (6), pp. 881-886.
Newcombe J., et al., "PCR of Peripheral Blood for Diagnosis of Meningococcal Disease," Journal of Clinical Microbiology, 1996, vol. 34 (7), pp. 1637-1640.
Ng E.K., et al., "Quantitative Analysis an Prognostic Implication of SARS Coronavirus RNA in the Plasma and Serum of Patients with Severe Acute Respiratory Syndrome," Clinical Chemistry, 2003, vol. 49 (12), pp. 1976-1980.
Ng E.K., et al., "Serial Analysis of the Plasma Concentration of SARS Coronavirus RNA In Pediatric Patients with Severe Acute Respiratory Syndrome," Clinical Chemistry, 2003, vol. 49 (12), pp. 2085-2088.
Ni J., et al., "Interpretation of Oligonucleotide Mass Spectra for Determinationof Sequence Using Electrospray Ionization and Tandem Mass Spectrometry," Analytical Chemistry, 1996, vol. 68 (13), pp. 1989-1999.
Non-Final Office Action mailed Feb. 2, 2007 for U.S. Appl. No. 10/844,938 filed May 12, 2004.
Non-Final Office Action mailed Oct. 2, 2009 for U.S. Appl. No. 11/929,707 filed Oct. 30, 2007.
Non-Final Office Action mailed Aug. 4, 2010 for U.S. Appl. No. 12/049,949 filed Mar. 17, 2008.
Non-Final Office Action mailed Apr. 6, 2009 for U.S. Appl. No. 11/331,987 filed Jan. 13, 2006.
Non-Final Office Action mailed Oct. 6, 2008 for U.S. Appl. No. 11/070,632 filed Mar. 2, 2005.
Non-Final Office Action mailed Apr. 7, 2006 for U.S. Appl. No. 10/964,571 filed Oct. 12, 2004.
Non-Final Office Action mailed Aug. 7, 2007 for U.S. Appl. No. 10/844,938 filed May 12, 2004.
Non-Final Office Action mailed Jun. 10, 2009 for U.S. Appl. No. 10/844,938 filed May 12, 2004.
Non-Final Office Action mailed Oct. 13, 2010 for U.S. Appl. No. 10/754,415 filed Jan. 9, 2004.
Non-Final Office Action mailed Sep. 16, 2009 for U.S. Appl. No. 11/233,630 filed Sep. 21, 2005.
Non-Final Office Action mailed Apr. 17, 2009 for U.S. Appl. No. 12/211,641 filed Sep. 16, 2008.
Non-Final Office Action mailed Nov. 19, 2003 for U.S. Appl. No. 09/798,007 filed Mar. 2, 2001.
Non-Final Office Action mailed Aug. 20, 2007 for U.S. Appl. No. 11/582,863 filed Oct. 17, 2006.
Non-Final Office Action mailed May 20, 2008 for U.S. Appl. No. 10/844,938 filed May 12, 2004.
Non-Final Office Action mailed Oct. 20, 2004 for U.S. Appl. No. 09/891,793 filed Jun. 26, 2001.
Non-Final Office Action mailed Feb. 23, 2009 for U.S. Appl. No. 10/660,122 filed Sep. 11, 2003.
Non-Final Office Action mailed May 26, 2010 for U.S. Appl. No. 11/869,449 filed Oct. 9, 2007.
Non-Final Office Action mailed Jul. 27, 2006 for U.S. Appl. No. 11/209439 filed Aug. 8, 2005.
Non-Final Office Action mailed Jun. 28, 2010 for U.S. Appl. No. 11/930,002 filed Oct. 30, 2007.
Non-Final Office Action mailed Sep. 28, 2009 for U.S. Appl. No. 11/930,017 filed Oct. 30, 2007.
Non-Final Office Action mailed Dec. 29, 2010 for U.S. Appl. No. 12/616,422 filed Nov. 11, 2009.
Non-Final Office Action mailed Apr. 30, 2010 for U.S. Appl. No. 11/930,108 filed Oct. 31, 2007.
Nordhoff E., et al., "Matrix Assisted Laser Desorption/Ionization Mass Spectrometry of Nucleic Acids with Wavelengths in the Ultraviolet and Infrared," Rapid Communications in Mass Spectrometry, 1992, vol. 6 (12), pp. 771-776.
Nubel U.,et al., "PCR primers to amplify 16S rRNA genes from Cyanobacteria," Applied andEnvironmental Microbiology, 1997, vol. 63 (8), pp. 3327-3332.
Null Allison P., et al., "Enzymatic Strategies for the Characterization of Nucleic Acids by Electrospray Ionization Mass Spectrometry," Rapid Communications in Mass Spectrometry, 2003, vol. 17 (24), pp. 2699-2706.
Nunes E.L., et al., "Detection of ileS-2 Gene Encoding Mupirocin Resistance in Methicillin-Resistant *Staphylococcus aureus* by Multiplex PCR," Diagnostic Microbiology and Infectious Disease, 1999, vol. 34 (2), pp. 77-81.
Nygren M., et al., "Quantification of HIV-1 Using Multiple Quantitative Polymerase Chain ReactionStandards and Bioluminometric Detection," Analytical Biochemistry, 2001, vol. 288 (1), pp. 28-38.
Oberacher H., et al., "Analysis of Polymerase Chain Reaction Products by On-Line Liquid Chromatography Mass Spectrometry for Genotyping of Polymeric Short tandem Repeat Loci," Analytical Chemistry, 2001, vol. 73 (21), pp. 5109-5115.
Oberacher H., et al., "Increased foresnic efficiency of DNA fingerprints through simultaneous resolution of length and nucleotide variability by high-performance mass spectrometry," Human Mutation, 2008, vol. 29 (3), pp. 427-432.
Oberste M.S., et al., "Improved molecular identification of enteroviruses by RT-PCR and ampicon sequencing," Journal of Medical Virology, 2003, vol. 26 (3), pp. 375-377.
Oberste M.S., et al., "Molecular epidemiology and type-specific detection of echovirus 11 isolates fromthe Americas, Europe, Africa, Australia, southern Asia and the Middle East," Virus Research, 2003, vol. 91 (2), pp. 241-248.

Oberste M.S., et al., "Molecular phylogeny and proposed classification of the Simian picornaviruses," Journal of Virology, 2002, vol. 76 (3), pp. 1244-1251.
Office Action mailed Mar. 23, 2009 for U.S. Appl. No. 10/418,514 filed Apr. 18, 2003.
Office Action mailed Apr. 1, 2004 for U.S. Appl. No. 10/156,608 filed May 24, 2002.
Office Action mailed Jul. 1, 2008 for U.S. Appl. No. 10/418,514 filed Apr. 18, 2003.
Office Action mailed May 1, 2006 for U.S. Appl. No. 10/660,998 filed Sep. 12, 2003.
Office Action mailed Feb. 2, 2007 for U.S. Appl. No. 09/891,793 filed Jun. 26, 2001.
Office Action mailed Feb. 2, 2011 for U.S. Appl. No. 11/869,449 filed Oct. 9, 2007.
Office Action mailed Jan. 2, 2009 for U.S. Appl. No. 11/060,135 filed Feb. 17, 2005.
Office Action mailed Jul. 2, 2009 for U.S. Appl. No. 11/582,930 filed Oct. 17, 2006.
Office Action mailed Jun. 2, 2006 for U.S. Appl. No. 10/933,928 filed Sep. 3, 2004.
Office Action mailed Jun. 2, 2008 for U.S. Appl. No. 11/331,978 filed Jan. 13, 2006.
Office Action mailed May 2, 2008 for U.S. Appl. No. 11/582,930 filed Oct. 17, 2006.
Office Action mailed Oct. 2, 2008 for U.S. Appl. No. 11/233,630 filed Sep. 21, 2005.
Office Action mailed Apr. 3, 2002 for U.S. Appl. No. 09/891,793 filed Jun. 26, 2001.
Office Action mailed Aug. 3, 2006 for U.S. Appl. No. 10/660,998 filed Sep. 12, 2003.
Office Action mailed Aug. 3, 2009 for U.S. Appl. No. 11/754,174 filed May 25, 2007.
Office Action mailed Dec. 3, 2003 for U.S. Appl. No. 10/325,527 filed Dec. 18, 2002.
Office Action mailed Feb. 3, 2011 for U.S. Appl. No. 12/326,800 filed Dec. 2, 2008.
Office Action mailed Jun. 3, 2009 for U.S. Appl. No. 11/331, 978 filed Jan. 13, 2006.
Office Action mailed Nov. 3, 2008 for U.S. Appl. No. 10/728,486 filed Dec. 5, 2003.
Office Action mailed Oct. 3, 2005 for U.S. Appl. No. 10/326,046 filed 18 Dec. 18, 2002.
Office Action mailed Apr. 4, 2008 for U.S. Appl. No. 10/829,826 filed Apr. 22, 2004.
Office Action mailed Dec. 4, 2006 for Indian Application No. 1136KOLNP2003 filed Mar. 4, 2002.
Office Action mailed Feb. 4, 2009 for U.S. Appl. No. 11/404,561 filed Apr. 12, 2006.
Office Action mailed Jan. 4, 2002 for U.S. Appl. No. 09/891,793 filed Jun. 26, 2001.
Office Action mailed Jun. 4, 2009 for U.S. Appl. No. 10/754,415 filed Jan. 9, 2004.
Office Action mailed May 4, 2010 for U.S. Appl. No. 90/010,447 filed Apr. 9, 2009.
Office Action mailed May 4, 2010 for U.S. Appl. No. 90/010,448 filed Apr. 9, 2009.
Office Action mailed Nov. 4, 2009 for European Application No. 02709785.6 filed Mar. 4, 2002.
Office Action mailed Sep. 4, 2008 for Australian Application No. 2003297687 filed Dec. 5, 2003.
Office Action mailed Aug. 5, 2010 for European Application No. 02709785.6 filed Mar. 4, 2002.
Office Action mailed Aug. 5, 2010 for U.S. Appl. No. 11/233,630 filed Sep. 21, 2005.
Office Action mailed Sep. 5, 2006 for U.S. Appl. No. 10/660,996 filed Sep. 12, 2003.
Office Action mailed Aug. 6, 2009 for U.S. Appl. No. 10/728,486 filed Dec. 5, 2003.
Office Action mailed Dec. 6, 2007 for U.S. Appl. No. 10/418,514 filed Apr. 18, 2003.
Office Action mailed Jan. 6, 2009 for U.S. Appl. No. 10/660,996 filed Sep. 12, 2003.
Office Action mailed Jul. 6, 2006 for U.S. Appl. No. 10/660,122 filed Sep. 11, 2003.
Office Action mailed Jul. 6, 2007 for U.S. Appl. No. 10/829,826 filed Apr. 22, 2004.
Office Action mailed Mar. 6, 2009 for U.S. Appl. No. 11/233,630 filed Sep. 21, 2005.
Office Action mailed Nov. 6, 2002 for U.S. Appl. No. 09/798,007 filed Mar.2, 2001.
Office Action mailed Nov. 6, 2008 for U.S. Appl. No. 10/728,486 filed Dec. 5, 2003.
Office Action mailed Oct. 6, 2009 for European Application No. 08730682.5 filed Feb. 25, 2008.
Office Action mailed Apr. 7, 2009 for Canadian Application No. 2525498 filed May 13, 2004.
Office Action mailed Apr. 7, 2009 for European Application No. 07760292.8 filed Apr. 6, 2007.
Office Action mailed Apr. 7, 2009 for U.S. Appl. No. 10/660,998 filed Sep. 12, 2003.
Office Action mailed Aug. 7, 2007 for U.S. Appl. No. 10/660,997 filed Sep. 12, 2003.
Office Action mailed Aug. 7, 2007 for U.S. Appl. No. 10/660,998 filed Sep. 12, 2003.
Office Action mailed Feb. 27, 2008 for European Application No. 03796752.8 filed Dec. 5, 2003.
Office Action mailed Jun. 7, 2010 for European Application No. 06800205.4 filed Jul. 27, 2006.
Office Action mailed Jan. 8, 2003 for U.S. Appl. No. 09/798,007 filed Mar. 2, 2001.
Office Action mailed Jan. 8, 2007 for U.S. Appl. No. 09/891,793 filed Jun. 26, 2001.
Office Action mailed Jun. 8, 2007 for U.S. Appl. No. 1 1/210,516 filed Aug. 24, 2005.
Office Action mailed Mar. 8, 2005 for U.S. Appl. No. 09/891,793 filed Jun. 26, 2001.
Office Action mailed Mar. 8, 2007 for U.S. Appl. No. 11/060,135 filed Feb. 17, 2005.
Office Action mailed Sep. 8, 2006 for Chinese Application No. 02809122.1 filed Mar. 4, 2002.
Office Action mailed Dec. 9, 2004 for U.S. Appl. No. 10/156,608 filed May 24, 2002.
Office Action mailed Dec. 9, 2009 for U.S. Appl. No. 90/010,210 filed Jun. 27, 2008.
Office Action mailed Dec. 9, 2009 for U.S. Appl. No. 90/010,447 filed Apr. 9, 2009.
Office Action mailed Dec. 9, 2009 for U.S. Appl. No. 90/010,448 filed Apr. 9, 2009.
Office Action mailed Feb. 9, 2009 for Chinese Application No. 02809122.1 filed Mar. 4, 2002.
Office Action mailed Jan. 9, 2008 for Japanese Application No. 2002570692 filed Mar. 4, 2002.
Office Action mailed Jul. 9, 2008 for U.S. Appl. No. 10/660,122 filed Sep. 11, 2003.
Office Action mailed Jul. 9, 2008 for U.S. Appl. No. 11/331,987 filed Jan. 13, 2006.
Office Action mailed Mar. 9, 2004 for U.S. Appl. No. 09/891,793 filed Jun. 26, 2001.
Office Action mailed Nov. 9, 2010 for U. S. Appl. No. 11/331,987 filed Jan. 13, 2006.
Office Action mailed Aug. 10, 2010 for U. S. Appl. No. 09/891,793 filed Jun. 26, 2006.
Office Action mailed Aug. 10, 2010 for U. S. Appl. No. 09/798,007 filed Mar. 2, 2006.
Office Action mailed Aug. 10, 2010 for U. S. Appl. No. 10/156,608 filed May. 24, 2006.
Office Action mailed Aug. 10, 2010 for U. S. Appl. No. 10/326,642 filed Dec. 18, 2002.
Office Action mailed Aug. 10, 2005 for European Application No. 03796752.8 filed Dec. 5, 2003.
Office Action mailed Dec. 10, 2008 for U.S. Appl. No. 10/829,826 filed Apr. 22, 2004.
Office Action mailed Dec. 10, 2009 for U.S. Appl. No. 11/929,910 filed Oct. 30, 2007.

Office Action mailed Dec. 10, 2010 for U.S. Appl. No. 11/233,630 filed Sep. 21, 2005.
Office Action mailed Feb. 10, 2003 for U.S. Appl. No. 09/891,793 filed Jun. 26, 2001.
Office Action mailed Feb. 10, 2005 for U.S. Appl. No. 09/798,007 filed Mar. 2, 2001.
Office Action mailed Feb. 10, 2006 for Australian Application No. 2002244250 filed Mar. 4, 2002.
Office Action mailed Jun. 10, 2009 for U.S. Appl. No. 90/010,210 filed Jun. 27, 2008.
Office Action mailed Jun. 10, 2010 for U.S. Appl. No. 90/010,447 filed Apr. 9, 2009.
Office Action mailed Jun. 10, 2010 for U.S. Appl. No. 90/010,448 filed Apr. 9, 2009.
Office Action mailed Oct. 10, 2007 for U.S. Appl. No. 10/754,415 filed Jan. 9, 2004.
Office Action mailed Sep. 10, 2008 for Australian Application No. 2003302236 filed Dec. 5, 2003.
Office Action mailed Aug. 11, 2005 for U.S. Appl. No. 09/891,793 filed Jun. 26, 2001.
Office Action mailed Aug. 11, 2010 for U.S. Appl. No. 90/010,447 filed Apr. 9, 2009.
Office Action mailed Aug. 11, 2010 for U.S. Appl. No. 90/010,448 filed Apr. 9, 2009.
Office Action mailed Dec. 11, 2007 for U.S. Appl. No. 10/660,998 filed Sep. 12, 2003.
Office Action mailed Jul. 11, 2003 for U.S. Appl. No. 09/798,007 filed Mar. 2, 2001.
Office Action mailed Jun. 11, 2010 for U.S. Appl. No. 90/010,210 filed Jun. 27, 2008.
Office Action mailed Mar. 11, 2005 for U.S. Appl. No. 10/325,527 filed Dec.18, 2002.
Office Action mailed May 11, 2007 for U.S. Appl. No. 10/728,486 filed Dec. 5, 2003.
Office Action mailed Dec. 12, 2006 for U.S. Appl. No. 10/156,608 filed May 24, 2002.
Office Action mailed Feb. 12, 2009 for U.S. Appl. No. 11/136,134 filed May 24, 2005.
Office Action mailed Jul. 12, 2006 for U.S. Appl. No. 09/891,793 filed Jun. 26, 2001.
Office Action mailed Jul. 12, 2006 for U.S. Appl. No. 10/660,996 filed Sep. 12, 2003.
Office Action mailed Jun. 12, 2008 for U.S. Appl. No. 10/754,415 filed Jan. 9, 2004.
Office Action mailed Jun. 12, 2009 for Chinese Application No. 200480016187.9 filed May 13, 2004.
Office Action mailed Mar. 12, 2008 for European Application No. 06849755.1 filed Apr. 12, 2006.
Office Action mailed May 12, 2002 for U.S. Appl. No. 09/798,007 filed Mar. 2, 2001.
Office Action mailed Nov. 12, 2009 for U.S. Appl. No. 10/728,486 filed Dec. 5, 2003.
Office Action mailed Aug. 13, 2009 for U.S. Appl. No. 11/674,538 filed Feb. 13, 2007.
Office Action mailed Jul. 13, 2004 for U.S Appl. No. 09/891,793 filed Jun. 26, 2001.
Office Action mailed Jul. 13, 2007 for U.S. Appl. No. 11/233,630 filed Sep. 12, 2005.
Office Action mailed Jul. 13, 2010 for U.S. Appl. No. 11/929,930 filed Oct. 30, 2007.
Office Action mailed Mar. 13, 2006 for U.S. Appl. No. 10/754,415 filed Jan. 9, 2004.
Office Action mailed Nov. 13, 2003 for U.S. Appl. No. 09/891,793 filed Jun. 26, 2001.
Office Action mailed Sep. 13, 2006 for U.S. Appl. No. 09/891,793 filed Jun. 26, 2001.
Office Action mailed Jul. 14, 2004 for U.S. Appl. No. 10/326,642 filed Dec. 18, 2002.
Office Action mailed Jun. 14, 2004 for U.S. Appl. No. 09/891,793 filed Jun. 26, 2001.
Office Action mailed Sep. 14, 2007 for U.S. Appl. No. 11/582,930 filed Oct. 17, 2006.
Office Action mailed Apr. 15, 2008 for U.S. Appl. No. 10/418,514 filed Apr. 18, 2003.
Office Action mailed Aug. 15, 2008 for U.S. Appl. No. 11/331,978 filed Jan. 13, 2006.
Office Action mailed Dec. 15, 2008 for Israel Application No. 157661 filed Mar. 4, 2002.
Office Action mailed Dec. 15, 2008 for U.S. Appl. No. 11/331,978 filed Jan. 13, 2006.
Office Action mailed Jan. 15, 2008 for Israel Application No. 157661 filed Mar. 4, 2002.
Office Action mailed Jul. 15, 2009 for U.S. Appl. No. 11/060,135 filed Feb. 17, 2005.
Office Action mailed Mar. 15, 2010 for European Application No. 08730682.5 filed Feb. 25, 2008.
Office Action mailed Nov. 15, 2007 for U.S. Appl. No. 11/331,978 filed Jan. 13, 2006.
Office Action mailed Sep. 15, 2005 for U.S. Appl. No. 10/156,608 filed May 24, 2002.
Office Action mailed Apr. 16, 2002 for U.S. Appl. No. 09/798,007 filed Mar. 2, 2001.
Office Action mailed Apr. 16, 2008 for U.S. Appl. No. 11/233,630 filed Sep. 21, 2005.
Office Action mailed Apr. 16, 2008 for U.S. Appl. No. 11/409,535 filed Apr. 21, 2006.
Office Action mailed Apr. 16, 2009 for U.S. Appl. No. 90/010,210 filed Jun. 27, 2008.
Office Action mailed Aug. 16, 2004 for U.S. Appl. No. 10/325,527 filed Dec. 18, 2002.
Office Action mailed Aug. 16, 2010 for U.S. Appl. No. 11/929,707 filed Oct. 30, 2007.
Office Action mailed Jan. 16, 2009 for U.S. Appl. No. 11/582,930 filed Oct. 17, 2006.
Office Action mailed Jul. 16, 2007 for U.S. Appl. No. 11/331,987 filed Jan. 13, 2006.
Office Action mailed Mar. 16, 2006 for U.S. Appl. No. 09/891,793 filed Jun. 26, 2001.
Office Action mailed Mar. 16, 2010 for Canadian Application No. 2616281 filed Jul. 21, 2006.
Office Action mailed May 16, 2008 for U.S. Appl. No. 11/404,561 filed Apr. 12, 2006.
Office Action mailed Nov. 16, 2009 for Japanese Application No. 2005508488 filed Dec. 5, 2003.
Office Action mailed Nov. 16, 2009 for Japanese Application No. 2005508560 filed Dec. 5, 2003.
Office Action mailed Feb. 17, 2010 for U.S. Appl. No. 10/660,122 filed Sep. 11, 2003.
Office Action mailed Jul. 17, 2007 for U.S. Appl. No. 09/891,793 filed Jun. 26, 2001.
Office Action mailed Jun. 17, 2008 for U.S. Appl. No. 11/582,863 filed Oct. 17, 2006.
Office Action mailed Mar. 17, 2006 for U.S. Appl. No. 10/660,122 filed Sep. 11, 2003.
Office Action mailed Nov. 17, 2006 for U.S. Appl. No. 10/754,415 filed Jan. 9, 2004.
Office Action mailed Oct. 17, 2007 for U.S. Appl. No. 10/728,486 filed Dec. 5, 2003.
Office Action mailed Oct. 17, 2008 for U.S. Appl. No. 11/331,978 filed Jan. 13, 2006.
Office Action mailed Sep. 17, 2008 for European Application No. 03796752.8 filed Dec. 5, 2003.
Office Action mailed Sep. 17, 2008 for U.S. Appl. No. 10/660,122 filed Sep. 2003.
Office Action mailed Aug. 18, 2009 for U.S. Appl. No. 11/685,598 filed Mar. 13, 2007.
Office Action mailed Feb. 18, 2010 for European Application No. 03814656 filed Dec. 5, 2003.
Office Action mailed Jan. 18, 2011 for U.S. Appl. No. 11/930,108 filed Oct. 31, 2007.
Office Action mailed Mar. 18, 2010 for U.S. Appl. No. 11/331,978 filed Jan.13, 2006.
Office Action mailed May 18, 2005 for New Zealand Application No. 527857 filed Mar. 4, 2002.

Office Action mailed Sep. 18, 2006 for U.S. Appl. No. 10/660,997 filed Sep. 12, 2003.
Office Action mailed Sep. 18, 2008 for Australian Application No. 2003298030 filed Dec. 5, 2003.
Office Action mailed Sep. 18, 2008 for U.S. Appl. No. 10/660,998 filed Sep. 12, 2003.
Office Action mailed Sep. 18, 2009 for U.S. Appl. No. 10/660,998 filed Sep.12, 2003.
Office Action mailed Jan.19, 2007 for U.S. Appl. No. 11/059,776 filed Feb. 17, 2005.
Office Action mailed May 19, 2005 for U.S. Appl. No. 09/891,793 filed Jun. 26, 2001.
Office Action mailed Nov. 19, 2004 for U.S. Appl. No. 10/156,608 filed May 24, 2002.
Office Action mailed Oct. 19, 2007 for U.S. Appl. No. 11/210,516 filed Aug. 24, 2005.
Office Action mailed Sep. 19, 2006 for U.S. Appl. No. 10/660,122 filed Sep.11, 2003.
Office Action mailed Sep. 19, 2007 for U.S. Appl. No. 10/660,122 filed Sep. 11, 2003.
Office Action mailed Apr. 20, 2007 for U.S. Appl. No. 10/660,122 filed Sep. 11, 2003.
Office Action mailed Apr. 20, 2009 for U.S. Appl. No. 10/891,337 filed Jul. 14, 2004.
Office Action mailed Dec. 20, 2006 for U.S. Appl. No. 10/728,486 filed Dec. 5, 2003.
Office Action mailed Jul. 20, 2005 for U.S. Appl. No. 10/156,608 filed May 24, 2002.
Office Action mailed Jun. 20, 2002 for U.S. Appl. No. 09/798,007 filed Mar. 2, 2001.
Office Action mailed Jun. 20, 2007 for U.S. Appl. No. 11/136,134 filed May 24, 2005.
Office Action mailed Nov. 20, 2003 for U.S. Appl. No. 10/323,438 filed Dec. 18, 2002.
Office Action mailed Nov. 20, 2006 for U.S. Appl. No. 09/891,793 filed Jun. 26, 2001.
Office Action mailed Nov. 20, 2006 for European Application No. 02709785.6 filed Mar. 4, 2002.
Office Action mailed Sep. 20, 2010 for U.S. Appl. No. 90/010,447 filed Apr. 9, 2009.
Office Action mailed Sep. 20, 2010 for U.S. Appl. No. 90/010,448 filed Apr. 9, 2009.
Office Action mailed Apr. 21, 2009 for U.S. Appl. No. 90/010,209 filed Jun. 27, 2008.
Office Action mailed Dec. 21, 2006 for U.S. Appl. No. 11/060,135 filed Feb. 17, 2005.
Office Action mailed Mar. 21, 2008 for U.S. Appl. No. 10/660,122 filed Sep. 11, 2003.
Office Action mailed May 21, 2008 for U.S. Appl. No. 10/943,344 filed Sep. 17, 2004.
Office Action mailed May 21, 2009 for U.S. Appl. No. 11/136,134 filed May 24, 2005.
Office Action mailed Nov. 21, 2003 for U.S. Appl. No. 10/326,642 filed Dec. 18, 2002.
Office Action mailed Nov. 21, 2006 for U.S. Appl. No. 10/660,997 filed Sep. 21, 2003.
Office Action mailed Oct. 21, 2005 for U.S. Appl. No. 10/326,641 filed Dec.18, 2002.
Office Action mailed Oct. 21, 2008 for U.S. Appl. No. 11/582,859 filed Oct. 17, 2006.
Office Action mailed Oct. 21, 2009 for U.S. Appl. No. 12/326,800 filed Dec. 2, 2008.
Office Action mailed Jul. 22, 2008 for U.S. Appl. No. 90/010,209 filed Jun. 27, 2008.
Office Action mailed Jul. 22, 2008 for U.S. Appl. No. 90/010,210 filed Jun. 27, 2008.
Office Action mailed Nov. 22, 2006 for U.S. Appl. No. 10/660,996 filed Sep. 12, 2003.
Office Action mailed Oct. 22, 2007 for U.S. Appl. No. 11/331,987 filed Jan. 13, 2006.
Office Action mailed Sep. 22, 2003 for U.S. Appl. No. 09/798,007 filed Mar. 2, 2001.
Office Action mailed Sep. 22, 2010 for Canadian Application No. 2510007 filed Dec. 5, 2003.
Office Action mailed Apr. 23, 2010 for U.S. Appl. No. 90/010,210 filed Jun. 27, 2008.
Office Action mailed Feb. 23, 2009 for U.S. Appl. No. 10/943,344 filed Sep. 17, 2004.
Office Action mailed Jan. 23, 2008 for U.S. Appl. No. 10/728,486 filed Dec. 5, 2003.
Office Action mailed Jan. 23, 2008 for U.S. Appl. No. 11/059,776 filed Feb. 17, 2005.
Office Action mailed Jul. 23, 2009 for U.S. Appl. No. 11/070,634 filed Mar. 2, 2005.
Office Action mailed May 23, 2003 for U.S. Appl. No. 09/891,793 filed Jun. 26, 2001.
Office Action mailed May 23, 2005 for U.S. Appl. No. 10/156,608 filed May 24, 2002.
Office Action mailed Oct. 23, 2003 for New Zealand Application No. 527857 filed Mar. 4, 2002.
Office Action mailed Apr. 24, 2009 for U.S. Appl. No. 90/010,447 filed Apr. 9, 2009.
Office Action mailed Apr. 24, 2009 for U.S. Appl. No. 90/010,448 filed Apr. 9, 2009.
Office Action mailed Aug. 24, 2010 for U.S. Appl. No. 90/010,210 filed Jun. 27, 2008.
Office Action mailed Dec. 24, 2004 for New Zealand Application No. 527857 filed Mar. 4, 2002.
Office Action mailed Feb. 24, 2004 for U.S. Appl. No. 10/326642 filed Dec. 18, 2002.
Office Action mailed Feb. 24, 2010 for U.S. Appl. No. 10/728,486 filed Dec. 5, 2003.
Office Action mailed Jan. 24, 2005 for U.S. Appl. No. 10/326,642 filed Dec. 18, 2002.
Office Action mailed Jan. 24, 2007 for U.S. Appl. No. 10/660,998 filed Sep. 12, 2003.
Office Action mailed Jul. 24, 2007 for Mexican Application No. PAA2003007927 filed Sep.2, 2003.
Office Action mailed Jul. 24, 2007 for U.S. Appl. No. 11/060,135 filed Feb. 17, 2005.
Office Action mailed Jul. 24, 2009 for U.S. Appl. No. 11/754,182 filed May 25, 2007.
Office Action mailed Jun. 24, 2008 for European Application No. 06800205.4 filed Jul. 27, 2006.
Office Action mailed Nov. 24, 2009 for U.S. Appl. No. 11/331,978 filed Jan. 13, 2006.
Office Action mailed Nov. 24, 2009 for U.S. Appl. No. 90/010,210 filed Jun. 27, 2008.
Office Action mailed Oct. 24, 2008 for U.S. Appl. No. 11/582,930 filed Oct. 17, 2006.
Office Action mailed Sep. 24, 2009 for U.S. Appl. No. 90/010,210 filed Jun. 27, 2008.
Office Action mailed Aug. 25, 2009 for U.S. Appl. No. 11/754,169 filed May 25, 2007.
Office Action mailed Jun. 25, 2009 for U.S. Appl. No. 11/869,449 filed Oct. 9, 2007.
Office Action mailed Jun. 25, 2009 for U.S. Appl. No. 90/010,210 filed Jun. 27, 2008.
Office Action mailed Mar. 25, 2008 for U.S. Appl. No. 11/060,135 filed Feb. 17, 2005.
Office Action mailed Aug. 26, 2003 for U.S. Appl. No. 09/891,793 filed Jun. 26, 2001.
Office Action mailed Aug. 26, 2010 for Canadian Application No. 2508584 filed Dec. 5, 2003.
Office Action mailed Jul. 26, 2004 for U.S. Appl. No. 10/323,438 filed Dec. 18, 2002.
Office Action mailed Mar. 26, 2008 for U.S. Appl. No. 11/136,134 filed May 24, 2005.
Office Action mailed May 26, 2005 for U.S. Appl. No. 10/156,608 filed May 24, 2002.
Office Action mailed May 26, 2006 for U.S. Appl. No. 10/660,997 filed Sep. 12, 2003.
Office Action mailed Feb. 27, 2003 for U.S. Appl. No. 09/798,007 filed Mar. 2, 2001.

Office Action mailed Feb. 27, 2006 for U.S. Appl.No. 10/326,644 filed Dec. 18, 2002.
Office Action mailed Feb. 27, 2006 for U.S. Appl. No. 10/418,514 filed Apr. 18,2003.
Office Action mailed Feb. 27, 2007 for U.S. Appl. No. 10/754,415 filed Jan. 9, 2004.
Office Action mailed Feb. 27, 2007 for U.S. Appl. No. 10/943,344 filed Sep. 17, 2004.
Office Action mailed Jan. 27, 2006 for U.S. Appl. No. 10/323,211 filed Dec. 18, 2002.
Office Action mailed Jul. 27, 2006 for U.S. Appl.No. 10/728,486 filed Dec. 5, 2003.
Office Action mailed Jul. 27, 2009 for Canadian Application No. 2439655 filed Mar. 4, 2002.
Office Action mailed Mar. 27, 2007 for U.S. Appl. No. 10/418,514 filed Apr. 18, 2003.
Office Action mailed Aug. 28, 2006 for U.S. Appl. No. 10/754,415 filed Jan. 9, 2004.
Office Action mailed Feb. 28, 2006 for U.S. Appl. No. 10/660,996 filed Sep. 12, 2003.
Office Action mailed Jul. 28, 2009 for U.S. Appl. No. 11/754,163 filed May 25, 2007.
Office Action mailed Jul. 28, 2010 for U.S. Appl. No. 90/010,210 filed Jun. 27, 2008.
Office Action mailed May 28, 2003 for U.S. Appl. No. 09/798,007 filed Mar. 2, 2001.
Office Action mailed May 28, 2008 for U.S. Appl. No. 10/660,998 filed Sep. 12, 2003.
Office Action mailed Oct. 28, 2008 for U.S. Appl. No. 11/331,987 filed Jan. 13, 2006.
Office Action mailed Mar. 29, 2010 for Australian Application No. 2006272776 filed Jul. 21, 2006.
Office Action mailed May 29, 2007 for U.S. Appl. No. 11/059,776 filed Feb. 17 2005.
Office Action mailed Oct. 29, 2008 for U.S. Appl. No. 11/331,978 filed Jan. 13, 2006.
Office Action mailed Oct. 29, 2009 for U.S. Appl. No. 10/660,122 filed Sep. 11, 2003.
Office Action mailed Oct. 29, 2009 for U.S. Appl. No. 90/010,447 filed Apr. 9, 2009.
Office Action mailed Oct. 29, 2009 for U.S. Appl. No. 90/010,448 filed Apr. 9, 2009.
Office Action mailed Sep. 29, 2005 for U.S. Appl. No. 10/418,514 filed Apr. 18, 2003.
Office Action mailed Sep. 29, 2009 for U.S. Appl. No. 10/418,514 filed Apr. 18, 2003.
Office Action mailed Aug. 30, 2007 for U.S. Appl. No. 10/754,415 filed Jan. 9, 2004.
Office Action mailed Jul. 30, 2008 for Australian Application No. 2004248107 filed Apr. 23, 2004.
Office Action mailed Jul. 30, 2009 for Japanese Application No. 2002570692 filed Mar. 4, 2002.
Office Action mailed Jun. 30, 2004 for U.S. Appl. No. 09/798,007 filed Mar. 2, 2001.
Office Action mailed Jun. 30, 2010 for U.S. Appl. No. 90/010,210 filed Jun. 27, 2008.
Office Action mailed Jun. 30, 2010 for U.S. Appl. No. 90/010,447 filed Apr. 9, 2009.
Office Action mailed Jun. 30, 2010 for U.S. Appl. No. 90/010,448 filed Apr. 9, 2009.
Office Action mailed May 30, 2006 for U.S. Appl. No. 10/660,996 filed Sep. 12, 2003.
Office Action mailed Nov. 30, 2009 for U.S. Appl. No. 10/660,122 filed Sep. 11, 2003.
Office Action mailed Sep. 30, 2005 for Chinese Application No. 02809122.1 filed Mar. 4, 2002.
Office Action mailed Jan. 31, 2003 for U.S. Appl. No. 09/798,007 filed Mar. 2, 2001.
Office Action mailed Jan. 31, 2007 for Philippines Application No. PH12003500824 filed Mar. 4, 2002.
Office Action mailed Jul. 31, 2006 for U.S. Appl. No. 10/326,643 filed Dec. 18, 2002.
Office Action mailed Oct. 31, 2007 for U.S. Appl. No. 11/409,535 filed Apr. 21, 2006.
Office Action mailed Oct. 31, 2008 for U.S. Appl. No. 11/136,134 filed May 24, 2005.
O'Guinn M.L., et al., "Field Detection of Eastern Equine Encephalitis Virus in the Amazon BasinRegion of Peru Using Reverse Transcription-Polymerase Chain Reaction Adapted for FieldIdentification of Arthropod-Borne Pathogens," American Journal of Tropical Medicine and Hygiene, 2004, vol. 70 (2), pp. 164-171.
Oizumi N., et al., "Relationship between mutations in the DNA gyrase and topoisomerase IV genes and nadifloxacin resistance in clinically isolated quinolone-resistant *Staphylococcus aureus*," Journal of Infection and Chemotherapy, 2001, vol. 7 (3), pp. 191-194.
Okada M., et al., "Detection and sequence-based typing of human adenoviruses using sensitiveuniversal primer sets for the hexon gene," Archives of Virology, 2007, vol. 152 (1), pp. 1-9.
Okuma K., et al., "Dissemination of New Methicillin-Resistant *Staphylococcus aureus* Clones in the Community," Journal of Clinical Microbiology, 2002, vol. 40 (11), pp. 4289-4294.
Oliveira D.C., et al., "Genetic Organization of the Downstream Region of the mecA Element inMethicillin-Resistant *Staphylococcus aureus* Isolates Carrying Different Polymorphisms of This Region," Antimicrobial Agents and Chemotherapy, 2000, vol. 44 (7), pp. 1906-1910.
Oliveira D.C., et al., "Multiplex PCR Strategy for Rapid Identification of Structural Types and Variants of the mec Element in Methicillin-Resistant *Staphylococcus aureus*," Antimicrobial Agents and Chemotherapy, 2002, vol. 46 (7), pp. 2155-2161.
Olsen B., et al., "Transhemispheric Exchange of Lyme Disease Spyrochetes by Seabirds," Journal of Clinical Microbiology, 1995, vol. 33 (12), pp. 3270-3274.
Osiowy C., et al., "Direct Detection of Respiratory Syncytial Virus, Parainfluenza Virus, and Adenovirus in Clinical Respiratory Specimens by a Multiplex Reverse Transcription-PCR Assay," Journal of Clinical Microbiology, 1998, vol. 36 (11), pp. 3149-3154.
Ostrander E.A., et al., "Identification and Characterization of Dinucleotide Repeat (CA)n. Markers for Genetic Mapping in Dog," Genomics, 1993, vol. 16 (1), pp. 207-213.
Ounissi H., et al., "Gene Homogeneity for Aminoglycoside-Modifying Enzymes in Gram-PositiveCocci," Antimicrobial Agents and Chemotherapy, 1990, vol. 34 (11), pp. 2164-2168.
Palys T., et al., "Discovery and Classification of Ecological Diversity in the Bacterial World: the Role of DNA Sequence Data," International Journal of Systematic Bacteriology, vol. 47 (4), pp. 1145-1156.
Pan ZQ., et al., "Oligonucleotide-targeted degradation of U1 and U2 snRNAs reveals differential interactions of simian virus 40 pre-mRNAs with snRNPs," Nucleic Acids Research, 1989, vol. 17 (16), pp. 6553-6568.
Pannetier C., et al., "Quantitative Titration of Nucleic Acids by Enzymatic Amplification Reactions run to Saturation," Nucleic Acids Research, 1993, vol. 21 (3), pp. 577-583.
Partial European Search Report for Application No. EP01106974, mailed on Dec. 16, 2002, 2 pages.
Pastorino B., et al., "Development of a TagMan PCR assay without RNA extraction step for the detection and quantification of African Chikungunya viruses," Journal of Virological Methods, 2005, vol. 124 (1-2), pp. 65-71.
Pawa A., et al., "Co-transfer of plasmids in association with conjugative transfer of mupirocin or mupirocin and penicillin resistance in methicillin-resistant *Staphylococcus aureus*," Journal of Clinical Microbiology, 2000, vol. 49 (12), pp. 1103-1107.
Payne D., et al., "Antimicrobials: The Challenge of Antibiotic Resistant Bacterial Pathogens: the Medical Need, the Market and Prospects for New Antimicrobial Agents," Current Opinion in Microbiology, 2004, vol. 7, pp. 435-438.
Perez-Roth E., et al., "Multiplex PCR for Simultaneous Identification of *Staphylococcus aureus* andDetection of Methicillin and Mupirocin Resistance," Journal of Clinical Microbiology, 2001, vol. 39 (11), pp. 4037-4041.
Peters S.E., et al., "Quantification of the detection of *Pneumocystis carinii* by DNA amplification," Molecular and Cellur Probes, 1992, vol. 6 (2), pp. 115-117.

Pfeffer M., et al., "Genus-Specific Detection of Alphaviruses by a Semi-Nested ReverseTranscription-Polymerase Chain Reaction," American Journal of Tropical Medicine and Hygiene, 1997, vol. 57 (6), pp. 709-718.
Pfeffer M., et al., "Specific Detection of Chikungunya Virus Using a RT-PCR/Nested PCR Combination," Journal of Veterinary Medicine B, 2002, vol. 49 (1), pp. 49-54.
Pieles U., et al., "Matrix-Assisted Laser Desorption Ionization Time-of-Flight Spectrometry: APowerful Tool for the Mass and Sequence Analysis of Natural and Modified Oligonucleotides, 787 reexamination," Nucleic Acids Research, 1993, vol. 21 (14), pp. 3191-3196.
Pillai S.D., et al., "Rapid molecular detection of microbial pathogens: breakthroughs and challenges," Archives of Virology, vol. 13, pp. 67-82.
Piper J., et al., "Commercially Available Technique for Rapid Laboratory Detection of MethicillinResistance Among *Staphylococcus aureus*," Diagnostic Microbiology and Infectious Disease, 1988, vol. 11 (3), pp. 177-180.
Poddar S.K., et al., "Detection of adenovirus using PCR and molecular beacon," Journal of Virological Methods, 1999, vol. 82 (1), pp. 19-26.
Pring-Akerblom P., et al., "Multiplex Polymerase Chain Reaction for Subgenus-Specific Detection of Human Adenoviruses in Clinical Samples," Journal of Medical Virology, 1999, vol. 58 (1), pp. 87-92.
Pring-Akerblom P., et al., "PCR-based detection and typing of human adenoviruses in clinical samples," Research in Virology, 1997, vol. 148 (3), pp. 225- 231.
Promega. T4 Polynucleotide Kinase, Technical Bulletin No. 519, 2002.
Puthavathana P., et al., "Molecular characterization of the complete genome of human influenza H5N1 virus Isolates from Thailand," Journal of General Virology, 2005, vol. 86 (2), pp. 423-433.
Qadri S.M., et al., "Rapid Detection of Methicillin-Resistant *Staphylococcus aureus* by CrystalMRSA Id System," Journal of Clinical Microbiology, 1994, vol. 32 (7), pp. 1830- 1832.
Ramisse V., et al., "Identification and characterization of *Bacillus anthracis* by multiplex PCR analysis of sequences on plasmids pX01 and pX02 and chromosomal DNA," FEMS Microbiology Letters, 1996, vol. 145 (1), pp. 9-16.
Reischl U., "Application of Molecular Biology-Based Methods to theDiagnosis of Infectious Diseases 1, e72-e77.," Frontiers in Bioscience, 1996, vol. 1 (1), pp. e72-e77.
Reischl U., et al., "Rapid Identification of Methicillin-Resistant *Staphylococcus aureus* and Simultaneous Species Confirmation Using Real-Time Fluorescence PCR," Journal of Clinical Microbiology, 2000, vol. 38 (6), pp. 2429-2433.
Roberts M.M., et al., "Three-Dimensional Structure of the Adenovirus Major Coat Protein Hexon," Science, 1986, vol. 232 (4754), pp. 1148-1151.
Roberts M.S., et al., "Recombination and Migration Rates in Natural Populations of Bacillus Subtilis and Bacillus Mojavenis," Evolution, 1995, vol. 49(6), pp. 1081-1094.
Robinson D.A., et al., "Multilocus sequence typing and the evolution of methicillin-resistant*Staphylococcus aureus*," Clinical Microbiology and Infection, 2004, vol. 10, pp. 92-97.
Rong S., et al., "Design and Application of 60mer Oligonucleotide Microarray in SARS Coronavirus Detection," Chinese Science Bulletin, 2003, vol. 48 (12), pp. 1165-1169.
Rota P.A., et al., "Sequencing of a cDNA clone of the nucleoprotein gene of influenza B/Ann Arbor/1/86," Nucleic Acids Research, 1989, vol. 17 (9), pp. 3595.
Ruan Y., et al., "Comparative full-length genome sequence analysis of 14 SARS coronavirus isolates and common mutations associated with the putative origins of infection," The Lancet, 2003, vol. 361, pp. 1779-1785, 1832.
Ruest A, et al., "Comparison of the Directigen Flu A+B test, the QuickVue Influenza Test, and Clinical Case Definition to Viral Culture and Reverse Transcription-PCR for Rapid Diagnosis of Influenza Virus Infection," Journal of Clinical Microbiology, 2003, vol. 41 (8), pp. 3487-3493.
Rupf S., et al., "Quantitative determination of *Streptococcus mutans* by using competitive polymerasechain reaction," European Journal of Oral Sciences, 1999, vol. 107 (2), pp. 75-81.
Russell K.L., et al., "Transmission Dynamics and Prospective Environmental Sampling of Adenovirus in a Military Recruit Setting," Journal of Infectious Diseases, 2006, vol. 194 (7), pp. 877-885.
Sabat A., et al., "Comparison of PCR-Based Methods for Typing *Staphylococcus aureus* Isolates" Journal of Clinical Microbiology, 2006, vol. 44 (10), pp. 3804-3807.
Sackesen C., et al., "Use of polymerase chain reaction for detection of adenovirus in children withor without wheezing," Turkish Journal of Pediatrics, 2005, vol. 47 (3), pp. 227-231.
Sakai H., et al., "Simultaneous Detection of *Staphylococcus aureus* and Coagulase—Staphylococci in Positive Blood Cultures by Real-Time PCR with Two Fluorescence Resonance Energy Transfer Probe Sets," Journal of Clinical Microbiology, 2004, vol. 42 (12), pp. 5739-5744.
Sambrook J., et al., "Molecular Cloning-A Laboratory Manual," 1989, Cold Spring Harbor Laboratory Press, Table of Contents.
Sampath R., et al., "Global Surveillance of Emerging Influenza Virus Genotypes by Mass Spectrometry," Plos ONE, 2007, vol. 2 (5), pp. e489.
Sampath R., et al., "Rapid Identification of Emerging Infectious Agents using PCR and Electrospray Ionization Mass Spectrometry," Annals of the New York Academy of Science, 2007, vol. 1102, pp. 109-120.
Sampath R., et al., "Rapid Identification of Emerging Pathogens: Coronavirus," Emerging Infectious Diseases, 2005, vol. 11 (3), pp. 373-379.
Sanchez A., et al., "Detection and molecularcharacterization of Ebola viruses causing disease in human and nonhuman primates," Journal of Infectious Diseases, 1999, vol. 179 (1), pp. S164-S169.
Sanchez J.L., et al., "Epidemic of Adenovirus-Induced Respiratory Illness Among US Military Recruits: Epidemiologic and Immunologic Risk Factors in Healthy, Young adults," Journal of Medical Virology, 2001, vol. 65 (4), pp. 710-718.
Sanchez-Seco M.P., et al., "A Generic Nested-RT-PCR followed by Sequencing for Detection and Identification of Members of the Alphavirus Genus," Journal of Virological Methods, 2001, vol. 95 (1-2), pp. 153-161.
Santos S.R., et al., "Identification and phylogenetic sorting of bacterial lineages with universally conserved genes and proteins," Environmental Microbiology, 2004, vol. 6 (7), pp. 754-759.
Sarantis H., et al., "Comprehensive Detection and Serotyping of Human Adenoviruses by PCR and Sequencing," Journal of Clinical Microbiology, 2004, vol. 42 (9), pp. 3963-3969.
Schabereiter-Gurtner C., et al., "Application of Broad-Range 16s rRNA PCR Amplification and DGGE Fingerprinting for Detection of Tick-Infecting Bacteria," The Journal of Microbiological Methods, 2003, vol. 52 (2), pp. 251-260.
Scheffner M., et al., "The E6 Oncoprotein Encoded by Human Papillomavirus Types 16 and 18 Promotes the Degradation of p53," Cell, 1990, vol. 63 (6), pp. 1129-1136.
Schena M., et al., "Genome Analysis with Gene Expression Microarrays," Bioessays, 1996, vol. 18 (5), pp. 427-431.
Scheuermann R.H., et al., "Polymerase chain-reaction-based mRNA quantification Using an internal standard: analysis of oncogene expression," Methods in Enzymology, 1993, vol. 218, pp. 446-473.
Schlecht N. F., et al., "Viral Load as a Predictor of the Risk of Cervical Intraepithelial Neoplasia," British Journal of Cancer, 2003, vol. 103 (4), pp. 519-524.
Schmidt T.M., et al., "Analysis of a marine pikoplankton community by 16s rRNA gene cloning and sequencing," Journal of Bacteriology, 1991, vol. 173 (14), pp. 4371- 4378.
Schmitz F.J., et al., "Development of a Multiplex-PCR for Direct Detection of the Genes for Enterotoxin B and C, and Toxic Shock Syndrome Toxin-1 in Staphylococcus Aureus Isolates," Journal of Medical Microbiology, 1998, vol. 47 (4), pp. 335-340.
Schmitz F.J., et al., "Development of Resistance to Ciprofloxacin, Rifampin, and Mupirocin inMethicillin-Susceptible and -Resistant *Staphylococcus aureus* Isolates," Antimicrobial Agents and Chemotherapy, 2000, vol. 44 (11), pp. 3229-3231.
Schmitz F.J., et al., "Specific information concerning taxonomy, pathogenicity and methicillin esistance of staphylococci obtained by a multiplex PCR," Journal of Medical Microbiology, 1997, vol. 46 (9), pp. 773-778.

Schwartz M., et al., "Prenatal Diagnosis of Alpha-1-Antitrypsin Deficiency Using Polymerase Chainreaction (PCR). Comparison of Conventional RFLP Methods with PCR used in Combination with Allelespecific Oligonucleotides or RFLP analysis, 787 Reexamination," Clinical Genetics, 1989, vol. 36 (6), pp. 419-426.
Schweiger B., et al., "Application of a Fluorogenic PCR Assay for Typing and Subtyping of Influenza Viruses in Respiratory Samples," Journal of Clinical Microbiology, 2000, vol. 38 (4), pp. 1552-1558.
Sciacchitano C.J., "Analysis of Polymerase Chain Reaction-Amplified DNA Fragments of Clostridium Botulinum Type E Neurotoxin Gene by High Performance Capillary Electrophoresis," Journal of Liquid Chromatography & Related Technologies, 1996, vol. 19 (13), pp. 2165-2178.
Scott-Taylor T.H., et al., "Conserved Sequences of the Adenovirus Genome for Detection of all Human Adenovirus Types by Hybridization," Journal of Clinical Microbiology, 1992, vol. 30 (7), pp. 1703-1710.
Seifarth W., et al., "Rapid identification of all known retroviral reverse transcriptase sequences with a novel versatile detection assay," AIDS Research and Human Retroviruses, 2000, vol. 16 (8), pp. 721-729.
Sellner L., et al., "A Single-Tube Nested RT-PCR for the Detection of Ross River Virus," Methods in Molecular Biology, 1998, vol. 92, pp. 145-152.
Sellner L.N., et al., "Sensitive detection of Ross River virus— a one-tube nested RT-PCR," Journal of Virological Methods, 1994, vol. 49 (1), pp. 47-58.
Shadan F.F., et al., "n-Butyrate, a Cell Cycle Blocker, Inhibits the Replication of Polyomaviruses and Papillomaviruses but Not That of Adenoviruses and Herpesviruses," Journal of Virology, 1994, vol. 68 (8), pp. 4785-4796.
Shimaoka M., et al., "Detection of the gene for toxic shock syndrome toxin 1 in Siaphylococcusaureus by enzyme-labelled oligonucleotideprobes," Journal of Medical Microbiology, 1996, vol. 44 (3), pp. 215-218.
Shimaoka M., et al., "Development of Enzyme-Labeled Oligonucleotide Probe for Detection of mecA gene in Methicillin-Resistant *Staphylococcus aureus*," Journal of Clinical Microbiology, 1994, vol. 32 (8), pp. 1866-1869.
Shrestha N. K., et al., "Rapid Identification of *Staphylococcus aureus* and the mecA Gene fromBacT/ALERT Blood Culture Bottles by Using the Lightcycler System," Journal of Clinical Microbiology, 2002, vol. 40 (7), pp. 2659-2661.
Simonsen L., et al., "The Impact of Influenza Epidemics on Hospitalizations," Journal of Infectious Diseases, 2000, vol. 181 (3), pp. 831-837.
Skov R.L., et al., "Evaluation of a new 3-h hybridization method for detecting the mecA gene in *Staphylococcus aureus* and comparison with existing genotypic and phenotypic susceptibility testing methods," Journal of Antimicrobial Chemotherapy, 1999, vol. 43 (4), pp. 467-475.
Smirnov I.P., et al., "Application of DNA-binding polymers for preparation of DNA for analysis by matrix-assisted laser desorption/ ionization mass spectrometry," Rapid Communications in Mass Spectrometry, 2001, vol. 15 (16), pp. 1427-1432.
Smith T.F., "Comparison of Biosequences," Advances in Applied Mathematics, 1981, vol. 2, pp. 482-489.
Song F., et al., "Identification of cry11-type Genes from Bacilus Thuringiensis Strains and Characterization of a Novel Cry11-Type Gene," Applied and Environmental Microbiology, 2003, vol. 69, pp. 5207-5211.
Spackman E., et al., "Development of a real-time reverse transcriptase PCR assay for type A influenzavirus and the avian H5 and H7 hemagglutinin subtypes," Journal of Clinical Microbiology, 2002, vol. 40 (9), pp. 3256-3260.
Spiess L., et al., "Trehalose is a potent PCR enhancer: Lowering of DNA melting temperature and thermal stabilization of Taq polymerase by the disaccharide trehalose," Clinical Chemistry, 2004, vol. 50 (7), pp. 1256-1259.
Stephensen C.B., et al., "Phylogenetic analysis of a highly conserved region of the poymerase gene from 11 coronaviruses and development of a consensus poymerase chain reaction assay," Virus Research, 1999, vol. 60 (2), pp. 181-189.
Stone B., et al., "Rapid detection and simultaneous subtype differentiation of influenza A viruses by real time PCR," Journal of Virological Methods, 2004, vol. 117 (2), pp. 103-112.
Stratagene Catalog. 1988, p. 39.
Strommenger B., et al., "Multiplex PCR Assay for Simultaneous Detection of Nine Clinically Relevant Antibiotic Resistance Genes in *Staphylococcus aureus*," Journal of Clinical Microbiology, 2003, vol. 41 (9), pp. 4089-4094.
Studdert M.J., et al., "Polymerase Chain Reaction Tests for the Identification of Ross River, Kunjinand Murray Valley Encephalitis Virus Infections in Horses," Australian Veterinary Journal, 2003, vol. 81 (1-2), pp. 76-80.
Stuhlmeier R., et al., "Fast, Simultaneous, and Sensitive Detection of Staphylococci," Journal of Clinical Pathology, 2003, vol. 56 (10), pp. 782-785.
Sumner J.W., et al., "PCR Amplification and Comparison of Nucleotide Sequences from the groESL Heat Shock Operon of Ehrlichia Species," Journal of Critical Microbiology, 1997, vol. 35 (8), pp. 2087-2092.
Sundsfjord A., et al., "Genetic Methods for Detection of Antimicrobial Resistance," APMIS : Acta Pathologica, Microbiologica, et Immunologica Scandinavica, 2004, vol. 112 (11-12), pp. 815-837.
Supplementary European Search Report for Application No. EP02709785.6, mailed on Oct. 12, 2005, 17 pages.
Supplementary European Search Report for Application No. EP03796752.8, mailed on Aug. 7, 2007, 3 pages.
Supplementary European Search Report for Application No. EP03810055.8, mailed on Jun. 8, 2007, 4 pages.
Supplementary European Search Report for Application No. EP03814656, mailed on Oct. 16, 2007, 2 pages.
Supplementary European Search Report for Application No. EP04752257.8, mailed on Feb. 15, 2006, 2 pages.
Supplementary European Search Report for Application No. EP05753037, mailed on Aug. 21, 2009, 2 pages.
Supplementary European Search Report for European Application No. 04775904.8, mailed on Jul. 7, 2008, 8 pages.
Supplementary Partial European Search Report for Application No. EP05751872.2, mailed on Jan. 28, 2008, 8 pages.
Supplementary Partial European Search Report for Application No. EP05856582.1, mailed on Oct. 27, 2008, 10 pages.
Swaminathan B., et al., "PulseNet: The Molecular Subtyping Network for Foodborne Bacterial Disease Surveillance, United States," Emerging Infectious Diseases, 2001, vol. 7 (3), pp. 382-389.
Swanborg R.H., et al., "Human Herpesvirus 6 and Chlamydia Pneumoniae as Etiologic Agents in Multiplesclerosis—a Critical Review," Microbes and Infection/Institut Pasteur, 2002, vol. 4 (13), pp. 1327-1333.
Swenson J.M., et al., "Performance of Eight Methods, Including Two New Rapid Methods, for Detection of Oxacillin Resistance in a Challenge Set of Staphylococcus Aureus Organisms," Journal of Clinical Microbiology, 2001, vol. 39 (10), pp. 3785-3788.
Takagaki Y., et al., "Four Factors are Required for 3'-End Cleavage of Pre-mRNAs," Genes and Development, 1989, vol. 3 (11), pp. 1711-1724.
Takahata M., et al., "Mutations in the GyrA and Gr1A Genes of Quinolone-Resistant Clinical Isolates of Methicillin-Resistant Staphylococcus Aureus," The Journal of Antimicrobial Chemotherapy, 1996, vol. 38 (3), pp. 543-546.
Takayama R., et al., "Quantification of Adenovirus Species B and C Viremia by Real-Time PCR in Adults and Children Undergoing Stem Cell Transplantation," Journal of Medical Virology, 2007, vol. 79 (3), pp. 278-284.
Talaat A.M., et al., "Genome-Directed Primers for Selective Labeling of Bacterial Transcripts for DNA Microarray Analysis," Nature Biotechnology, 2000, vol. 17, pp. 679-682.
Tan T.Y., "Use of Molecular Techniques for the Detection of Antibiotic Resistance in Bacteria," Expert review of Molecular diagnostics, 2003, vol. 3(1), pp. 93-103.
Tanabe F., et al., "The Properties and Mec a Gene of the Methicillin-Resistant Staphylococcus Aureus Isolated in Fukushima Medical College Hospital," Fukushima Journal of Medical Science, 1993, vol. 39 (1), pp. 35-42.

Tang K., et al., "Detection of 500-Nucleotide DNA by Laser Desorption Mass Spectrometry," Rapid Communications in Mass Spectrometry, 1994, vol. 8 (9), pp. 727-730.
Tang K., et al., Double-Stranded DNA Analysis by Matrix Assisted Laser Desorption/lonization, 42nd ASMS Conference on Mass Spectrometry, 1994.
Tang K., et al., "Matrix-Assisted Laser Desorption/lonization of Restriction Enzyme-Digested DNA," Rapid Communications in Mass Spectrometry, 1994, vol. 8 (2), pp. 183-186.
Tang K., et al., "Matrix-Assisted Laser Desorption/lonization Mass Spectrometry of Oligonucleotides," Dissertation submitted to the Faculty of Vanderbilt University, 1994.
Tarassishin L., et al., "Adenovirus Core Protein VII Displays a Linear Epitope Conserved in a Range of Human Adenoviruses," Journal of General Virology, 1999, vol. 80 (Pt 1), pp. 47-50.
Tarassishin L., et al., "An Epitope on the Adenovirus Fibre Tail is Common to all Human Subgroups," Archives of Virology, 2000, vol. 145 (4), pp. 805-811.
Taubenberger J.K., et al., "Characterization of the 1918 Influenza Virus Polymerase Genes," Nature, 2005, vol. 437 (7060), pp. 889-893.
Taylor L.H., et al., "Risk Factors for Human Disease Emergence," Philosophical Transactions of the Royal Society of London Series B, Biological Sciences, 2001, vol. 356 (1411), pp. 983-989.
Tenover F.C., et al., "Characterization of a Strain of Community-Associated Methicillin-ResistantSlaphylococcus Aureus Widely Disseminated in the United States," Journal of Clinical Microbiology, 2006, vol. 44 (1), pp. 108-118.
Teramura T., et al., "Quantitative Detection of Serum Adenovirus in a Transplant Recipient," Lancet, 2002, vol. 359 (9321), pp. 1945.
Thiel V., et al., "Infectious RNA Transcribed in Vitro from a cDNA Copy of the Human Coronavirus Genome Cloned in Vaccinia Virus," The Journal of General Virology, 2001, vol. 82 (Pt 6), pp. 1273-1281.
Thompson J.D., et al., "Clustal W: Improving the Sensitivity of Progressive Multiple Sequence Alignmen Through Sequence Weighting, Position-Specific Gap Penalties and Weight Matrix Choice," Nucleic Acids Research, 1994, vol. 22 (22), pp. 4673-4680.
Thompson W.W., et al., "Influenza-Associated Hospitalizations in the United States," The Journal of the American Medical Association, 2004, vol. 292 (11), pp. 1333-1340.
Tokue Y., et al., "Comparison of a Polymerase Chain Reaction Assay and a Conventional Microbiologic Method for Detection of Methicillin-Resistant Slaphylococcus Aureus," Antimicrobial Agents and Chemotherapy, 1992, vol. 36 (1), pp. 6-9.
Top FH Jr., "Control of Adenovirus Acute Respiratory Disease in U.S. Army Trainees," The Yale Journal of Biology and Medicine, 1975, vol. 48 (3), pp. 185-195.
Towner K.J., et al., "Development and Evaluation of a PCR-Based Immunoassay for the Rapid Detection of Methicillin-Resistant Staphylococcus Aureus," Journal of Medical Microbiology, 1998, vol. 47 (7), pp. 607-613.
Tsuneyoshi, et al., "Mass Spectrometric Gene Diagnosis of One-Base Substitution from Polymerase Chain Reaction Amplified Human DNA," Rapid Communications in Mass Spectomerty, 1997, vol. 11 (7), pp. 719-722.
Tsunoda T., et al., "Time and Memory Efficient Algorithm for Extracting Palindromic and RepetitiveSubsequences in Nucleic Acid Sequences," Pacific Symposium on Biocomputing, 1999, vol. 4, pp. 202-213.
Udo E.E., et al., "A Chromosomal Location of the MupA Gene in Staphylococcus Aureus Expressing High-Level Mupirocin Resistance," The Journal of Antimicrobial Chemotherapy, 2003, vol. 51 (5), pp. 1283-1286.
Udo E.E., et al., "Genetic Analysis of Methicillin-Resistant Staphylococcus Aureus Expressing High-and Low-Level Mupirocin Resistance," Journal of Medical Microbiology, 2001, vol. 50 (10), pp. 909-915.
Udo E.E., et al., "Rapid Detection of Methicillin Resistance in Staphylococci Using a Slide Latex Agglutination Kit," International Journal of Antimicrobial Agents, 2000, vol. 15 (1), pp. 19-24.
Unal S., et al., "Detection of Methicillin-Resistant Staphylococci by Using the Polymerase Chain Reaction," Journal of Clinical Microbiology, 1992, vol. 30 (7), pp. 1685-1691.
Upton A., et al., "Mupirocin and Staphylococcus Aureus: A Recent Paradigm of Emerging Antibiotic Resistance," The Journal of Antimicrobial Chemotherapy, 2003, vol. 51 (3), pp. 613-617.
U.S. Appl. No. 60/369,405.
U.S. Appl. No. 60/397,365.
U.S. Appl. No. 60/431,319.
U.S. Appl. No. 60/443,443.
U.S. Appl. No. 60/443,788.
U.S. Appl. No. 60/447,529.
U.S. Appl. No. 60/453,607.
U.S. Appl. No. 60/461,494.
U.S. Appl. No. 60/470,175.
U.S. Appl. No. 60/501,926.
U.S. Appl. No. 60/509,911.
U.S. Appl. No. 60/604,329.
U.S. Appl. No. 60/615,387.
U.S. Appl. No. 60/658,248.
U.S. Appl. No. 60/701,404.
U.S. Appl. No. 60/705,631.
U.S. Appl. No. 60/720,843.
U.S. Appl. No. 60/747,607.
U.S. Appl. No. 60/771,101.
U.S. Appl. No. 60/773,124.
U.S. Appl. No. 60/891,479.
U.S. Appl. No. 60/941,641.
Vabret A., et al., "Development of a PCR-and Hybridization-Based Assay (PCR Adenovirus Consensus) for the Detection and the Species Identification of Adenoviruses in Respiratory Specimens," Journal of Clinical Virology, 2004, vol. 31 (2), pp. 116-122.
Van Der Zee H., et al., "Rapid and Alternative Screening Methods for Microbiological Analysis," Journal of AOAC International, 1997, vol. 80 (4), pp. 934-940.
Van Dinten L.C., et al., "Proteolytic Processing of the Open Reading Frame Ib-EncodedPart of Arterivirus Replicase Is Mediated by nsp4 Serine Protease and is Essential for Virus Replication," Journal of Virology, 1999, vol. 73 (3), pp. 2027-2037.
Van Elden L.J., et al., "Clinical Diagnosis of Influenza Virus Infection: Evaluation of Diagnostic Tools in General Practice," The British Journal of General Practice, 2001, vol. 51 (469), pp. 630-634.
Van Elden L.J., et al., "Simultaneous Detection of Influenza Viruses A and B Using Real-Time Quantitative PCR," Journal of Clinical Microbiology, 2001, vol. 39 (1), pp. 196-200.
Van Leeuwen W.B., et al., "Multilocus Sequence Typing of Staphylococcus Aureus with DNA Array Technology," Journal of Clinical Microbiology, 2003, vol. 41 (7), pp. 3323-3326.
Van Leeuwen W.B., et al., "Rapid Detection of Methicillin-Resistance in Staphylococcus Aureus Isolates by the MRSA-Screen Latex Agglutination Test," Journal of Clinical Microbiology, 1999, vol. 37 (9), pp. 3029-3030.
Vanchiere J.A., et al., "Detection of BK Virus and Simian Virus 40 in the Urine of Healthy Children," Journal of Medical Virology, 2005, vol. 75 (3), pp. 447-454.
Vannuffel P., et al., "Rapid and Specific Molecular Identification of Methicillin-Resistant *Staphylococcus aureus* in Endotracheal Aspirates from Mechanically Ventilated Patients," Journal of Clinical Microbiology, 1998, vol. 36 (8), pp. 2366-2368.
Vannuffel P., et al., "Specific Detection of Methicillin-Resistant Staphylococcus Species by Multiplex PCR," Journal of Clinical Microbiology, 1995, vol. 33 (11), pp. 2864-2867.
Verma S., et al., "Modified Oligonucleotides: Synthesis and Strategy for Users," Annual Review of Biochemistry, 1998, pp. 99-134.
Videla C., et al., "Genomic Analysis of Adenovirus Isolated from Argentinian Children with Acute Lower Respiratory Infections," Journal of Clinical Virology, 1999, vol. 14 (1), pp. 67-71.
Vilchez R.A. et al., "Detection of Polyomavirus Simian Virus 40 Tumor Antigen DNA in Aids-Related Systemic Non-Hodgkin Lymphoma," Journal of Acquired Immune Deficiencysyndromes, 2002, vol. 29 (2), pp. 109-116.
Voelter C., et al., "Screening Human Tumor Samples with a Broad-Spectrum Polymerase Chain Reaction Method for the Detection of Polyomaviruses," Virology, 1997, vol. 237 (2), pp. 389-396.

Volokhov D., et al., "Microarray Analysis of Erythromycin Resistance Determinants," Journal of Applied Microbiology, 2003, vol. 95 (4), pp. 787-798.
Von Eiff C., et al., "Pathogenesis of Infections Due to Coagulase-Negative Staphylococci," The Lancet Infectious Diseases, 2002, vol. 2 (11), pp. 677-685.
Von Wintzingerode F., et al., "Base-Specific Fragmentation of Amplified 16S rRNA Genes Analyzed by Mass Spectrometry: A Tool for Rapid Bacterial Identification," Proceedings of the National Academy of Sciences, 2002, vol. 99 (10), pp. 7039-7044.
Walker E.S., et al., "A Decline in Mupirocin Resistance in Methicillin-Resistant *Staphylococcus aureus* Accompanied Administrative Control of Prescriptions," Journal of Clinical Microbiology, 2004, vol. 42 (6), pp. 2792-2795.
Wallace S.S., et al., "The Enigma of Endonuclease Viii," DNA Repair, 2003, vol. 2 (5), pp. 441-453.
Wallet F., et al., "Choice of a Routine Method for Detecting Methicillin-Resistance in Staphylococci," The Journal of Antimicrobial Chemotherapy, 1996, vol. 37 (5), pp. 901- 909.
Wang G., et al., "Targeted Mutagenesis in Mammalian Cells Mediated by Intracellular Triple Helix Formation," Molecular and Cellular Biology, 1995, vol. 15 (3), pp. 1759-1768.
Ward C.L., et al., "Design and Performance Testing of Quantitative Real Time PCR Assays for Influenza A and B Viral Load Measurement," Journal of Clinical Virology, 2004, vol. 29 (3), pp. 179-188.
Watanabe K., et al., "ICB Database: the gyrB Database for Identification and Classification of Bacteria," Nucleic Acids Research, 2001, vol. 29 (1), pp. 344-345.
Weissenbacher M., et al., "Etiologic and Clinical Evaluation of Acute Lower Respiratory TractInfections in Young Argentinean Children: An Overview," Reviews of Infectious Diseases, 1990, vol. 12 (Suppl 8), pp. S889-S898.
Wertheim H.F., et al., "Effect of Mupirocin Treatment on Nasal, Pharyngeal, and Perineal Carriage of Staphylococcus Aureus in Healthy Adults," Antimicrobial Agents and Chemotherapy, 2005, vol. 49 (4), pp. 1465-1467.
Westermann P., et al., "Inhibition of Expression of SV40 Virus Large T-Antigen by Antisense Oligodeoxyribonucleotides," Biomedica Biochimica Acta, 1989, vol. 1, pp. 85-93.
Whiley D.M., et al., "Simultaneous Detection and Differentiation of Human Polyomaviruses JC and BK by a Rapid and Sensitive PCR-ELAHA Assay and a Survey of the JCV Subtypes within an Australian Population," Journal of Medical Virology, 2004, vol. 72 (3), pp. 467-472.
Wichelhaus T.A., et al., "Rapid Detection of Epidemic Strains of Methicillin-ResistantStaphylococcus Aureus," Journal of Clinical Microbiology, 1999, vol. 37 (3), pp. 690-693.
Wickham T.J., "Targeting Adenovirus," Gene Therapy, 2000, vol. 7 (2), pp. 110-114.
Widjojoatmodjo M.N., et al., "The Magnetic Immuno Polymerase Chain Reaction Assay for Direct Detection of Salmonellae in Fecal Samples," Journal of Clinical Microbiology, 1992, vol. 30 (12), pp. 3195-3199.
Winger B.E., et al., "High Resolution Accurate Mass Measurements of Biomolecules using a new Electrospray Ionization Ion Cyclotron Resonance Mass Spectrometer," Journal American Society for Mass Spectrometry, 1993, vol. 4 (7), pp. 566-577.
Wood S.R., et al., "Rapid Detection and Serotyping of Adenovirus by Direct Immunofluorescence," Journal of Medical Virology, 1997, vol. 51 (3), pp. 198-201.
Wright K.E., et al., "Typing and Subtyping of Influenza Viruses in Clinical Samples by PCR," Journal of Clinical Microbiology, 1995, vol. 33 (5), pp. 1180-1184.
Written Opinion for Application No. PCT/US2004/33742, mailed on May 15, 2006, 5 pages.
Wu S., et al., "Genetic Organization of the mecA Region in Methicillin-Susceptible and Methicillin-Resistant Strains of Staphylococcus Sciuri," The Journal of Bacteriology, 1998, vol. 180 (2), pp. 236-242.
Wu X., et al., "Establishment of a Fluorescent Polymerase Chain Reaction Method for the Detection of SARS-Associated Coronavhus and its Clinical Application," Chinese Medical Journal, 2003, vol. 116 (7), pp. 988-990.
Xu L., et al., "Electrospray Mass Tag Dideoxy DNA Sequencing," Analytical Chemistry, , 1997, vol. 69 (17), pp. 3595-3602.
Xu W., et al., "Species-Specific Identification of Human Adenoviruses by a Multiplex PCR Assay," Journal of Clinical Microbiology, 2000, vol. 38 (11), pp. 4114-4120.
Xu W., et al., "Type-Specific Identification of Human Adenovirus, 3, 7, and 21 by a Multiplex PCR Assay," Journal of Medical Virology, 2001, vol. 64 (4), pp. 537-542.
Xu X., et al., "Intercontinental Circulation of Human Influenza A(H1N2) Reassortant Viruses During the 2001-2002 Influenza Season," The Journal of Infectious Diseases, 2002, vol. 186 (10), pp. 1490-1493.
Ye K., et al., "Three Distinct Promoters Direct Transcription of Different 5' Untranslated Regions of the Human Interleukin 1 Type 1 Receptor. A Possible Mechanism for Control of Translation," Cytokine, 1996, vol. 8 (6), pp. 421-429.
Yun H.J., et al., "Increased Antibacterial Activity of OW286, A Novel Fluoronaphthyridone Antibiotic, Against Staphylococcus Aureus Strains with Defined Mutations in DNA Gyrase and Toposiomerase IV," International Journal of Antimicrobial Agents, 2005, vol. 25 (4), pp. 334-337.
Zhang J., et al., "PowerBLAST: A New Network BLAST Application for Interactive or Automated Sequence Analysis and Annotation," Genome Research, 1997, vol. 7 (6), pp. 649-656.
Zhang K., et al., "New Quadriplex PCR Assay for Detection of Methicillin and Mupirocin Resistance and Simultaneous Discrimination of Staphylococcus Aureus from Coagulase-Negative Staphylococci," Journal of Clinical Microbiology, 2004, vol. 42 (11), pp. 4947-4955.
Zhang W.D., et al., "Detection and Identification of Human Influenza Viruses by the Polymerase Chain Reaction," Journal of Virological Methods, 1991, vol. 33 (1-2), pp. 165-189.
Zhang Y.Q., et al., "Genome-Based Analysis of Virulence Genes in a Non-Biofilm-Forming Staphylococcus Epidemidis Strain (ATCC 12228)," Molecular Microbiology, 2003, vol. 49 (6), pp. 1577-1593.
Ex Parte Re-Examination Certificate for U.S. Appl. No. 90/010,447 mailed Feb. 15, 2011.
Office Action mailed Feb. 16, 2011 for U.S. Appl. No. 11/929,910 filed Oct. 30, 2007.
Office Action mailed Jan. 6, 2011 for Israel Application No. 157661.
Office Action mailed Mar. 14, 2011 in U.S. Appl. No. 11/930,002.
Office Action mailed Dec. 15, 2010 in Canadian Patent Application No. 2,508,726.
Butler J.M., et al., High Throughput Genotyping of Forensic STRs and SNPs using Time-of-Flight Mass Spectrometry, 9th International Symposium on Human Identification, 1998, Orlando FL.
Deyde V.M., et al., "Genomic Signature-Based Identification of Influenza A Viruses Using RT-PCR/Electro-Spray Ionization Mass Spectrometry (ESI-MS) Technology," PLoS One, 2010, vol. 5 (10), pp. e13293.
European Search Report for Application No. EP10175659.1, mailed on Feb. 9, 2011, 4 pages.
Extended European Search Opinion for Application No. EP10175659.1, mailed on Feb. 21, 2011.
Extended European Search Report for Application No. EP10179789.2, mailed on Mar. 22, 2011, 9 pages.
Extended European Search Report for Application No. EP10179791.8, mailed on Mar. 17, 2011, 7 pages.
Extended European Search Report for Application No. EP10179795.9, mailed on Mar. 22, 2011, 9 pages.
Final Office Action mailed Apr. 14, 2011 for U.S. Appl. No. 12/049,949 filed Mar. 17, 2008.
Notice of Allowance mailed Apr. 1, 2011 for U.S. Appl. No. 11/233,630 filed Sep. 21, 2005.
Notice of Allowance mailed May 25, 2011 for U.S. Appl. No. 11/929,707 filed Oct. 30, 2007.
Office Action mailed Mar. 24, 2011 for U.S. Appl. No. 11/929,930 filed Oct. 30, 2007.
Ross P., et al., "High Level Multiplex Genotyping by MALDI-TOF Mass Spectrometry," Nature Biotechnology, 1998, vol. 16 (13), pp. 1347-1351.

* cited by examiner

METHODS FOR RAPID IDENTIFICATION AND QUANTITATION OF NUCLEIC ACID VARIANTS

RELATED APPLICATIONS

The present application claims the benefit of priority to U.S. Provisional Application Ser. No. 60/701,404, filed Jul. 21, 2005; to U.S. Provisional Application Ser. No. 60/771,101, filed Feb. 6, 2006; and to U.S. Provisional Application Ser. No. 60/747,607 filed May 18, 2006. Each of the above listed U.S. Provisional Applications is incorporated herein by reference in entirety. Methods disclosed in U.S. application Ser. Nos. 10/156,608, 09/891,793, 10/418,514, 10/660,997, 10/660,122, 10,660,996, 10/660,998, 10/728,486, 10/405,756, 10/853,660, 11/060,135, 11/073,362 and 11/209,439, are commonly owned and incorporated herein by reference in their entirety for any purpose.

REFERENCE TO THE SEQUENCE LISTING

Reference is made to the sequence listing submitted via EFS-Web, which consists of a file named "DIBIS007.txt" (33,662 bytes), created on Feb. 3, 2010, the contents of which are incorporated herein by reference.

FIELD OF THE INVENTION

The present invention relates generally to the field of nucleic acid analysis and provides methods, compositions and kits useful for this purpose when combined with mass spectrometry.

BACKGROUND OF THE INVENTION

Characterization of nucleic acid variants is a problem of great importance in various fields of molecular biology such as, for example, genotyping and identification of strains of bacteria and viruses which are subject to evolutionary pressures via mechanisms including mutation, natural selection, genetic drift and recombination. Nucleic acid heterogeneity is a common feature of RNA viruses, for example. Populations of RNA viruses often exhibit high levels of heterogeneity due to mutations which enhance the ability of the viruses to adapt to growth conditions. Mixed populations of RNA virus quasispecies are known to exist in viral vaccines. It would be advantageous to have a method for monitoring the heterogeneity of viral vaccines. Likewise, new strains of bacterial species are also known to evolve rapidly.

Characterization and quantitiation of newly-evolving bacteria and viruses such as the SARS coronavirus, for example, is typically the first step in containment of an epidemic or infectious disease outbreak. In addition to characterization of naturally occurring variants of bacteria and viruses, there is a need for characterization of genetically engineered bacterial or viral bio-weapons in forensic or bio-warfare investigations. Unfortunately, the process of sequencing entire bacterial or viral genomes or vaccine vector sequences is time consuming and is not effective at resolving mixtures of nucleic acid variants.

Mitochondrial DNA is found in eukaryotes and differs from nuclear DNA in its location, its sequence, its quantity in the cell, and its mode of inheritance. The nucleus of the human cell contains two sets of 23 chromosomes, one paternal set and one maternal set. However, cells may contain hundreds to thousands of mitochondria, each of which may contain several copies of mitochondrial DNA. Nuclear DNA has many more bases than mitochondrial DNA, but mitochondrial DNA is present in many more copies than nuclear DNA. This characteristic of mitochondrial DNA is useful in situations where the amount of DNA in a sample is very limited. Typical sources of DNA recovered from crime scenes include hair, bones, teeth, and body fluids such as saliva, semen, and blood.

In humans, mitochondrial DNA is inherited strictly from the mother (Case J. T. and Wallace, D. C., *Somatic Cell Genetics,* 1981, 7, 103-108; Giles, R. E. et al. Proc. Natl. Acad. Sci. 1980, 77, 6715-6719; Hutchison, C. A. et al. *Nature,* 1974, 251, 536-538). Thus, the mitochondrial DNA sequences obtained from maternally related individuals, such as a brother and a sister or a mother and a daughter, will exactly match each other in the absence of a mutation. This characteristic of mitochondrial DNA is advantageous in missing persons cases as reference mitochondrial DNA samples can be supplied by any maternal relative of the missing individual (Ginther, C. et al. *Nature Genetics,* 1992, 2, 135-138; Holland, M. M. et al. *Journal of Forensic Sciences,* 1993, 38, 542-553; Stoneking, M. et al. *American Journal of Human Genetics,* 1991, 48, 370-382).

The human mitochondrial DNA genome is approximately 16,569 bases in length and has two general regions: the coding region and the control region. The coding region is responsible for the production of various biological molecules involved in the process of energy production in the cell and includes about 37 genes (22 transfer RNAs, 2 ribosomal RNAs, and 13 peptides), with very little intergenic sequence and no introns. The control region is responsible for regulation of the mitochondrial DNA molecule. Two regions of mitochondrial DNA within the control region have been found to be highly polymorphic, or variable, within the human population (Greenberg, B. D. et al. *Gene,* 1983, 21, 33-49). These two regions are termed "hypervariable Region I" (HV1), which has an approximate length of 342 base pairs (bp), and "hypervariable Region II" (HV2), which has an approximate length of 268 bp. Forensic mitochondrial DNA examinations are performed using these two hypervariable regions because of the high degree of variability found among individuals.

There exists a need for rapid identification of humans wherein human remains and/or biological samples are analyzed. Such remains or samples may be associated with war-related casualties, aircraft crashes, and acts of terrorism, for example. Analysis of mitochondrial DNA enables a rule-in/rule-out identification process for persons for whom DNA profiles from a maternal relative are available. Human identification by analysis of mitochondrial DNA can also be applied to human remains and/or biological samples obtained from crime scenes.

The process of human identification is a common objective of forensics investigations. As used herein, "forensics" is the study of evidence discovered at a crime or accident scene and used in a court of law. "Forensic science" is any science used for the purposes of the law, in particular the criminal justice system, and therefore provides impartial scientific evidence for use in the courts of law, and in a criminal investigation and trial. Forensic science is a multidisciplinary subject, drawing principally from chemistry and biology, but also from physics, geology, psychology and social science, for example.

Forensic scientists generally use the two hypervariable regions of human mitochondrial DNA for analysis. These hypervariable regions, or portions thereof, provide only one non-limiting example of a region of mitochondrial DNA useful for identification analysis.

A typical mitochondrial DNA analysis begins when total genomic and mitochondrial DNA is extracted from biological material, such as a tooth, blood sample, or hair. The polymerase chain reaction (PCR) is then used to amplify, or create many copies of, the two hypervariable portions of the non-coding region of the mitochondrial DNA molecule, using flanking primers. When adequate amounts of PCR product are amplified to provide all the necessary information about the two hypervariable regions, sequencing reactions are performed. Where possible, the sequences of both hypervariable regions are determined on both strands of the double-stranded DNA molecule, with sufficient redundancy to confirm the nucleotide substitutions that characterize that particular sample. The entire process is then repeated with a known sample, such as blood or saliva collected from a known individual. The sequences from both samples are compared to determine if they match. Finally, in the event of an inclusion or match, The Scientific Working Group on DNA Analysis Methods (SWGDAM) mitochondrial DNA database, which is maintained by the FBI, is searched for the mitochondrial sequence that has been observed for the samples. The analysts can then report the number of observations of this type based on the nucleotide positions that have been read. A written report can be provided to the submitting agency. This process is described in more detail in M. M. Holland and T. J. Parsons 1999, Forensic Science Review, volume 11, pages 25-51.

Approximately 610 bp of mitochondrial DNA are currently sequenced in forensic mitochondrial DNA analysis. Recording and comparing mitochondrial DNA sequences would be difficult and potentially confusing if all of the bases were listed. Thus, mitochondrial DNA sequence information is recorded by listing only the differences with respect to a reference DNA sequence. By convention, human mitochondrial DNA sequences are described using the first complete published mitochondrial DNA sequence as a reference (Anderson, S. et al., *Nature,* 1981, 290, 457-465). This sequence is commonly referred to as the Anderson sequence. It is also called the Cambridge reference sequence or the Oxford sequence. Each base pair in this sequence is assigned a number. Deviations from this reference sequence are recorded as the number of the position demonstrating a difference and a letter designation of the different base. For example, a transition from A to G at position 263 would be recorded as 263 G. If deletions or insertions of bases are present in the mitochondrial DNA, these differences are denoted as well.

In the United States, there are seven laboratories currently conducting forensic mitochondrial DNA examinations: the FBI Laboratory; Laboratory Corporation of America (LabCorp) in Research Triangle Park, N.C.; Mitotyping Technologies in State College, Pennsylvania; the Bode Technology Group (BTG) in Springfield, Va.; the Armed Forces DNA Identification Laboratory (AFDIL) in Rockville, Md.; BioSynthesis, Inc. in Lewisville, Tex.; and Reliagene in New Orleans, La.

Mitochondrial DNA analyses have been admitted in criminal proceedings from these laboratories in the following states as of April 1999: Alabama, Arkansas, Florida, Indiana, Illinois, Maryland, Michigan, New Mexico, North Carolina, Pennsylvania, South Carolina, Tennessee, Texas, and Washington. Mitochondrial DNA has also been admitted and used in criminal trials in Australia, the United Kingdom, and several other European countries.

Since 1996, the number of individuals performing mitochondrial DNA analysis at the FBI Laboratory has grown from 4 to 12, with more personnel expected in the near future. Over 150 mitochondrial DNA cases have been completed by the FBI Laboratory as of March 1999, and dozens more await analysis. Forensic courses are being taught by the FBI Laboratory personnel and other groups to educate forensic scientists in the procedures and interpretation of mitochondrial DNA sequencing. More and more individuals are learning about the value of mitochondrial DNA sequencing for obtaining useful information from evidentiary samples that are small, degraded, or both. Mitochondrial DNA sequencing is becoming known not only as an exclusionary tool but also as a complementary technique for use with other human identification procedures. Mitochondrial DNA analysis will continue to be a powerful tool for law enforcement officials in the years to come as other applications are developed, validated, and applied to forensic evidence.

Presently, the forensic analysis of mitochondrial DNA is rigorous and labor-intensive. Currently, only 1-2 cases per month per analyst can be performed. Several molecular biological techniques are combined to obtain a mitochondrial DNA sequence from a sample. The steps of the mitochondrial DNA analysis process include primary visual analysis, sample preparation, DNA extraction, polymerase chain reaction (PCR) amplification, post-amplification quantification of the DNA, automated DNA sequencing, and data analysis. Another complicating factor in the forensic analysis of mitochondrial DNA is the occurrence of heteroplasmy wherein the pool of mitochondrial DNAs in a given cell is heterogeneous due to mutations in individual mitochondrial DNAs. There are different forms of heteroplasmy found in mitochondrial DNA. For example, sequence heteroplasmy (also known as point heteroplasmy) is the occurrence of more than one base at a particular position or positions in the mitochondrial DNA sequence. Length heteroplasmy is the occurrence of more than one length of a stretch of the same base in a mitochondrial DNA sequence as a result of insertion of nucleotide residues.

Heteroplasmy is a problem for forensic investigators since a sample from a crime scene can differ from a sample from a suspect by one base pair and this difference may be interpreted as sufficient evidence to eliminate that individual as the suspect. Hair samples from a single individual can contain heteroplasmic mutations at vastly different concentrations and even the root and shaft of a single hair can differ. The detection methods currently available to molecular biologists cannot detect low levels of heteroplasmy. Furthermore, if present, length heteroplasmy will adversely affect sequencing runs by resulting in an out-of-frame sequence that cannot be interpreted.

Mass spectrometry provides detailed information about the molecules being analyzed, including high mass accuracy. It is also a process that can be easily automated.

There is a need for a mitochondrial DNA forensic analysis which is both specific and rapid, and in which no nucleic acid sequencing is required. There is also a need for a method of rapid characterization and quantitation of nucleic acids which have variant positions relative to a reference sequence. These needs, as well as others, are addressed herein below.

SUMMARY OF THE INVENTION

Described herein are compositions and methods for analyzing a nucleic acid by performing the steps of obtaining a sample of nucleic acid for base composition analysis; selecting at least two primer pairs that will generate overlapping amplification products of at least two sub-segments of the nucleic acid; amplifying at least two nucleic acid sequences of a region of the nucleic acid designated as a target for base composition analysis using the primer pairs, thereby generating at least two overlapping amplification products; obtaining base compositions of the amplification products by measuring molecular masses of one or more of the amplification products using a mass spectrometer; and converting one or more of the measured molecular masses to base compositions; comparing one or more of the base compositions with one or more base compositions of reference sub-segments of a reference sequence; and identifying the presence of a particular nucleic acid sequence or variant thereof.

The nucleic acid analyzed is obtained from a human, bacterium, virus, fungus, synthetic nucleic acid source, recombinant nucleic acid source, or encodes a biological product such as a vaccine, antibody or other biological product.

Further described herein are compositions and methods for identifying a human by obtaining a sample comprising mitochondrial DNA of the human for base composition analysis; selecting at least two primer pairs that will generate overlapping amplification products representing overlapping sub-segments of the mitochondrial DNA; amplifying at least two nucleic acid sequences of a region of the mitochondrial DNA designated as a target for base composition analysis using the at least two primer pairs, thereby generating at least two overlapping amplification products; obtaining base compositions of the amplification products by measuring molecular masses of one or more of the amplification products generated using a mass spectrometer and converting one or more of the measured molecular masses to base compositions; and comparing one or more of the base compositions with one or more base compositions of reference sub-segments of a reference sequence thereby identifying the human.

Also described herein are compositions and methods for characterizing heteroplasmy of mitochondrial DNA comprising the steps of obtaining a sample comprising mitochondrial DNA for base composition analysis; selecting at least two primer pairs that will generate overlapping amplification products representing sub-segments of the mitochondrial DNA; amplifying at least two nucleic acid sequences of a region of the mitochondrial DNA designated as a target for base composition analysis using the at least two primer pairs, thereby generating at least two overlapping amplification products; obtaining base compositions of the amplification products by measuring molecular masses of one or more of the amplification products using a mass spectrometer; and converting one or more of the measured molecular masses to base compositions; comparing one or more of the base compositions with one or more base compositions of reference sub-segments of a reference sequence; and identifying at least two distinct amplification products with distinct base compositions obtained by the same pair of primers, thereby characterizing the heteroplasmy.

Also disclosed are primer pair compositions and kits comprising the same which are useful for obtaining amplification products used in genotyping organisms.

DEFINITIONS

Figure 1:
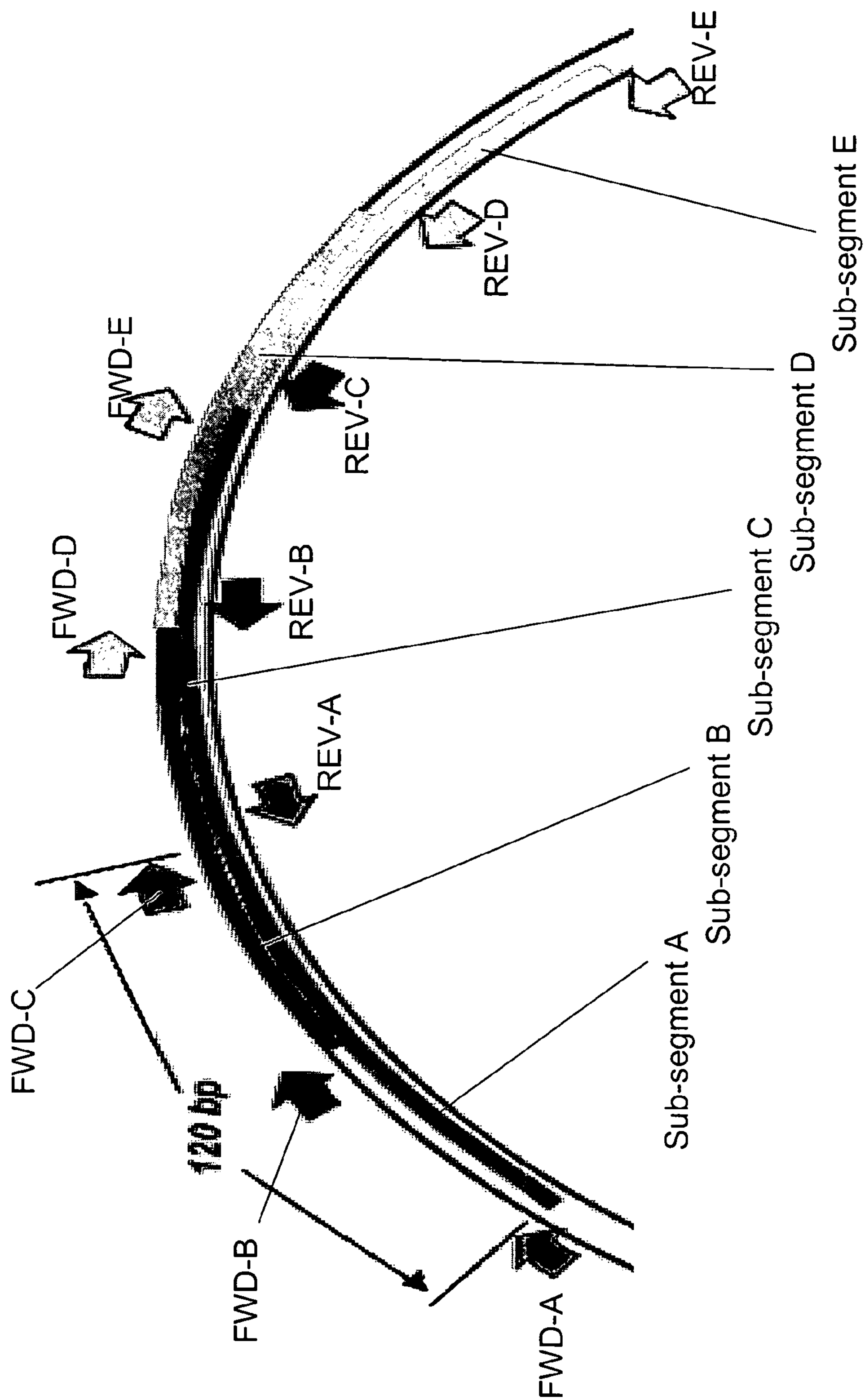
FIG. 1 is a schematic diagram of the definition of sub-segments of a reference sequence for amplification. Arrows indicate the position of primer hybridization for obtaining an amplification product corresponding to a sub-segment. For example, FWD-A indicates the hybridization position of the forward primer for obtaining an amplification product corresponding to Sub-segment A, while REV-A indicates the hybridization position of the reverse primer for obtaining an amplification product corresponding to sub-segment A. Overlap of one sub-segment A, which has a length of 120 nucleobases (bp) with sub-segment B is shown on the left side.

A number of terms and phrases are defined below:

As described herein, nucleic acids are analyzed to generate a base composition profile. Nucleic acids include, but are not limited to, human mitochondrial DNA, human, chromosomal DNA, bacterial genomic DNA, fungal DNA, viral DNA, viral RNA, commercially available plasmids or vectors or vaccines. The nucleic acids are referred to as having regions, which define as being a portion of the nucleic acid that are known or suspected to comprise genetic sequence differences that allow for the characterization of the nucleic acid. By use of the term "characterization" it is meant that the source of the nucleic acid can be identified (e.g., genetic identification of a human, identification of a recombination event in a plasmid, diagnosis of a human genetic disposition towards a disease or trait, HN typing of influenza virus strains). Part or all of a region may form the target for analysis using the disclosed material and methods. Alternatively, an entire nucleic acid can be analyzed, which is typically more useful when there are not defined regions for characterization. Thus, the whole nucleic acid will be referred to herein as region and a target. Within a target there are sub-segments. Sub-segments are the portions of nucleic acid that are flanked by primer to generate individual amplified products or amplicons. These sub-segments preferably overlap.

As used herein, "Mitochondrial DNA" refers to a circular ring of DNA which is separate from chromosomal DNA and contained as multiple copies within mitochondria. Mitochondrial DNA is often abbreviated as "mtDNA" and will be recognized as such by one with ordinary skill in the arts of mitochondrial DNA analysis. In a preferred embodiment, the objective is to identify a human. Nucleic acid is obtained from a human cell, such as a blood cell, hair, cell, skin cell or any other human cell appropriate for obtaining nucleic acid. In some embodiments, the nucleic acid is mitochondrial DNA. In some embodiments, certain portions of mitochondrial DNA are appropriate for base composition analysis such as, for example, HV1 and HV2.

As used herein, the term "HV1" refers to a region within mitochondrial DNA known as "hypervariable region 1." With respect to the reference Anderson/Cambridge mitochondrial DNA sequence, the HV1 region is represented by coordinates 15924 . . . 16428. This region is useful for identification of humans because it has a high degree of variability among different human individuals. In some embodiments, a defined portion of the HV1 region is analyzed by base composition analysis of "sub-segments" of the defined portion. In this embodiment, the defined portion of HV1 represents the "target." In preferred embodiments, the entire HV1 region (coordinates 15924 . . . 16428) is divided into overlapping sub-segments. In this embodiment, the entire HV1 region represents the "target."

As used herein, the term "HV2" refers to a region within mitochondrial DNA known as "hypervariable region 2." With respect to the reference Anderson/Cambridge mitochondrial DNA sequence, the HV1 region is represented by coordinates 31 . . . 576. As for HV1, the HV2 region is useful for identification of humans because it also has a high degree of variability among different human individuals. In some embodiments, a defined portion of the HV2 region is analyzed by base composition analysis of "sub-segments" of the defined portion. In this embodiment, the defined portion of HV2 represents the "target." In preferred embodiments, the entire HV1 region (coordinates 31 . . . 576) is divided into overlapping sub-segments. In this embodiment, the entire HV2 region represents the "target."

In other embodiments, additional target regions within the mitochondrial DNA may be chosen for base composition analysis.

As used herein, the term "target" generally refers to a nucleic acid sequence to be detected or characterized. Thus, the "target" is sought to be sorted out from other nucleic acid sequences.

As used herein, "sub-segments" are portions of a given target which are of useful size for base composition analysis. In some embodiments, the sizes of sub-segments range between about 45 to about 150 nucleobases in length. In preferred embodiments, the "sub-segments" overlap with each other and cover the entire target as shown in FIG. 1. Amplification products representing the sub-segments are obtained by amplification methods, such as PCR that are well known to those with ordinary skill in molecular biology techniques. The amplification products representing the sub-segments are analyzed by mass spectrometry to determine their molecular masses and base compositions of the amplification products are calculated from the molecular masses. The experimentally-determined base compositions are then compared with base compositions of "reference sub-segments" of a "reference nucleic acid" whose sequence and/or base composition is known. In preferred embodiments a database containing base compositions of reference nucleic acids and sub-segments thereof is used for comparison with the experimentally-determined base compositions. A match of one or more experimentally-determined base compositions of one or more sub-segments with one or more base compositions of reference sub-segments will provide the identity of the human.

Figure 4:
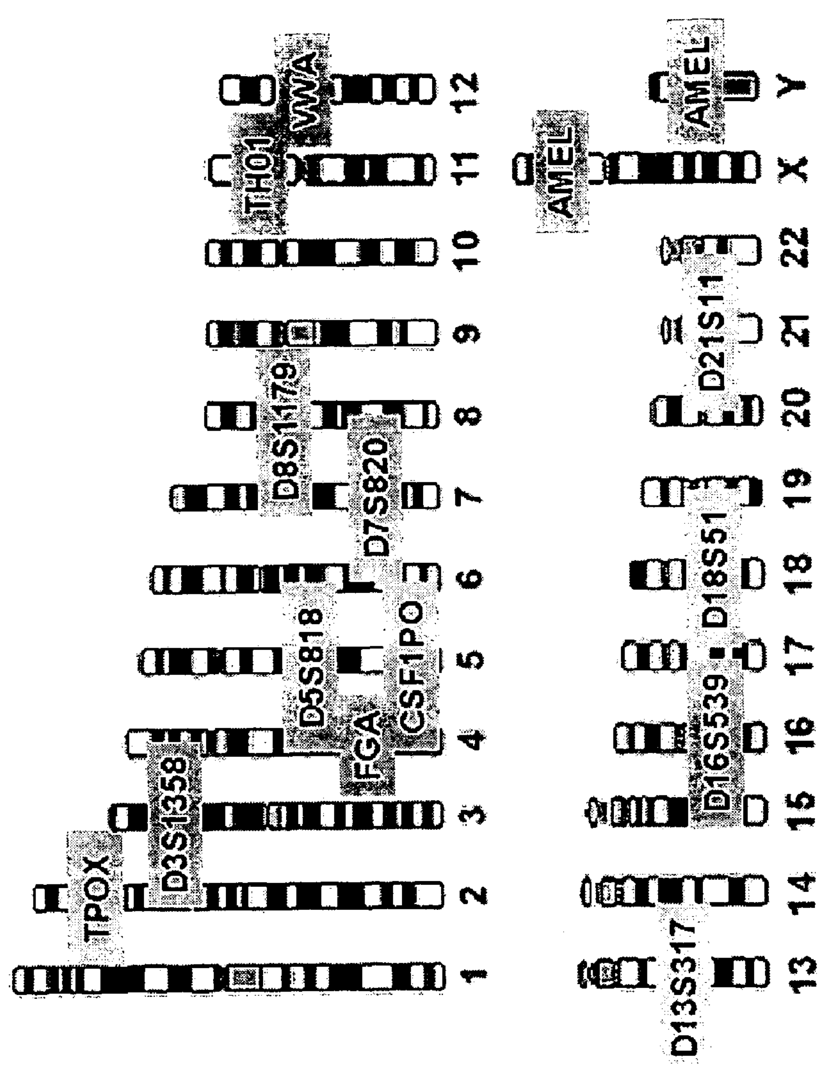
FIG. 4 is an illustration of the names and chromosome locations for the CODIS 13 markers, as well as for the AMEL markers on the X and Y chromosomes. The CODIS 13 short tandem repeats are commonly used by law enforcement for determining the source identity for a given nucleic acid.

The same definitions of the terms "target," "sub-segment," "reference sub-segment" and "reference nucleic acid" are applicable to other preferred embodiments where base composition analysis is used to identify a human by analysis of specific human chromosomal target regions such as CODIS markers for example. FIG. 4 is an illustration of the names and chromosome locations for the CODIS 13 markers, as well as for the AMEL markers on the X and Y chromosomes.

The same definitions of the terms "target," "sub-segment," "reference sub-segment" and "reference nucleic acid" are applicable to other preferred embodiments where base composition analysis is used to identify or characterize a genotype of a microorganism such as a bacterium, virus, or fungus for example. Characterization of genotypes of microorganisms is useful in infectious disease diagnostics for example. In these embodiments, a given target may represent the entire genome of a microorganism or a portion thereof. The target is analyzed by characterization of amplification products representing sub-segments of the target.

The same definitions of the terms "target," "sub-segment," "reference sub-segment" and "reference nucleic acid" are applicable to other preferred embodiments where base composition analysis is used to validate a "test nucleic acid" with respect to a reference nucleic acid. Validation of test nucleic acids is desirable in quality control of pharmaceutical production such as in production of vectors carrying genes encoding therapeutic proteins such as vaccines for example. In this embodiment, the "test nucleic acid" is expected to be identical in sequence and base composition to the reference nucleic acid. Comparison of experimentally determined base compositions of amplification products representing sub-segments of the target with base compositions of reference sub-segments may either indicate that the base compositions are identical, thereby validating the test nucleic acid, or identify a variant of the reference nucleic acid.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity.

Template or target specificity is achieved in-most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (D. L. Kacian et al., Proc. Natl. Acad. Sci. USA 69:3038 [1972]). Other nucleic acid will not be replicated by this amplification enzyme. Similarly, in the case of T7 RNA polymerase, this amplification enzyme has a stringent specificity for its own promoters (Chamberlin et al., Nature 228: 227 [1970]). In the case of T4 DNA ligase, the enzyme will not ligate the two oligonucleotides or polynucleotides, where there is a mismatch between the oligonucleotide or polynucleotide substrate and the template at the ligation junction (D. Y. Wu and R. B. Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), *PCR Technology*, Stockton Press [1989]).

As used herein, the term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally, such as a purified fragment from a restriction digest, or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. Preferably, the primer is sufficiently long to prime the synthesis of extension products in the presence of the inducing agent. The exact lengths of the primers will depend on many factors, including temperature, source of primer and the use of the method. The primers can be any useful length. Lengths of about 13 to about 35 nucleobases are preferred. One with ordinary skill in the art of molecular biology can design primers appropriate for amplification methods.

As used herein, a "pair of primers" or "a primer pair" is used for amplification of a nucleic acid sequence. A pair of primers comprises a forward primer and a reverse primer. The forward primer hybridizes to a sense strand of a target gene sequence to be amplified and primes synthesis of an antisense strand (complementary to the sense strand) using the target sequence as a template. A reverse primer hybridizes to the antisense strand of a target gene sequence to be amplified and primes synthesis of a sense strand (complementary to the antisense strand) using the target sequence as a template.

As used herein, the term "polymerase chain reaction" ("PCR") refers to the method of K. B. Mullis U.S. Pat. Nos. 4,683,195, 4,683,202, and 4,965,188, hereby incorporated by reference, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR").Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the terms "PCR product," "PCR fragment," and "amplification product" refer to the nucleic acid product obtained after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

As used herein, the terms "complementary" or "complementarity" are used in reference to polynucleotides (i.e., a sequence of nucleotides such as an oligonucleotide or a target nucleic acid) related by the base-pairing rules. For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids. Either term may also be used in reference to individual nucleotides, especially within the context of polynucleotides. For example, a particular nucleotide within an oligonucleotide may be noted for its complementarity, or lack thereof, to a nucleotide within another nucleic acid strand, in contrast or comparison to the complementarity between the rest of the oligonucleotide and the nucleic acid strand.

The terms "homology," "homologous" and "sequence identity" refer to a degree of identity. There may be partial homology or complete homology. A partially homologous sequence is one that is less than 100% identical to another sequence. Determination of sequence identity is described in the following example: a primer 20 nucleobases in length which is otherwise identical to another 20 nucleobase primer but having two non-identical residues has 18 of 20 identical residues (18/20=0.9 or 90% sequence identity). In another example, a primer 15 nucleobases in length having all residues identical to a 15 nucleobase segment of primer 20 nucleobases in length would have 15/20=0.75 or 75% sequence identity with the 20 nucleobase primer. In context of the present invention, sequence identity is meant to be properly determined when the query sequence and the subject sequence are both described in the 5' to 3' direction.

As used herein, the term "hybridization" is used in reference to the pairing of complementary nucleic acids. Hybridization and the strength of hybridization (i.e., the strength of the association between the nucleic acids) is influenced by such factors as the degree of complementary between the nucleic acids, stringency of the conditions involved, and the $T_m$ of the formed hybrid. "Hybridization" methods involve the annealing of one nucleic acid to another, complementary nucleic acid, i.e., a nucleic acid having a complementary nucleotide sequence. The ability of two polymers of nucleic acid containing complementary sequences to find each other and anneal through base pairing interaction is a well-recognized phenomenon. The initial observations of the "hybridization" process by Marmur and Lane, Proc. Natl. Acad. Sci. USA 46:453 (1960) and Doty et al., Proc. Natl. Acad. Sci. USA 46:461 (1960) have been followed by the refinement of this process into an essential tool of modem biology.

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

As used herein, the term "$T_m$" is used in reference to the "melting temperature." The melting temperature is the temperature at which a population of double-stranded nucleic acid molecules becomes half dissociated into single strands. Several equations for calculating the $T_m$ of nucleic acids are well known in the art. As indicated by standard references, a simple estimate of the $T_m$ value may be calculated by the equation: $T_m$=81.5+0.41 (% G+C), when a nucleic acid is in aqueous solution at 1 M NaCl (see e.g., Anderson and Young, Quantitative Filter Hybridization, in Nucleic Acid Hybridization (1985). Other references (e.g., Allawi, H. T. & SantaLucia, J., Jr. Thermodynamics and NMR of internal G.T mismatches in DNA. Biochemistry 36, 10581-94 (1997) include more sophisticated computations which take structural and environmental, as well as sequence characteristics into account for the calculation of $T_m$.

The term "gene" refers to a DNA sequence that comprises control and coding sequences necessary for the production of an RNA having a non-coding function (e.g., a ribosomal or transfer RNA), a polypeptide or a precursor. The RNA or polypeptide can be encoded by a full length coding sequence or by any portion of the coding sequence so long as the desired activity or function is retained.

The term "wild-type" refers to a gene or a gene product that has the characteristics of that gene or gene product when isolated from a naturally occurring source. A wild-type gene is that which is most frequently observed in a population and is thus arbitrarily designated the "normal" or "wild-type" form of the gene. In contrast, the term "modified", "mutant" or "polymorphic" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "oligonucleotide" as used herein is defined as a molecule comprising two or more deoxyribonucleotides or ribonucleotides, preferably at least 5 nucleotides, more preferably at least about 13 to 35 nucleotides. The exact size will depend on many factors, which in turn depend on the ultimate function or use of the oligonucleotide. The oligonucleotide may be generated in any manner, including chemical synthesis, DNA replication, reverse transcription, PCR, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5'-end" if its 5' phosphate is not linked to the 3' oxygen of a mononucleotide pentose ring and as the "3'-end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. A first region along a nucleic acid strand is said to be upstream of another region if the 3' end of the first region is before the 5' end of the second region when moving along a strand of nucleic acid in a 5' to 3' direction. All oligonucleotide primers disclosed herein are understood to be presented in the 5' to 3' direction when reading left to right.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide. Similarly, when two overlapping oligonucleotides are hybridized to the same linear complementary nucleic acid sequence, with the first oligonucleotide positioned such that its 5' end is upstream of the 5' end of the second oligonucleotide, and the 3' end of the first oligonucleotide is upstream of the 3' end of the second oligonucleotide, the first oligonucleotide may be called the "upstream" oligonucleotide and the second oligonucleotide may be called the "downstream" oligonucleotide.

The term "primer" refers to an oligonucleotide that is capable of acting as a point of initiation of synthesis when placed under conditions in which primer extension is initiated. An oligonucleotide "primer" may occur naturally, as in a purified restriction digest or may be produced synthetically. A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

The term "target nucleic acid" refers to a nucleic acid molecule containing a sequence that has at least partial complementarity with an oligonucleotide primer. The target nucleic acid may comprise single- or double-stranded DNA or RNA.

The term "variable sequence" as used herein refers to differences in nucleic acid sequence between two nucleic acids. For example, the same gene of two different bacterial species may vary in sequence by the presence of single base substitutions and/or deletions or insertions of one or more nucleotides. These two forms of the structural gene are said to vary in sequence from one another.

The term "nucleotide analog" as used herein refers to modified or non-naturally occurring nucleotides such as 5-propynyl pyrimidines (i.e., 5-propynyl-dTTP and 5-propynyl-dTCP), 7-deaza purines (i.e., 7-deaza-dATP and 7-deaza-dGTP). Nucleotide analogs include base analogs and comprise modified forms of deoxyribonucleotides as well as ribonucleotides.

The term "microorganism" as used herein means an organism too small to be observed with the unaided eye and includes, but is not limited to bacteria, virus, protozoans, fungi; and ciliates.

The term "microbial gene sequences" refers to gene sequences derived from a microorganism.

The term "bacteria" or "bacterium" refers to any member of the groups of eubacteria and archaebacteria.

The term "virus" refers to obligate, ultramicroscopic, intracellular parasites incapable of autonomous replication (i.e., replication requires the use of the host cell's machinery).

The term "sample" in the present specification and claims is used in its broadest sense. On the one hand it is meant to include a specimen or culture (e.g., microbiological cultures). On the other hand, it is meant to include both biological and environmental samples. A sample may include a specimen of synthetic origin.

Biological samples may be animal, including human, fluid, solid (e.g., stool) or tissue, as well as liquid and solid food and feed products and ingredients such as dairy items, vegetables, meat and meat by-products, and waste. Biological samples may be obtained from all of the various families of domestic animals, as well as feral or wild animals, including, but not limited to, such animals as ungulates, bear, fish, lagamorphs, rodents, etc.

Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

The term "source of target nucleic acid" refers to any sample that contains nucleic acids (RNA or DNA). Particularly preferred sources of target nucleic acids are biological samples including, but not limited to blood, saliva, cerebral spinal fluid, pleural fluid, milk, lymph, sputum and semen. The source of nucleic acid may also be an organism such as a human, animal, bacterium, virus or fungus for example.

The term "polymerization means" or "polymerization agent" refers to any agent capable of facilitating the addition of nucleoside triphosphates to an oligonucleotide. Preferred polymerization means comprise DNA and RNA polymerases.

The term "adduct" is used herein in its broadest sense to indicate any compound or element that can be added to an oligonucleotide. An adduct may be charged (positively or negatively) or may be charge-neutral. An adduct may be added to the oligonucleotide via covalent or non-covalent linkages. Examples of adducts include, but are not limited to, indodicarbocyanine dye amidites, amino-substituted nucleotides, ethidium bromide, ethidium homodimer, (1,3-propanediamino)propidium, (diethylenetriamino)propidium, thiazole orange, (N-N'-tetramethyl-1,3-propanediamino) propyl thiazole orange, (N-N'-tetramethyl-1,2-ethanediamino)propyl thiazole orange, thiazole orange-thiazole orange homodimer (TOTO), thiazole orange-thiazole blue heterodimer (TOTAB), thiazole orange-ethidium heterodimer 1 (TOED1), thiazole orange-ethidium heterodimer 2 (TOED2) and fluorescein-ethidium heterodimer (FED), psoralens, biotin, streptavidin, avidin, etc.

Where a first oligonucleotide is complementary to a region of a target nucleic acid and a second oligonucleotide has complementary to the same region (or a portion of this region) a "region of overlap" exists along the target nucleic acid. The degree of overlap will vary depending upon the nature of the complementarity.

As used herein, the term "purified" or "to purify" refers to the removal of contaminants from a sample.

As used herein the term "portion" when in reference to a protein (as in "a portion of a given protein") refers to fragments of that protein. The fragments may range in size from four amino acid residues to the entire amino acid sequence minus one amino acid (e.g., 4, 5, 6, . . . , n−1).

The term "nucleic acid" or "nucleic acid sequence" as used herein refers to an oligonucleotide, nucleotide or polynucleotide, and fragments or portions thereof, and to DNA or RNA of genomic or synthetic origin which may be single or double stranded, and represent the sense or antisense strand. Similarly, "amino acid sequence" as used herein refers to peptide or protein sequence.

The term "peptide nucleic acid" ("PNA") as used herein refers to a molecule comprising bases or base analogs such as would be found in natural nucleic acid, but attached to a peptide backbone rather than the sugar-phosphate backbone typical of nucleic acids. The attachment of the bases to the peptide is such as to allow the bases to base pair with complementary bases of nucleic acid in a manner similar to that of an oligonucleotide. These small molecules, also designated anti gene agents, stop transcript elongation by binding to their complementary strand of nucleic acid (Nielsen, et al. Anticancer Drug Des. 8:53 63 [1993]).

The term "locked nucleic acid ("LNA") as used herein, refers to a conformationally restricted nucleic acid analogue, in which the ribose ring is locked into a rigid C3'-endo (or Northern-type) conformation by a simple 2'-O, 4'-C methylene bridge. Duplexes involving LNA (hybridized to either DNA or RNA) display a large increase in melting temperatures of between +3.0 to +9.3° C. per LNA modification, in comparison to corresponding unmodified reference duplexes. LNA recognizes both DNA and RNA with remarkable affinities and selectivities. Incorporation of a given number of LNA monomers into oligonucleotides is a very convenient way of vastly improving the stability and specificity of duplexes toward complementary RNA or DNA such as, for example, primer binding regions.

As used herein, the terms "purified" or "substantially purified" refer to molecules, either nucleic or amino acid sequences, that are removed from their natural environment, isolated or separated, and are at least 60% free, preferably 75% free, and most preferably 90% free from other components with which they are naturally associated. An "isolated polynucleotide" or "isolated oligonucleotide" is therefore a substantially purified polynucleotide.

The term "duplex" refers to the state of nucleic acids in which the base portions of the nucleotides on one strand are bound through hydrogen bonding the their complementary bases arrayed on a second strand. The condition of being in a duplex form reflects on the state of the bases of a nucleic acid. By virtue of base pairing, the strands of nucleic acid also generally assume the tertiary structure of a double helix, having a major and a minor groove. The assumption of the helical form is implicit in the act of becoming duplexed.

The term "template" refers to a strand of nucleic acid on which a complementary copy is built from nucleoside triphosphates through the activity of a template-dependent nucleic acid polymerase. Within a duplex the template strand is, by convention, depicted and described as the "bottom" strand. Similarly, the non-template strand is often depicted and described as the "top" strand.

The term "template-dependent RNA polymerase" refers to a nucleic acid polymerase that creates new RNA strands through the copying of a template strand as described above and which does not synthesize RNA in the absence of a template. This is in contrast to the activity of the template-independent nucleic acid polymerases that synthesize or extend nucleic acids without reference to a template, such as terminal deoxynucleotidyl transferase, or Poly A polymerase.

The term "in silico" when used in relation to a process indicates that the process is simulated on or embedded in a computer.

The term "priming region" refers to a region on a target nucleic acid sequence to which a primer hybridizes for the purpose of extension of the complementary strand of the target nucleic acid sequence.

The term "non-templated T residue" as used herein refers to a thymidine (T) residue added to the 5' end of a primer which does not necessarily hybridize to the target nucleic acid being amplified.

The term "genotype" as used herein refers to at least a portion of the genetic makeup of an individual. A portion of a genome can be sufficient for assignment of a genotype to an individual provided that the portion of the genome contains a representative sequence or base composition to distinguish the genotype from other genotypes.

The term "nucleobase" as used herein is synonymous with other terms in use in the art including "nucleotide," "deoxynucleotide," "nucleotide residue," "deoxynucleotide residue," "nucleotide triphosphate (NTP)," or deoxynucleotide triphosphate (dNTP).

As defined herein, "base composition" refers to the numbers of each of the four standard nucleobases that are present within a given standard sequence or corresponding amplification product of a standard, test or variant sequence. Methods including steps of measuring base compositions are disclosed and claimed in commonly owned published U.S. Patent Application Nos: 20030124556, 20030082539, 20040209260, 20040219517, and 20040180328 and U.S. Ser. Nos. 10/728,486, 10/829,826, 10/660,998, 10/853,660, 60/604,329, 60/632,862, 60/639,068, 60/648,188, 11/060, 135, 11/073,362, and 60/658,248, each of which is incorporated herein by reference in entirety.

As used herein, the term "base composition analysis" refers to determination of the base composition of an amplification product representing a sub-segment of a target nucleic acid sequence from the molecular mass of the amplification product determined by mass spectrometry. In embodiments of the present invention, base composition analysis may include determination of base compositions of two or more amplification products representing overlapping sub-segments of a nucleic acid sequence which are to be compared with the defined base compositions of the corresponding overlapping sub-segments of one or more reference nucleic acids As used herein, the term "reference nucleic acid" or "reference nucleic acid segment" is a characterized nucleic acid of known sequence and/or known base composition. A reference nucleic acid segment is compared with uncharacterized sequences in various embodiments of the present invention. For example, a characterized vector or portion thereof can be used as a reference nucleic acid segment. A characterized portion of human nucleic acid may also be used as a reference nucleic acid provided the genotype, identity or race of the human from which the reference nucleic acid is obtained is known. A genome or a portion thereof of a bacterium, virus or fungus may also be employed as a reference nucleic acid provided that the species or genotype of the bacterium, virus or fungus is known.

As used herein, the term "reference base composition" refers to a characterized base composition. For example, a sub-segment of a reference nucleic acid having the defined sequence AAAAATTTTCCCGG (SEQ ID NO: 52) has a standard base composition of $A_5$ $T_4$ $C_3$ $_{G2}$.

As used herein, the term "test nucleic acid sequence" refers to an uncharacterized nucleic acid sequence whose base composition is to be characterized and compared with one or more standard nucleic acid segments.

As used herein, term "overlap" or "overlapping sub-segments" refers to sub-segments of a standard nucleic acid segment which have overlap as illustrated by the following example which employs a standard nucleic acid segment of length of 300 nucleobases. A first sub-segment may, for example, extend from position 1 to position 100. A second sub-segment may, for example, extend from position 60 to position 160, having overlap from position 60 to position 100. A third sub-segment may, for example, extend from position 120 to position 220, having overlap from position 120 to position 160. A fourth sub-segment may, for example, extend from position 180 to position 280, having overlap from position 180 to position 220. Producing sub-segments with overlap is useful because it provides redundancy and reduces the likelihood that sub-segments containing variants relative to a given standard sub-segment will be mischaracterized. If a primer used to amplify a given sub-segment hybridizes to a position with a mutation relative to the reference sequence, the amplification product will not contain the mutation because the primer extension product is used as a subsequent template in subsequent amplification cycles. Thus, having overlap of two sub-segments wherein overlap of the second sub-segment over the first sub-segment extends past the reverse primer hybridization site of the first sub-segment eliminates the possibility that the reverse primer for the first sub-segment will mask a given mutation within the first sub-segment reverse primer hybridization site. The extent of minimal overlap should be determined by the length of the primer hybridization site of a given sub-segment. Generally, overlap of sub-segments by several nucleobases is appropriate but shorter overlap lengths may also be appropriate provided the primer hybridization sites are shorter nucleobases. The avoidance of overlap of primer hybridization sites on overlapping sub-segments is preferred.

As used herein, the term "co-amplification" or "co-amplified" refers to the process of obtaining more than one amplification product in the same amplification reaction mixture using the same pair of primers.

As used herein, the term "vector" refers to a nucleic acid adapted for transfection into a host cell. Examples of vectors include, but are not limited to, plasmids, cosmids, bacteriophages and the like.

As used herein, the term "therapeutic protein" refers to any protein product produced by biotechnological methods for use as a therapeutic product. Examples of therapeutic proteins include, but are not limited to protein products such as vaccines, antibodies, structural proteins, hormones, and cell signaling proteins such as receptors, cytokines and the like.

As used herein, the term "recombinant" refers to having been created by genetic engineering. For example, a "recombinant insert" refers to a nucleic acid segment inserted into another nucleic acid sequence using techniques well known to those with ordinary skill in the arts of genetic engineering and molecular biology.

A "nucleic acid variant" is herein defined as a nucleic acid having substantial similarity or sequence identity with a "standard" nucleic acid sequence. For example, between about 70% up to but not including 100% sequence identity.

As used herein, a "triplex combination of primer pairs" refers to three primer pairs which is to be included in an amplification mixture for the purpose of obtaining three distinct amplification products from a given target nucleic acid.

DESCRIPTION OF EMBODIMENTS

Provided herein are compositions and methods for determining the presence of a nucleic acid variant or a genotype relative to a known and defined "reference" nucleic acid sequence. Identification of a distinct genotype in certain embodiments is satisfied by identification of a distinct base composition of a given sub-segment of a target nucleic acid.

In the methods described herein where the genotype, and in turn the identity, of a nucleic acid sample is determined, the nucleic acid is measured to deliver a base composition profile. That measured base composition profile is then compared to a reference base composition profile that is further associated with an identity. The reference base composition can be a head-to-head comparison or a standard reference database. In both the head-to-head comparison and the standard reference database comparison, the unknown sample is analyzed using the disclosed compositions and methods to generate a measured base composition profile. For the head-to-head comparison, the reference base composition profile is generated by similarly analyzing samples from a selected suspect population using the disclosed compositions and methods. The measured base composition is then compared to the reference base compositions and if a match occurs between the unknown and a suspect, then the identity is determined. In the standard reference database comparison the measured base composition is compared to a pre-existing database of reference base compositions. This database can be populated using standard reference nucleic acids, previously measured base composition and converted data to generate base compositions. For example, but not limitation, a standard reference nucleic acid can include commercially available vectors like pUC, the certified values for CODIS 13 loci (SRM 2391b available from the National Institute of Standards and Technology) and the Anderson mitochondrial DNA sequence. Converted data can include, but is not limited to, previously obtained sequence data, such as the reference data that is stored in the SWGDAM database that is bioinformatically converted to base composition data.

Also provided herein are compositions and methods for identifying a human by comparison of base compositions of amplification products representing overlapping sub-segments of a target nucleic acid with base compositions of reference sub-segments of one or more reference nucleic acids.

Amplification products of portions of the target nucleic acid which correspond to the sub-segments are produced and their molecular masses are measured by mass spectrometry. Base compositions of the amplification products are calculated from their molecular masses and the base compositions are compared with the base compositions of the corresponding sub-segments of the reference nucleic acid. A given target region can have any length depending upon the type of analysis to be conducted and in recognition of the numbers of primer pairs required to obtain amplification products representing overlapping sub-segments of the target, If a bacterium with a large genome is to be analyzed, and the target is the entire genome, a target nucleic acid may have a length of several kilobases. Alternatively, a target region may be of a length of about 300 to about 1000 nucleobases in length.

In some embodiments, the nucleic acid variant has a sequence identical to the standard sequence with the exception of having one or more single nucleotide polymorphisms, insertions or deletions.

In some embodiments, the reference nucleic acid and variant nucleic acid is either single stranded or double stranded DNA or RNA. In some embodiments, the standard and variant nucleic acid originates from the genome of a bacterium or a virus or is a synthesized nucleic acid such as a PCR product, for example.

A set of sub-segments within the reference nucleic acid sequence is defined. In some embodiments, the members of the set of standard sub-segments are from about 45 to about 150 nucleobases in length. One will recognize that this includes standard sub-segments of lengths of 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, or 150 nucleobases in length.

In some embodiments, the molecular masses of the test amplification products are determined by mass spectrometry such as electrospray Fourier transform ion cyclotron resonance (FTICR) mass spectrometry or electrospray time-of-flight mass spectrometry. The use of electrospray mass spectrometry permits the measurement of large amplification products, as large as 500 nucleobases in length, whereas amplification products analyzed by matrix-assisted laser desorption ionization mass spectrometry are typically much smaller in length (approximately 15 nucleobases in length).

Figure 2:
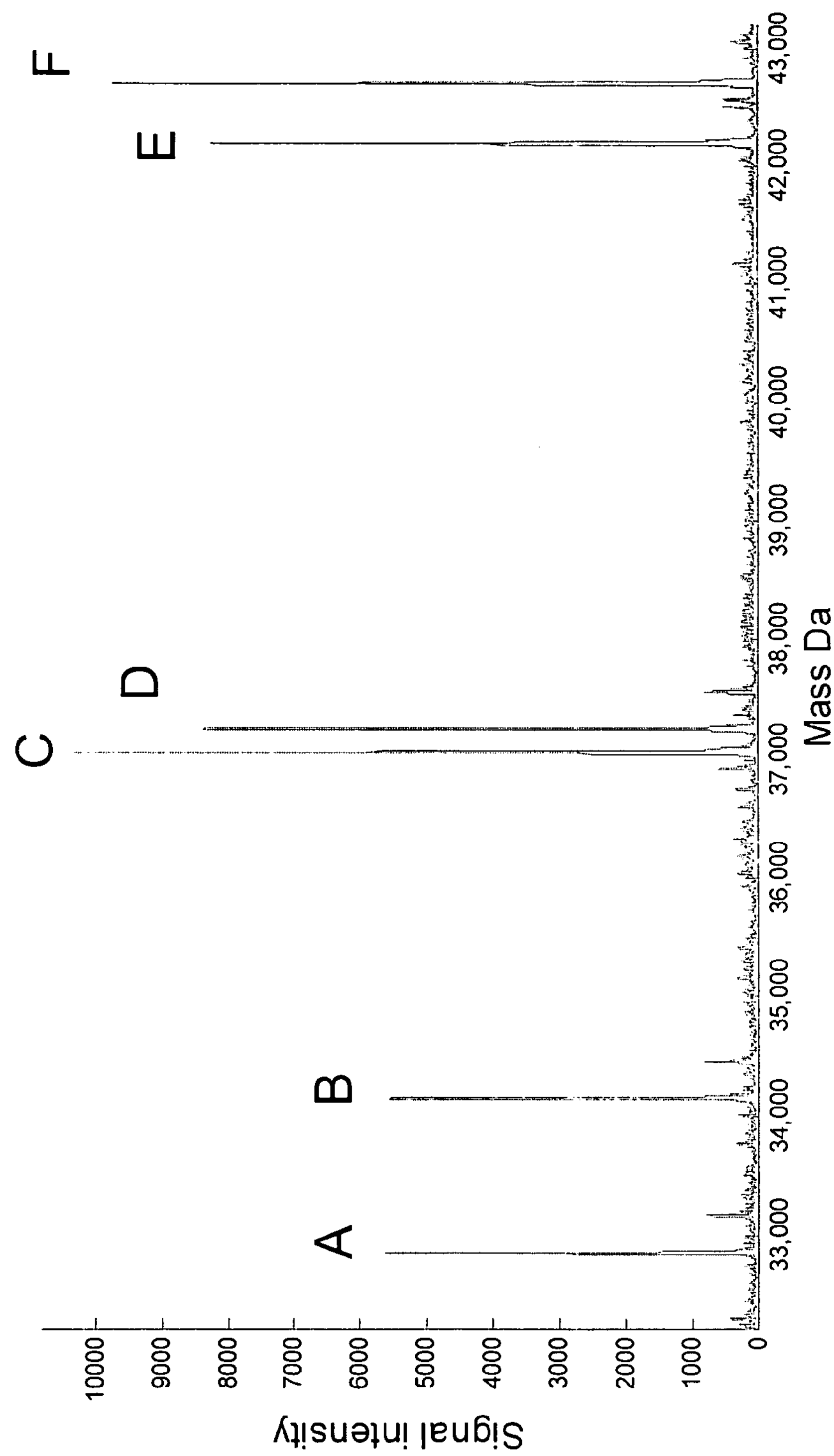
FIG. 2 is mass spectrum of three amplification products of a sample of mitochondrial DNA displaying six peaks corresponding to the individual strands of each of the three amplification products, each corresponding to sub-segments of the target mitochondrial DNA. Peaks labeled A and B are from a single amplification product of the HV1 region obtained with primer pair number 2892 (SEQ ID NOs: 4:29). Peaks labeled C and D are from a single amplification product of the HV1 region obtained with primer pair number 2901 (SEQ ID NOs: 12:37). Peaks labeled E and F are from a single amplification product of the HV2 region obtained with primer pair number 2906 (SEQ ID NOs: 17:42).
Figure 3:
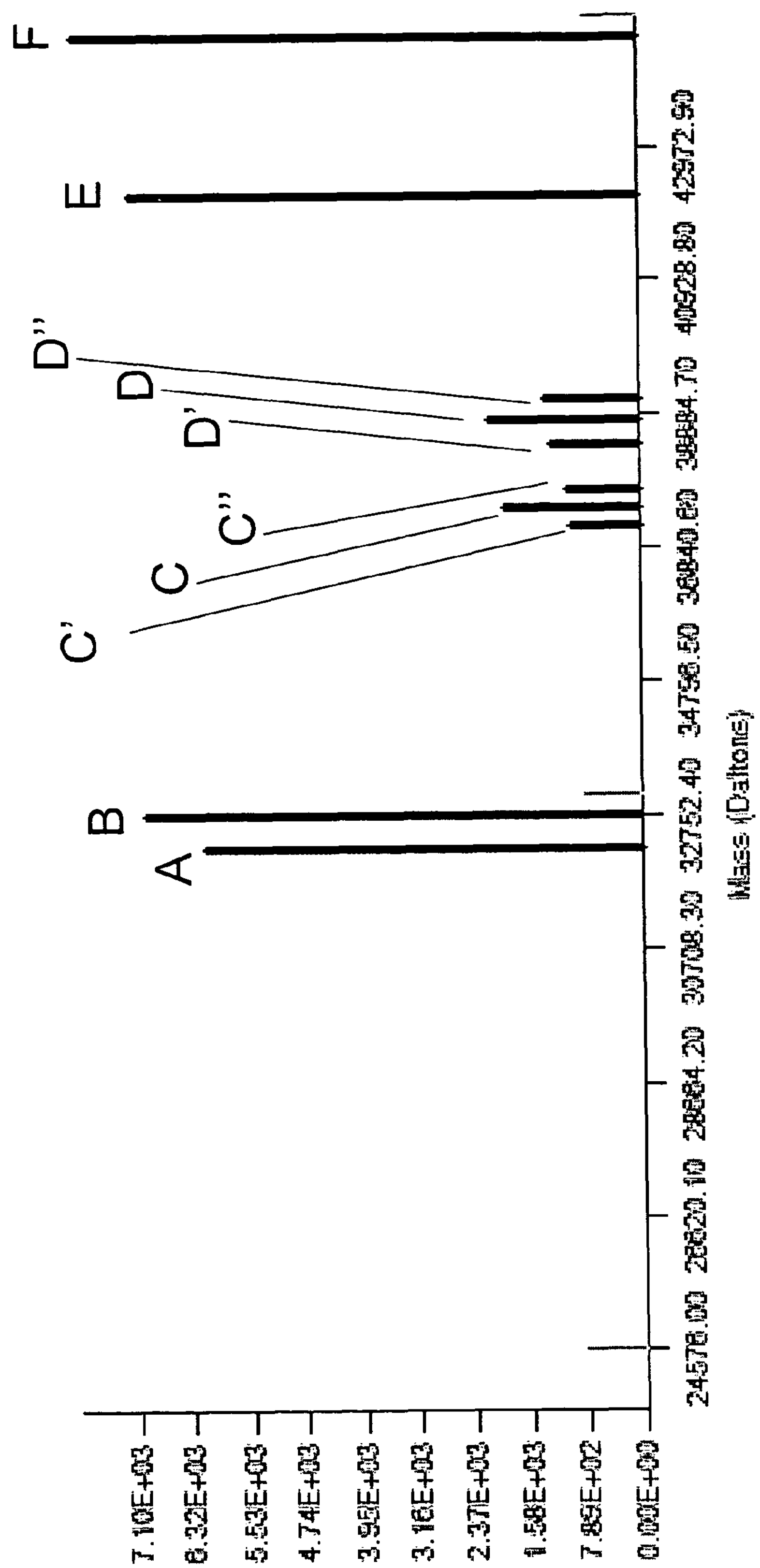
FIG. 3 represents a refinement of peaks from a mass spectrum of a sample mitochondrial DNA displaying six peak lines corresponding to the individual strands of each of the three amplification products. Detection of heteroplasmy in one of the amplified regions is indicated. Peaks labeled A and B are from a single amplification product of the HV1 region obtained with primer pair number 2904 (SEQ ID NOs: 15:40). Peaks labeled C and D are from a single amplification product of the HV1 region obtained with primer pair number 2896 (SEQ ID NO: 8:33). Peaks labeled C' and D' are from a single amplification product of the HV1 region obtained with primer pair number 2896 which represents one heteroplasmic variant of the amplification product represented by peaks C and D. Peaks labeled C" and D" are from a single amplification product of the HV1 region obtained with primer pair number 2896 which represents another heteroplasmic variant of the amplification product represented by peaks C and D. Peaks labeled E and F are from a single amplification product of the HV2 region obtained with primer pair number 2913 (SEQ ID NO: 22:47).

If desired, the length of the standard segments can be chosen such that some members of the set have calculated molecular masses that are dissimilar from other members of the set. Having standard segments of dissimilar molecular masses allows for multiplexing or pooling of amplification products corresponding to the standard segments prior to molecular mass determination, by mass spectrometry for example. As is illustrated in FIGS. 2 and 3, the resultant amplification products from a reaction using the at least two primer pairs are sufficiently separated along the charge axis of the mass spectrometry plot. This separation is preferred, but not necessary, because the individually measured amplicon strands can be easily visualized.

In some embodiments, the compositions and methods are used for genotyping of a suspected variant of a known species of bacterium or virus. The base compositions of the test amplification products, if different from the base composition of the standard segments, provide the means for identification of a previously known variant, or for characterization of a previously unobserved variant.

In some embodiments, the compositions and methods are used for identification and characterization of genetically engineered bacteria or viruses. Genetically engineered organisms are produced by insertion or deletion of genes. These modifications are readily detectable by the methods of the present invention.

In some embodiments, the compositions and methods can be used for validation of reference nucleic acid sequences such as those encoding therapeutic proteins including but not limited to vaccines and biological drugs such as monoclonal antibodies for example. A nucleic acid is "validated" by base composition analysis according to the method of the present invention, wherein the result indicates that the analyzed nucleic acid and/or sub-segments thereof have the same base compositions as the reference nucleic acid. The process of "validation" confirms that polymorphisms have not been introduced into the target sequence relative to the reference sequence.

In some embodiments, a known quantity of the standard sequence is included in the sample (as an internal calibration standard) containing the suspected variant and the quantity of the variant is determined from the abundance data obtained from mass spectrometry for example. Methods of using internal calibration standards in base composition analyses are described in commonly owned U.S. application Ser. No. 11/059,776 which is incorporated herein by reference in entirety.

In some embodiments, the compositions and methods are used for characterization of heterogeneity of a standard nucleic acid test sample. For example, the standard nucleic acid test sample can be a vaccine vector having a standard sequence. The present invention can be used to identify a variant of said standard sequence and also determine the quantity of the variant relative to the standard sequence. Such an analysis is advantageous, for example, in situations requiring rapid throughput analysis for quality control. The methods described herein will be able to determine if the quantity of a variant sub-population increases to the point wherein quality of the product is compromised.

In some embodiments, the compositions and methods are used for identification of a genotype of a given organism. This can be accomplished by first, selecting a series of primer pairs for amplification of consecutive or overlapping segments of a standard nucleic acid region found across known genotypes of a given organism. The process continues by amplifying a test nucleic acid of an organism of unknown genotype with the series of primer pairs to obtain a corresponding series of amplification products, at least some of which are then measured by mass spectrometry. Base compositions of the amplification products are then calculated from the molecular masses. These base compositions are compared with measured or calculated amplification product base compositions representing amplification products of known genotypes of a given organism obtained with the same series of primers. One or more matches of known and unknown base compositions provide the genotype of the organism.

Preferably, at least some or all of the amplification products have a range of lengths between about 45 to about 150 nucleobases. However, and depending on the mass spectrometer instrument used, the amplification products analyzed by mass spectrometry can be as large as about 500 nucleobases. Moreover, very large amplification products can be digested into smaller fragments that are compatible with the mass spectrometer used. Methods of base composition analysis are described in commonly owned U.S. patent application Ser. Nos. 10/660,998, 10/853,660, and 11/209,439, each of which are incorporated herein by reference in entirety.

In some embodiments, the amplification is effected using the polymerase chain reaction (PCR). In some embodiments, the PCR reaction is performed with an extension cycle having a length of one second. The one second extension cycle is shorter than an ordinary extension cycle and is employed for the purpose of minimization of artifact amplification products arising from target site crossover.

In some embodiments, the organism of unknown genotype is a human individual. In some embodiments, obtaining a genotypic result for a human individual provides the means to draw a forensic conclusion with regard to the individual, for example, to conclude with a very high probability that the individual has had contact with another individual or was present at a particular location.

In some embodiments with applications in human forensics, a given forensic nucleic acid sample may be characterized by base composition analysis that includes comparison with members of a database of tens, hundreds or even thousands of reference nucleic acid segments obtained from individuals of known identity or racial profile, or with standard references like the Anderson mitochondrial DNA sequence. Such a database can be stored on or embedded in a computer-readable medium and accessed over a network such as the internet for example. Preferably the database comprises base compositions of individual sub-segments of the reference nucleic acids.

In some embodiments, the nucleic acid being amplified for a genotyping analysis is mitochondrial DNA. In other embodiments, the nucleic acid is chromosomal DNA.

In some embodiments, the mitochondrial DNA being amplified for a genotyping analysis is from one or both of the highly variable regions HV1 or HV2.

In some embodiments, the length of the DNA region being analyzed is 300 to 700 nucleobases in length. In other embodiments, the length of the DNA region being analyzed in 400 to 600 nucleobases in length or any length therewithin.

In some embodiments, the amplifying step of the method is carried out in the presence of a dNTP containing a molecular mass-modifying tag. In some embodiments, only one of the four canonical dNTPs has the molecular mass-modifying tag. In some embodiments, the dNTP containing the molecular mass-modifying tag is 2'-deoxy-guanosine-5'-triphosphase, which has the greatest mass of the four canonical dNTPs. In other embodiments, any of the other three canonical dNTPs can contain the molecular mass-modifying tag. In some embodiments, the tag comprises a minor isotope of carbon or nitrogen. In some embodiments, the isotope of the molecular mass-modifying tag is $^{13}C$ or $^{15}N$. The advantage to employing the latter mass-modifying tags is that the dNTP structure is not altered and thus, efficiency of the amplification process should be retained.

In some embodiments, the 3' end residue of each primer hybridizes to a conserved nucleic acid residue of the target nucleic acid wherein the conserved nucleic acid residue is conserved among different genotypes. In other embodiments, the final two 3' end residues of each primer hybridizes to a conserved nucleic acid residue of the target nucleic acid wherein the conserved nucleic acid residue is conserved among different genotypes. In other embodiments, the final three 3' end residues of each primer hybridizes to a conserved nucleic acid residue of the target nucleic acid wherein the conserved nucleic acid residue is conserved among different genotypes.

In some embodiments, multiplexing amplification reactions are carried out with at least two primer pairs. In other embodiments, multiplexing reactions are carried out with three primer pairs, also known as triplex combinations.

In some embodiments, the compositions and methods are used for characterization of length or base composition heteroplasmy in mitochondrial DNA and also for determination of the quantity of a given heteroplasmic variant relative to a "standard" mitochondrial DNA region. In some embodiments, characterization of length heteroplasmy is used to diagnose and/or evaluate the progression of a mitochondrial DNA-related genetic disease such as one or more of the following mitochondrial diseases: Alpers Disease, Barth syndrome, Beta-oxidation Defects, Carnitine-Acyl-Carnitine Deficiency, Carnitine Deficiency, Co-Enzyme QIO Deficiency, Complex I Deficiency, Complex II Deficiency, Complex III Deficiency, Complex IV Deficiency, Complex V Deficiency, COX Deficiency, CPEO, CPT I Deficiency, CPT II Deficiency, Glutaric Aciduria Type II, KSS, Lactic Acidosis, LCAD, LCHAD, Leigh Disease or Syndrome, LHON, Lethal Infantile Cardiomyopathy, Luft Disease, MAD, MCA, MELAS, MERRF, Mitochondrial Cytopathy, Mitochondrial DNA Depletion, Mitochondrial Encephalopathy, Mitochondrial Myopathy, MNGIE, NARP, Pearson Syndrome, Pyruvate Carboxylase Deficiency, Pyruvate Dehydrogenase Deficiency, Respiratory Chain, SCAD, SCHAD, or VLCAD.

Determination of sequence identity is described in the following example: a nucleic acid 20 nucleobases in length which is otherwise identical to another 20 nucleobase nucleic acid but having two non-identical residues has 18 of 20 identical residues has 18/20=0.9 or 90% sequence identity. In another example, a nucleic acid 15 nucleobases in length having all residues identical to a 15 nucleobase segment of a nucleic acid 20 nucleobases in length would have 15/20=0.75 or 75% sequence identity with the 20 nucleobase nucleic acid. In another example, a nucleic acid 17 nucleobases in length having all residues identical to a 15 nucleobase segment of a nucleic acid 20 nucleobases in length would have 15/17=0.882 or 88.2% sequence identity. In some embodiments, a nucleic acid variant has between about 70% and 99% sequence identity with a standard nucleic acid sequence. In other embodiments, the nucleic acid variant has between about 75% to about 99% sequence identity. In other embodiments, the nucleic acid has between about 80% to about 99% sequence identity. In other embodiments, the nucleic acid has between about 85% to about 99% sequence identity. In other embodiments, the nucleic acid has between about 90% to about 99% sequence identity. In other embodiments, the nucleic acid has between about 95% to about 99% sequence identity. One will recognize that these embodiments provide for nucleic acid variants having sequence identity with a standard nucleic acid sequence ranging from about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, or 98%, to about 99%, as well as fractions thereof.

EXAMPLES

Example 1

Selection of Primers for Analysis of Mitochondrial DNA

An alignment of 5615 mitochondrial DNA sequences was constructed and analyzed for regions of conservation which are useful as primer binding sites for tiling coverage of the mitochondrial DNA regions HV1 and HV2. A total of 24 primer binding sites were chosen according to the criterion that the 5'-end of the primer binding sites remain conserved across the alignment of mitochondrial DNA sequences. In some cases, only the 5'-terminal nucleobase itself is conserved. In other cases, as many as two or three consecutive nucleobases at the 5' end of the primer binding sites are conserved.

In cases where primer coverage at a particular region is desired but complete conservation is absent, backup primer pairs can be chosen to ensure that target sequences will be amplified. For example, the 5' end of the primer binding site for the forward primer of primer pair number 2893 is 99.7% conserved among the 5615 mitochondrial DNA sequences of the alignment, a backup primer pair was designed. Primer pair number 2894 has a G residue instead of an A residue because A is 0.3% conserved at the 5' end of the primer binding site.

Table 1 shows the panel of 25 primer pairs designed to tile the informative HV1 (coordinates 15924 . . . 16428) and HV2 (coordinates 31-576) mitochondrial DNA regions for complete and partially redundant coverage with partially overlapping amplification products according to the general scheme shown in FIG. 1. The extent of overlap may vary but generally overlapping regions relative to two amplification products should range from about ten nucleobases to about 50 nucleobases of overlap. The sizes of amplification products produced with the primer pairs of Table 1 range in length from 85 to 140 nucleobase pairs. With the exception of three amplification products, all are less than 130 nucleobase pairs. The coordinates of the primer binding sites are given in the forward and reverse primer names with reference to the standard Anderson mitochondrial DNA sequence (SEQ ID NO: 51). For example, the forward primer of primer pair number 2889 (SEQ ID NO: 1) hybridizes to coordinates 16357-16376 of the standard Anderson mitochondrial DNA sequence (SEQ ID NO: 51). The primer pair name designation "HUMMTDNA" refers to human mitochondrial DNA. Primer pair numbers 2901 and 2925 are designed to produce an amplification product corresponding to the same sub-segment defined by Anderson mitochondrial DNA coordinates 15924 . . . 15985 (see Table 2). This extent of redundancy is sometimes beneficial in cases where high variability occurs at chosen primer binding sites such that a given primer of a primer pair does not effectively hybridize to the mitochondrial DNA of certain individuals. For this reason, 25 primer pairs are used to obtain amplification products of 24 sub-segments.

TABLE 1

Primer Pairs Used for Amplifying HV1 and HV2 Regions of Mitochondrial DNA

| Primer pair number | Forward primer name | Forward sequence | Forward SEQ ID NO: | Reverse primer name | Reverse sequence | Reverse SEQ ID NO: |
|---|---|---|---|---|---|---|
| 2889 | HUMMTDNA_ASN_16357_16376_F | TCTCGTCCCCATGGATGACC | 1 | HUMMTDNA_ASN_16429_16451_R | TCGAGGAGAGTAGCACTCTTGTG | 26 |
| 2890 | HUMMTDNA_ASN_16318_16341_F | TGCCATTTACCGTACATAGCACAT | 2 | HUMMTDNA_ASN_16382_16402_R | TGGTCAAGGGACCCCTATCTG | 27 |

TABLE 1-continued

Primer Pairs Used for Amplifying HV1 and HV2 Regions of Mitochondrial DNA

| Primer pair number | Forward primer name | Forward sequence | Forward SEQ ID NO: | Reverse primer name | Reverse sequence | Reverse SEQ ID NO: |
|---|---|---|---|---|---|---|
| 2891 | HUMMTDNA_ASN_16256_16282_F | TCACCCCTCACCCACTAGGATACCAAC | 3 | HUMMTDNA_ASN_16345_16366_R | TGGGACGAGAAGGGATTTGACT | 28 |
| 2892 | HUMMTDNA_ASN_16231_16253_F | TCACACATCAACTGCAACTCCAA | 4 | HUMMTDNA_ASN_16306_16338_R | TGCTATGTACGGTAAATGGCTTTATGTACTATG | 29 |
| 2893 | HUMMTDNA_ASN_16154_16181_F | TAGTACATAAAAACCCAATCCACATCAA | 5 | HUMMTDNA_ASN_16251_16268_R | TGGTGAGGGGTGGCTTTG | 30 |
| 2894 | HUMMTDNA_ASN_16154_16181_2_F | TAGTACATAAAAACCCAATCCACATCAG | 6 | HUMMTDNA_ASN_16251_16268_R | TGGTGAGGGGTGGCTTTG | 31 |
| 2895 | HUMMTDNA_ASN_16130_16156_F | TTTCCATAAATACTTGACCACCTGTAG | 7 | HUMMTDNA_ASN_16202_16224_R | TGGGTTGATTGCTGTACTTGCTT | 32 |
| 2896 | HUMMTDNA_ASN_16102_16123_F | TACTGCCAGCCACCATGAATAT | 8 | HUMMTDNA_ASN_16202_16224_R | TGGGTTGATTGCTGTACTTGCTT | 33 |
| 2897 | HUMMTDNA_ASN_16055_16077_F | TCCAAGTATTGACTCACCCATCA | 9 | HUMMTDNA_ASN_16130_16155_R | TACAGGTGGTCAAGTATTTATGGTAC | 34 |
| 2898 | HUMMTDNA_ASN_16025_16047_F | TCTTTCATGGGGAAGCAGATTTG | 10 | HUMMTDNA_ASN_16099_16119_R | TCATGGTGGCTGGCAGTAATG | 35 |
| 2899 | HUMMTDNA_ASN_15985_16014_F | TGCACCCAAAGCTAAGATTCTAATTTAAAC | 11 | HUMMTDNA_ASN_16052_16073_R | TGGTGAGTCAATACTTGGGTGG | 36 |
| 2901 | HUMMTDNA_ASN_15893_15923_F | TGGGGTATAAACTAATACACCAGTCTTGTAA | 12 | HUMMTDNA_ASN_15986_16012_R | TTAAATTAGAATCTTAGCTTTGGGTGC | 37 |
| 2902 | HUMMTDNA_ASN_5_30_F | TCAGGTCTATCACCCTATTAACCACT | 13 | HUMMTDNA_ASN_77_97_R | TGTCTCGCAATGCTATCGCGT | 38 |
| 2903 | HUMMTDNA_ASN_20_40_F | TATTAACCACTCACGGGAGCT | 14 | HUMMTDNA_ASN_115_139_R | TTTCAAAGACAGATACTGCGACATA | 39 |
| 2904 | HUMMTDNA_ASN_83_102_F | TAGCATTGCGAGACGCTGGA | 15 | HUMMTDNA_ASN_163_187_R | TGCCTGTAATATTGAACGTAGGTGC | 40 |
| 2905 | HUMMTDNA_ASN_113_137_F | TCTATGTCGCAGTATCTGTCTTTGA | 16 | HUMMTDNA_ASN_218_245_R | TGGGTTATTATTATGTCCTACAAGCATT | 41 |
| 2906 | HUMMTDNA_ASN_154_177_F | TCCTTTATCGCACCTACGTTCAAT | 17 | HUMMTDNA_ASN_268_290_R | TGGTTGTTATGATGTCTGTGTGG | 42 |
| 2907 | HUMMTDNA_ASN_239_262_F | TAACAATTGAATGTCTGCACAGCC | 18 | HUMMTDNA_ASN_341_363_R | TGTTTTTGGGGTTTGGCAGAGAT | 43 |
| 2908 | HUMMTDNA_ASM_204_233_F | TGTGTTAATTAATTAATGCTTGTAGGACAT | 19 | HUMMTDNA_ASN_314_330_R | TCTGTGGCCAGAAGCGG | 44 |
| 2910 | HUMMTDNA_ASN_331_354_F | TCTTAAACACATCTCTGCCAAACC | 20 | HUMMTDNA_ASN_402_425_R | TAAAAGTGCATACCGCCAAAAGAT | 45 |

TABLE 1-continued

Primer Pairs Used for Amplifying HV1 and HV2 Regions of Mitochondrial DNA

| Primer pair number | Forward primer name | Forward sequence | Forward SEQ ID NO: | Reverse primer name | Reverse sequence | Reverse SEQ ID NO: |
|---|---|---|---|---|---|---|
| 2912 | HUMMTDNA_ASN_409_430_F | TGCGGTATGCACTTTTAACAGT | 21 | HUMMTDNA_ASN_502_521_R | TGTGTGTGCTGGGTAGGATG | 46 |
| 2913 | HUMMTDNA_ASN_464_492_F | TCTCCCATACTACTAATCTCATCAATACA | 22 | HUMMTDNA_ASN_577_603_R | TGCTTTGAGGAGGTAAGCTACATAAAC | 47 |
| 2916 | HUMMTDNA_ASN_367_388_F | TACCCTAACACCAGCCTAACCA | 23 | HUMMTDNA_ASN_438_463_R | TGGAGGGGAAAATAATGTGTTAGTTG | 48 |
| 2923 | HUMMTDNA_ASN_262_288_F | TGCTTTCCACACAGACATCATAACAAA | 24 | HUMMTDNA_ASN_368_390_R | TCTGGTTAGGCTGGTGTTAGGGT | 49 |
| 2925 | HUMMTDNA_ASN_15937_15962_F | TCCTTTTTCCAAGGACAAATCAGAGA | 25 | HUMMTDNA_ASN_16018_16041_R | TGCTTCCCCATGAAAGAACAGAGA | 50 |

TABLE 2

Amplification Coordinates of Mitochondrial DNA for the Primer Pairs of Table 1

| Primer pair number | Amplification Coordinates | mtDNA Region |
|---|---|---|
| 2889 | 16377 . . . 16428 | HV1 |
| 2890 | 16342 . . . 16381 | HV1 |
| 2891 | 16283 . . . 16344 | HV1 |
| 2892 | 16254 . . . 16305 | HV1 |
| 2893 | 16182 . . . 16250 | HV1 |
| 2894 | 16182 . . . 16250 | HV1 |
| 2895 | 16157 . . . 16201 | HV1 |
| 2896 | 16124 . . . 16201 | HV1 |
| 2897 | 16078 . . . 16129 | HV1 |
| 2898 | 16048 . . . 16098 | HV1 |
| 2899 | 16015 . . . 16051 | HV1 |
| 2901 | 15924 . . . 15985 | HV1 |
| 2902 | 31 . . . 76 | HV2 |
| 2903 | 41 . . . 114 | HV2 |
| 2904 | 103 . . . 162 | HV2 |
| 2905 | 138 . . . 217 | HV2 |
| 2906 | 178 . . . 267 | HV2 |
| 2907 | 263 . . . 340 | HV2 |
| 2908 | 234 . . . 314 | HV2 |
| 2910 | 355 . . . 402 | HV2 |
| 2912 | 431 . . . 501 | HV2 |
| 2913 | 493 . . . 576 | HV2 |
| 2916 | 389 . . . 437 | HV2 |
| 2923 | 289 . . . 371 | HV2 |
| 2925 | 15924 . . . 15985 | HV1 |

Example 2

Validation of Triplex Tiling Mitochondrial DNA Assay

The 25 primer pairs of Table 1 were divided into triplex combinations of three primer pairs such that the amplification products of three primer pairs within a triplex combination have sense and antisense strands which are significantly different in molecular mass from the other sense and antisense strands of other amplification products within the triplex combinations. The triplex combinations are shown in Table 3 with reference to primer pair combinations.

TABLE 3

Triplex Combinations of Primer Pairs for Simultaneous Analysis of Mitochondrial DNA Regions

| Triplex Combination No. | Primer Pair Number | Primer Pair Number | Primer Pair Number |
|---|---|---|---|
| 1 | 2892 | 2901 | 2906 |
| 2 | 2891 | 2908 | 2925 |
| 3 | 2890 | 2899 | 2907 |
| 4 | 2898 | 2889 | 2923 |
| 5 | 2902 | 2910 | 2893/2894 |
| 6 | 2916 | 2897 | 2893 |
| 7 | 2904 | 2896 | 2913 |
| 8 | 2895 | 2912 | 2905 |

PCR cycle conditions used for obtaining amplification products for this assay are as follows: 10 minutes at 96° C. followed by six cycles of steps (a) to (c) wherein: (a) is 20 seconds at 96° C., (b) is 1.5 minutes at 55° C., and (c) is 1 second at 72° C., followed by 36 cycles of steps (d) to (f) wherein (d) is 20 seconds at 96° C., (b) is 1.5 minutes at 50° C., and (c) is 1 second at 72° C., followed by a retention at 4° C. All PCR reactions were carried out with an Eppendorf thermal cycler with 40 μl reaction volumes in a 96-well microtiter plate format. Liquid manipulations were performed using a Packard MPII liquid handling robotic platform. The PCR reaction mixture consisted of 4 units of Amplitaq Gold, 1× buffer II (Applied Biosystems, Foster City, Calif.), 1.5 mM $MgCl_2$, 800 μM dNTP mixture and 250 nM of each primer. The dNTP mixture contained carbon-13 enriched deoxyguanosine triphosphate, a chemically invisible molecular mass-modifying tag which adds 10 Da to each G residue incorporated into a given amplification product so that the numbers of possible base compositions consistent with a measured molecular mass is reduced and the probability of assignment of an incorrect base composition to a given amplification product is greatly decreased.

Eleven saliva samples were obtained from in-house laboratory personnel and subjected to PCR reactions as described above with the 8 triplex primer pair sets shown in Table 3. The PCR amplification products were purified according to the primary amine-terminated magnetic bead separation method; a technique that is well known in the art and that is described in US patent publication 20050130196 which is incorporated herein by reference in entirety. All amplification products were analyzed using a Bruker Daltonics MicroTOF™ mass spectrometer. Ions from the ESI source undergo orthogonal ion extraction and are focused in a reflectron prior to detection. The TOF and FTICR are equipped with the same automated sample handling and fluidics described above. Ions are formed in the standard MicroTOF™ ESI source that is equipped with the same off-axis sprayer and glass capillary as the FTICR ESI source. Consequently, source conditions were the same as those described above. External ion accumulation was also employed to improve ionization duty cycle during data acquisition. Each detection event on the TOF was comprised of 75,000 data points digitized over 75 μs.

Mass spectra of the amplification products were analyzed independently using a maximum-likelihood processor, such as is widely used in radar signal processing. This processor, referred to as GenX, first makes maximum likelihood estimates of the input to the mass spectrometer for each primer by running matched filters for each base composition aggregate on the input data. This processor is described in U.S. Patent Application Publication No. 20040209260 which is incorporated herein by reference in entirety.

All duplicate reactions were analyzed independently and duplicate results were identical in all cases. An example of a mass spectrum of triplex primer combination 1 (primer pair nos. 2892, 2901 and 2906) is shown in FIG. 2 wherein each of the peaks labeled A-F represent a single strand of DNA of an amplification product. The strands are clearly separated which facilitates efficient analysis of the molecular masses.

The applicability of the present invention for resolution of mitochondrial DNA heteroplasmy is indicated in FIG. 3. Strands C', D', C" and D" represent two amplification products having length heteroplasmy of the amplification product of strands C and D. Each of the strands of the heteroplasmic variants is visible in the mass spectrum because they vary in molecular mass.

Example 3

Rapid Typing of Human Mitochondrial DNA

Mitochondrial DNA (mtDNA) analysis of forensic samples is performed when the quantity and/or quality of DNA are insufficient for nuclear DNA analysis, or when DNA analysis through a maternal lineage is otherwise desired. Forensic mtDNA analysis is performed by sequencing portions of the mtDNA genome, which is a lengthy and labor intensive technique. We present a mass spectrometry-based multiplexed PCR assay suitable for automated analysis of mtDNA control region segments. The assay has been internally validated with 20 DNA samples with known sequence profiles and 50 blinded samples contributed by external collaborators. Correct profiles were obtained in all cases when compared to sequencing data. Two samples containing mixed templates were observed and the relative contribution of each template was quantified directly from the mass spectra of PCR products.

The primer pairs of Table 1 were designed to amplify 1051 bases of human mitochondrial DNA in the hypervariable regions HV1 and HV2. The primer pairs were combined in multiplex reactions in groups which were chosen such that the target segments of the three primer pairs being combined were maximally separated and such that each of the three amplification product masses in a triplex mixture were resolvable from each other by mass spectrometry. The triplex groups are shown in Table 3. The lengths of the amplification products were 85 to 140 base pairs. All except for three amplification products were less than 130 base pairs in length. The relative primer pair concentrations in the triplex mixtures were adjusted in order to favor simultaneous amplification of all three target segments.

Mass spectra were measured by electrospray time-of-flight (TOF) mass spectrometry.

A standard reference human mitochondrial DNA database was used to obtain the base composition profiles corresponding to the series of amplification products produced by the overlapping primer pairs. As described above, the database was populated with base composition data from the Anderson reference mitochondrial DNA, from base composition measurements earlier obtained, and by conversions from databases of earlier obtained sequencing data. These base composition profiles represent the "truth data."

Fifty blinded test samples, including 25 blood samples and 25 cheek swab samples were tested and compared to the pre-existing truth data. Mitochondrial DNA was purified from the samples by the Qiagen blood punch protocol or by the Qiagen buccal swab protocol and quantified using the Quantifiler qPCR kit prior to analysis. Two or more independent assays were performed with the overlapping primers of Table 1 using between 100 and 500 pg of mitochondrial DNA in each reaction.

The purified mitochondrial DNA was subjected to triplex PCR amplification with the eight triplex primer groups of Table 3 according to the procedure indicated in Example 2. Amplified mixtures were purified by solution capture of nucleic acids with ion exchange resin linked to magnetic beads as follows: 25 μl of a 2.5 mg/mL suspension of BioClone amine terminated superparamagnetic beads were added to 25 to 50 μl of a PCR (or RT-PCR) reaction containing approximately 10 pM of a typical PCR amplification product. The above suspension was mixed for approximately 5 minutes by vortexing or pipetting, after which the liquid was removed after using a magnetic separator. The beads containing bound PCR amplification product were then washed three times with 50 mM ammonium bicarbonate/50% MeOH or 100 mM ammonium bicarbonate/50% MeOH, followed by three more washes with 50% MeOH. The bound PCR amplicon was eluted with a solution of 25 mM piperidine, 25 mM imidazole, 35% MeOH which included peptide calibration standards.

Each mass spectrum obtained by ESI-TOF mass spectrometry was independently calibrated by internal peptide calibrants and noise-reduced prior to calculation of base composition. Base compositions were obtained from molecular masses and compared to a database developed from over 110,000 mitochondrial DNA sequences. The base composition of each amplification product was associated with mitochondrial DNA coordinates as shown, for example in Table 4 which provides the base compositions for sample AF-12 from the set of 50 blinded samples.

TABLE 4

Mitochondrial DNA Base Composition Profile for Sample AF-12

| Anderson/Cambridge Sequence Coordinates (SEQ ID NO: 51) | Base Composition |
|---|---|
| 15893 . . . 16012 | A47 G18 C25 T30 |
| 15937 . . . 16041 | A35 G14 C24 T32 |
| 15985 . . . 16073 | A26 G15 C21 T27 |

TABLE 4-continued

Mitochondrial DNA Base Composition Profile for Sample AF-12

| Anderson/Cambridge Sequence Coordinates (SEQ ID NO: 51) | Base Composition |
|---|---|
| 16025 . . . 16119 | A26 G17 C26 T26 |
| 16055 . . . 16155 | A31 G13 C30 T27 |
| 16102 . . . 16224 | A45 G13 C42 T23 |
| 16130 . . . 16224 | A36 G7 C33 T19 |
| 16154 . . . 16268 | A44 G7 C46 T18 |
| 16231 . . . 16338 | A40 G9 C40 T19 |
| 16256 . . . 16366 | A37 G9 C41 T24 |
| 16318 . . . 16402 | A20 G14 C30 T21 |
| 16357 . . . 16451 | A21 G17 C36 T21 |
| 5 . . . 97 | A19 G24 C24 T26 |
| 20 . . . 139 | A24 G34 C29 T33 |
| 83 . . . 187 | A23 G21 C29 T32 |
| 113 . . . 245 | A39 G18 C28 T48 |
| 154 . . . 290 | A49 G17 C31 T40 |
| 204 . . . 330 | A42 G16 C35 T32 |
| 204 . . . 330 | A42 G16 C36 T32 |
| 204 . . . 330 | A42 G16 C37 T32 |
| 239 . . . 363 | A43 G11 C46 T23 |
| 239 . . . 363 | A43 G11 C47 T23 |
| 239 . . . 363 | A43 G11 C48 T23 |
| 239 . . . 363 | A43 G11 C49 T23 |
| 262 . . . 390 | A47 G10 C50 T20 |
| 262 . . . 390 | A47 G10 C51 T20 |
| 262 . . . 390 | A47 G10 C52 T20 |
| 262 . . . 390 | A47 G10 C53 T20 |
| 331 . . . 425 | A33 G9 C27 T26 |
| 367 . . . 463 | A27 G8 C32 T30 |
| 409 . . . 521 | A32 G7 C48 T26 |
| 464 . . . 603 | A44 G10 C63 T23 |

Heteroplasmy was detected in several of the samples. For example, sample AF-4 has C⇆T heteroplasmy at position 16176. Two distinct amplification products having base compositions of A45 G13 C41 T24 and A45 G13 C40 T25 were obtained for this sample using primer pair number 2896 which amplifies positions 16102 . . . 16224. If conventional sequencing analyses were used to analyze the amplification reaction mixture, heteroplasmy would not have been detected. Table 5 indicates additional examples of heteroplasmy detected in various samples.

TABLE 5

Summary of Heteroplasmy Detection in Selected Samples

| Blinded Sample | Region | Heteroplasmy | Approximate % of Minor Product |
|---|---|---|---|
| AF-2 | 16231 . . . 16338<br>16256 . . . 16366 | C → T | 32.4 |
| AF-4 | 16102 . . . 16224<br>16130 . . . 16224 | C → T | 49.2 |
| AF-7 | 16318 . . . 16402 | T → C | 10.2 |
| AF-9 | 464 . . . 603 | AC insertion | 17.3 |
| AF-19 | 15985 . . . 16073<br>16025 . . . 16119 | A → G | 44.9 |
| AF-22 | 6102 . . . 16224<br>16130 . . . 16224 | C → A | 36.2 |
| AF-24 | 464 . . . 603 | AC deletion | 13.5 |
| FBI-22 | 16055 . . . 16155 | A → C | 7.0 |
| FBI-37 | 16231 . . . 16338<br>16256 . . . 16366 | C → T | 20.0 |
| FBI-48 | 16055 . . . 16155 | T → G | 6.0 |
| FBI-49 | 154 . . . 290 | A → C | 10.6 |
| FBI-51 | 5 . . . 97<br>20 . . . 139 | C → T | 43.0 |
| FBI-57 | 16357 . . . 16451 | T → C | 6.0 |
| FBI-61 | 464 . . . 603 | AC insertion | 17.0 |
| FBI-66 | 113 . . . 245<br>154 . . . 290 | C → T | 50.0 |
| FBI-72 | 113 . . . 245<br>154 . . . 290 | C → T | 34.0 |

The results of the investigation of the 50 blinded samples indicated that 47 of 47 pure samples were directly concordant with the sequence data available. One negative (no mitochondrial DNA present) was confirmed as negative and two buccal swab samples were confirmed as mixtures of existing buccal swab samples. Deduction of contributors to mixtures was confirmed as accurate. Multiple examples of length heteroplasmy and single nucleotide polymorphism heteroplasmy were observed. These results indicate that the method is useful for rapid typing of human mitochondrial DNA.

Example 4

Demonstration of the Feasibility of Rapid Detection of a Genetic Engineering Event To detect a genetic engineering event indicated by the presence of foreign DNA sequences inserted into a parent virus, a strategy of overlapping PCR primers to tile large sections of viral genomes is employed. Primer binding sites were chosen such that the PCR amplicon length (standard segments) will be approximately 150 nucleobases in length with overlapping segments defined by primer hybridization regions every 50-100 nucleobases across the entire target region (in a manner exemplified by FIG. 1).

Target regions are chosen according to expectation of identification of a genetic engineering event at a particular region. For example, if it is known that "region X" of a genome of a given virus is known to be a common insertion point for a gene encoding a toxin used as a biowarfare agent, it would be advantageous to simplify the base composition analysis by choosing only the genomic coordinates of region X as the target (a portion of the genome chosen as the target). The target region is then divided into sub-segments and primer pairs are chosen to obtain amplification products which represent the sub-segments for base composition analysis. On the other hand, if it is known that any point in an entire genome is appropriate for insertion of a gene, it would be advantageous to define the entire genome as the target in order to ensure that the insertion is detected. One with ordinary skill will recognize that defining an entire genome as a target will require design of many more primer pairs and significantly more analysis resources.

A database of molecular masses and base compositions for each standard segment for the standard target virus species will be used to assemble a base composition map of each sampled region from the mass spectrum derived from each amplification reaction. The identification of at least one amplification product whose base composition differs from the base composition of its corresponding standard segment in one or more overlapping tiled regions will indicate that a variant exists and the sample will be flagged for further analysis. SNP variants are readily recognized and can be directly analyzed by the methods described herein. As an example of the proposed method, 10 Kb nucleobase regions of orthopoxvirus species genetically engineered with a green-fluorescent protein (GFP) construct are inserted into analogous regions in five different orthopoxviruses which will serve as benign surrogates to represent a potentially deadly engineered virus.

In the following proof-of-concept example using the recombinant GFP-containing camelpoxvirus (CMPV-GFP), simulated processed mass spectrometry data was used to reconstruct a standard segment base composition map, associate it unambiguously to CMPV, and identify presence of a foreign insert in the virus by flagging an unexpected/unmatched hole in two of the amplified regions. Overlapping primer pairs were selected to span the CMPV-GFP sequence. A theoretical prediction of the expected standard amplification products using these primers was used to populate a database that serves as an expected mass set for all poxvirus species. Processed mass spectrometry data of the amplified regions of CMPV-GFP were simulated and matched against the database of 16 poxvirus sequences (which did not include the GFP-engineered sequence) to construct a base composition profile of each region. The base composition profile is generated using the full set of potential fragments from all database sequences, which helps increase profile coverage in the case of strain-to-strain SNP variations. If any SNP-generated fragments appear that do not occur in any database sequence, the base composition of the double-stranded fragment can be deduced directly from the masses. The final base composition profile for each region can then be compared to the compositions for all database sequences to confirm/refine the identity of the parent virus. The presence of an unmatched "hole" in the assembled profile that cannot be matched to the expected viral sequence indicates the potential presence of an engineered insert. This region may then be sequenced and compared to the full sequence database via BLAST. The ability to rapidly identify the presence of the insert, the location of the insertion, and the flanking regions of the viral genome where the unexpected genetic modification was done will serve as a powerful tool to flag potential bioengineering events. It further reduces the burden of sequencing to specific, targeted regions of the viral genome instead of the entire virus from every sample.

Example 5

Vector Validation and Characterization of Vector Heterogeneity

This example illustrates a scenario where the method of the present invention could be used to validate and/or characterize heterogeneity of standard nucleic acid sequences encoding biological products. The process of production of biological therapeutic proteins such as vaccines and monoclonal antibodies requires storage and manipulation of the nucleic acid sequences encoding the therapeutic proteins. Mutations may occasionally arise within a given nucleic acid sequence encoding the protein and compromise its therapeutic effect. It is desirable to have a method for rapid validation of such nucleic acid sequences and characterization of heterogeneity of the sequences, if present.

Vector X contains a nucleic acid sequence encoding vaccine Y which is used to vaccinate individuals against infection of virus Z. Vector X is used to transfect a suitable host for production of vaccine Y. Vaccine Y is suspected of being compromised by a mutation that has arisen in the nucleic acid sequence encoding vaccine Y and is being propagated via routine laboratory manipulations of vector X.

The method of the present invention is used to analyze the nucleic acid of vector X by base composition analysis of sub-segments of the vector which encode vaccine Y. The nucleic acid sequence encoding vaccine Y is 300 nucleobases in length. This sequence is divided into four sub-segments as follows: sub-segment 1 represents coordinates 1 . . . 100 of the nucleic acid sequence encoding vaccine Y; sub-segment 2 represents coordinates 61 . . . 160 of the nucleic acid sequence encoding vaccine Y; sub-segment 3 represents coordinates 141 . . . 240 of the nucleic acid sequence encoding vaccine Y; and sub-segment 4 represents coordinates 221 . . . 300 of the nucleic acid sequence encoding vaccine Y. The base compositions of each of the four sub-segments are known because the sequence of vaccine Y is known. Sub-segment 1 of the nucleic acid of vaccine Y has a base composition of $A_{25}T_{20}C_{30}G_{25}$; sub-segment 2 of the nucleic acid of vaccine Y has a base composition of $Al_5T_{20}C_{35}G_{30}$; sub-segment 3 of the nucleic acid of vaccine Y has a base composition of $A_{20}T_{25}C_{30}G_{25}$; and sub-segment 4 of the nucleic acid of vaccine Y has a base composition of $A_{25}T_{15}C_{15}G_{20}$. Primer pair 1 is used to obtain an amplification product of vector X wherein the amplification product corresponds to sub-segment 1. Primer pair 2 is used to obtain an amplification product of vector X wherein the amplification product corresponds to sub-segment 2. Primer pair 3 is used to obtain an amplification product of vector X wherein the amplification product corresponds to sub-segment 3. Primer pair 4 is used to obtain an amplification product of vector X wherein the amplification product corresponds to sub-segment 4. The amplification products corresponding to sub-segments 1-4 are analyzed by mass spectrometry to determine their molecular masses. The base compositions of one or more of the amplification products are calculated from the molecular masses and compared with the base compositions of the sub-segments of vaccine Y listed above.

In one example, production lot A-1 of vector X is analyzed according to the method described above. The results of the base composition calculations indicate that each of the experimentally determined base compositions of the amplification products match the base compositions of the four sub-segments. The conclusion of this exercise is that vector X and the nucleic acid encoding vaccine Y contained thereon, do not contain mutations and that the vaccine vector is validated, indicating that future vaccine production will not be affected.

In another example, production lot B-2 of vector X is analyzed according to the method described above. The results of the base composition calculations indicate that each of the experimentally determined base compositions of the amplification products match the base compositions of the four sub-segments. An additional amplification product is observed in the mass spectrum of the amplification reaction of primer pair 3. The additional amplification product which corresponds to sub-segment 3 has a base composition of $A_{20}T_{25}C_{31}G_{24}$. This indicates that the additional amplification product has a G→C substitution relative to the standard base composition of sub-segment 3. The conclusion of this exercise is that vector X and the nucleic acid encoding vaccine Y are heterogeneous and that production of vaccine Y from production lot B-2 of vector X may be compromised. The mass spectrum indicating signals from two amplification products corresponding to sub-segment 3 may also be used to estimate the relative amounts of the two amplification products, thereby further characterizing the extent of heterogeneity of the nucleic acid sequence encoding vaccine Y. If the relative quantity of nucleic acid containing the mutation is low, it may be decided that heterogeneity is negligible. On the other hand, if the relative quantity of nucleic acid containing the mutation is high, it may be decided that vector X lot B-2 is severely compromised and should be destroyed instead of being used to produce vaccine Y.

Various modifications of the invention, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, internet web sites, and the like) cited in the present application is incorporated herein by reference in its entirety. Those skilled in the art will appreciate that numerous changes and modifications may be made to the embodiments of the invention and that such changes and modifications may be made without departing from the spirit of the invention. It is therefore intended that the appended claims cover all such equivalent variations as fall within the true spirit and scope of the invention.

What is claimed is:

1. A method for analyzing a nucleic acid comprising the steps of:

(a) obtaining a sample comprising nucleic acid for base composition analysis;

(b) selecting at least two primer pairs that will generate overlapping amplification products of at least two sub-segments of the nucleic acid;

(c) amplifying at least two nucleic acid sequences of a region of the nucleic acid designated as a target for base composition analysis using the at least two primer pairs, thereby generating at least two overlapping amplification products;

(d) determining base compositions of the amplification products by;

(i) measuring molecular masses of one or more of the amplification products generated in step (c) using a mass spectrometer; and (ii) converting one or more of the measured molecular masses to base compositions;

(e) comparing one or more of the base compositions with reference base composition data for the nucleic acid sequence; and (f) identifying the presence of a particular nucleic acid sequence or variant thereof.

2. The method of claim 1 wherein the step of selecting at least two primer pairs is selecting at least one triplex combination of primer pairs.

3. The method of claim 1 wherein the amplification product is from about 40 nucleobases in length to about 150 nucleobases in length.

4. The method of claim 3 wherein the amplification product is from about 46 nucleobases in length to about 140 nucleobases in length.

5. The method of claim 1 wherein the amplification product is less than 130 nucleobases.

6. The method of claim 1 wherein the amplification product is from about 85 nucleobases in length to about 140 nucleobases in length.

7. The method of claim 1 wherein the sample comprising nucleic acid for base composition analysis is selected from the group consisting of a human chromosomal nucleic acid, a human mitochondrial nucleic acid, a bacterial nucleic acid, a viral nucleic acid, a fungal nucleic acid, a synthetic nucleic acid, a recombinant nucleic acid and a combination thereof.

8. The method of claim 1 wherein the comparing step identifies at least one variant whose base composition differs from the base composition of its corresponding reference sub-segment, thereby characterizing a genotype of a human, bacterium, virus or fungus.

9. The method of claim 1 wherein the identifying step identifies at least one amplification product whose base composition differs from the base composition of its corresponding reference sub-segment, thereby identifying a genetically-engineered bacterium, virus or fungus.

10. The method of claim 7 wherein the sample for base composition analysis is at least a portion of the hypervariable Region I segment of a mitochondrial DNA.

11. The method of claim 10 wherein the hypervariable Region I segment is nucleotide positions 15924 to 16451 of SEQ ID NO: 51.

12. The method of claim 10 wherein the sample for base composition analysis comprises a heteroplasmy variant.

13. The method of claim 7 wherein the sample for base composition analysis is at least a portion of the hypervariable Region II segment of a mitochondrial DNA.

14. The method of claim 13 wherein the hypervariable Region II segment is nucleotide positions 31 to 576 of SEQ ID NO: 51.

15. The method of claim 13 wherein the sample for base composition comprises a heteroplasmy variant.

16. The method of claim 1 wherein the amplifying step is carried out in the presence of a dNTP comprising a mass modifying tag.

17. The method of claim 16 wherein the dNTP is 2'-deoxyguanosine-5'-triphosphate.

18. The method of claim 16 wherein the dNTP is 13.sup.C.

19. The method of claim 7 wherein the sample for base composition analysis is human mitochondrial DNA and the obtained base compositions are compared with corresponding reference sub-segments of a reference sequence comprising the Anderson/Cambridge sequence (SEQ ID NO: 51).

20. The method of claim 7 wherein the comparing of the measured base composition to the reference sub-segments provides genotype information comprising human identification, SNP identification, VNTR identification, recombinant insert identification, heteroplasmy identification, genetic disease disposition and combinations thereof.

21. The method of claim 1 wherein the amplification step is quantitative and further comprises the step of adding to the sample a known quantity of a calibrant that will co-amplify with the sample for sequence identity analysis.

22. The method of claim 1 wherein the mass spectrometry is electrospray Fourier transform ion cyclotron resonance mass spectrometry or electrospray time-of-flight mass spectrometry.

23. The method of claim 1 wherein the target region for base composition analysis has a length falling in the range comprising an upper limit of about 700 nucleobases and comprising a lower limit of about 300 nucleobases.

24. The method of claim 23 wherein the range comprises an upper limit of about 600 nucleobases and comprises a lower limit of about 400 nucleobases.

25. The method of claim 1 wherein the nucleic acid is a vector.

26. The method of claim 25 wherein the vector comprises a gene encoding a therapeutic protein.

27. A method for identifying a human comprising the steps of:

(a) obtaining a sample comprising mitochondrial DNA of the human for base composition analysis;

(b) selecting at least two primer pairs that will generate overlapping amplification products representing sub-segments of the mitochondrial DNA;

(c) amplifying at least two nucleic acid sequences of a region of the mitochondrial DNA designated as a target for base composition analysis using the at least two primer pairs, thereby generating at least two overlapping amplification products;

(d) determining base compositions of the amplification products by;

(i) measuring molecular masses of one or more of the amplification products generated in step (c) using a mass spectrometer; and (ii) converting one or more of the measured molecular masses to base compositions;

(e) comparing one or more of the base compositions with reference base composition data for the nucleic acid sequence thereby identifying the human.

28. The method of claim 27 wherein the sample for base composition analysis is at least a portion of the hypervariable Region I segment of a mitochondrial DNA.

29. The method of claim 28 wherein the hypervariable Region I segment is nucleotide positions 15924 to 16451 of SEQ ID NO: 51.

30. The method of claim 27 wherein the sample for base composition analysis is at least a portion of the hypervariable Region II segment of a mitochondrial DNA.

31. The method of claim 30 wherein the hypervariable Region II segment is nucleotide positions 31 to 576 of SEQ ID NO: 51.

32. The method of claim 27 wherein the comparing comprises a head-to-head comparison between said one or more of the base compositions and the reference base composition data.

33. The method of claim 27 wherein the comparing comprises a comparison between said one or more of the base compositions with a standard reference database comprising the reference base composition data.

34. A method for characterizing heteroplasmy in mitochondrial DNA comprising the steps of:

(a) obtaining a sample comprising mitochondrial DNA for base composition analysis;

(b) selecting at least two primer pairs that will generate overlapping amplification products representing sub-segments of the mitochondrial DNA;

(c) amplifying at least two nucleic acid sequences of a region of the mitochondrial DNA designated as a target for base composition analysis using the at least two primer pairs, thereby generating at least two overlapping amplification products;

(d) determining base compositions of the amplification products by;

(i) measuring molecular masses of one or more of the amplification products generated in step (c) using a mass spectrometer; and (ii) converting one or more of the measured molecular masses to base compositions;

(e) comparing one or more of the base compositions with one or more base compositions of reference sub-segments of a reference sequence; and (f) identifying at least two distinct amplification products with distinct base compositions obtained by the same pair of primers, thereby characterizing the heteroplasmy.

* * * * *

SEQUENCE LISTING

```
<160> NUMBER OF SEQ ID NOS: 52

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1

tctcgtcccc atggatgacc                                                20


<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2

tgccatttac cgtacatagc acat                                           24


<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3

tcacccctca cccactagga taccaac                                        27


<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4

tcacacatca actgcaactc caa                                            23


<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5

tagtacataa aaacccaatc cacatcaa                                       28
```

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
tagtacataa aaacccaatc cacatcag 28

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
tttccataaa tacttgacca cctgtag 27

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
tactgccagc caccatgaat at 22

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
tccaagtatt gactcaccca tca 23

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
tctttcatgg ggaagcagat ttg 23

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
tgcacccaaa gctaagattc taatttaaac 30

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
tggggtataa actaatacac cagtcttgta a 31

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
tcaggtctat caccctatta accact 26

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
tattaaccac tcacgggagc t 21

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
tagcattgcg agacgctgga 20

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
tctatgtcgc agtatctgtc tttga 25

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
tcctttatcg cacctacgtt caat 24

<210> SEQ ID NO 18
<211> LENGTH: 24

<212> TYPE: DNA
<213> ORGANISM: Artificial Sequence
<220> FEATURE:
<223> OTHER INFORMATION: Description of Artificial Sequence: Synthetic
primer

<400> SEQUENCE: 18
taacaattga atgtctgcac agcc 24

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 19
tgtgttaatt aattaatgct tgtaggacat 30

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 20
tcttaaacac atctctgcca aacc 24

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 21
tgcggtatgc acttttaaca gt 22

<210> SEQ ID NO 22
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 22
tctcccatac tactaatctc atcaataca 29

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 23
taccctaaca ccagcctaac ca 22

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
tgctttccac acagacatca taacaaa 27

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 25 tccttttcc aaggacaaat cagaga 26

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
tcgaggagag tagcactctt gtg 23

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
tggtcaaggg acccctatct g 21

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
tgggacgaga agggatttga ct 22

<210> SEQ ID NO 29
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
tgctatgtac ggtaaatggc tttatgtact atg 33

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
tggtgagggg tggctttg 18

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
tggtgagggg tggctttg 18

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
tgggttgatt gctgtacttg ctt 23

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
tgggttgatt gctgtacttg ctt 23

<210> SEQ ID NO 34
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
tacaggtggt caagtattta tggtac 26

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
tcatggtggc tggcagtaat g 21

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
tggtgagtca atacttgggt gg 22

<210> SEQ ID NO 37
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
ttaaattaga atcttagctt tgggtgc 27

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
tgtctcgcaa tgctatcgcg t 21

<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
tttcaaagac agatactgcg acata 25

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 40
tgcctgtaat attgaacgta ggtgc 25

<210> SEQ ID NO 41
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 41
tgggttatta ttatgtccta caagcatt 28

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 42
tggttgttat gatgtctgtg tgg 23

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 43
tgtttttggg gtttggcaga gat 23

<210> SEQ ID NO 44
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 44
tctgtggcca gaagcgg 17

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 45
taaaagtgca taccgccaaa agat 24

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 46
tgtgtgtgct gggtaggatg 20

<210> SEQ ID NO 47
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
tgctttgagg aggtaagcta cataaac 27

<210> SEQ ID NO 48
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 48
tggaggggaa aataatgtgt tagttg 26

<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 49
tctggttagg ctggtgttag ggt 23

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
tgcttcccca tgaaagaaca gaga 24

<210> SEQ ID NO 51
<211> LENGTH: 16568
<212> TYPE: DNA
<213> ORGANISM: Homo sapiens

<400> SEQUENCE: 51
gatcacaggt ctatcaccct attaaccact cacgggagct ctccatgcat ttggtatttt 60
cgtctggggg gtatgcacgc gatagcattg cgagacgctg gagccggagc accctatgtc 120
gcagtatctg tctttgattc ctgcctcatc ctattattta tcgcacctac gttcaatatt 180
acaggcgaac atacttacta aagtgtgtta attaattaat gcttgtagga cataataata 240
acaattgaat gtctgcacag ccactttcca cacagacatc ataacaaaaa atttccacca 300
aaccccccct cccccgcttc tggccacagc acttaaacac atctctgcca aaccccaaaa 360
acaaagaacc ctaacaccag cctaaccaga tttcaaattt tatcttttgg cggtatgcac 420
ttttaacagt caccccccaa ctaacacatt attttcccct cccactccca tactactaat 480
ctcatcaata caacccccgc ccatcctacc cagcacacac acaccgctgc taaccccata 540
ccccgaacca accaaacccc aaagacaccc cccacagttt atgtagctta cctcctcaaa 600
gcaatacact gaaaatgttt agacgggctc acatcacccc ataaacaaat aggtttggtc 660
ctagcctttc tattagctct tagtaagatt acacatgcaa gcatccccgt tccagtgagt 720
tcaccctcta aatcaccacg atcaaaaggg acaagcatca agcacgcagc aatgcagctc 780
aaaacgctta gcctagccac acccccacgg gaaacagcag tgattaacct ttagcaataa 840
acgaaagttt aactaagcta tactaacccc agggttggtc aatttcgtgc cagccaccgc 900
ggtcacacga ttaacccaag tcaatagaag ccggcgtaaa gagtgtttta gatcaccccc 960
tccccaataa agctaaaact cacctgagtt gtaaaaaact ccagttgaca caaaatagac 1020
tacgaaagtg gctttaacat atctgaacac acaatagcta agacccaaac tgggattaga 1080
taccccacta tgcttagccc taaacctcaa cagttaaatc aacaaaactg ctcgccagaa 1140
cactacgagc cacagcttaa aactcaaagg acctggcggt gcttcatatc cctctagagg 1200
agcctgttct gtaatcgata aaccccgatc aacctcacca cctcttgctc agcctatata 1260
ccgccatctt cagcaaaccc tgatgaaggc tacaaagtaa gcgcaagtac ccacgtaaag 1320
acgttaggtc aaggtgtagc ccatgaggtg gcaagaaatg ggctacattt tctaccccag 1380

-continued

```
aaaactacga tagcccttat gaaacttaag ggtcgaaggt ggatttagca gtaaactaag   1440
agtagagtgc ttagttgaac agggccctga agcgcgtaca caccgcccgt caccctcctc   1500
aagtatactt caaaggacat ttaactaaaa cccctacgca tttatataga ggagacaagt   1560
cgtaacatgg taagtgtact ggaaagtgca cttggacgaa ccagagtgta gcttaacaca   1620
aagcacccaa cttacactta ggagatttca acttaacttg accgctctga gctaaaccta   1680
gccccaaacc cactccacct tactaccaga caaccttagc caaaccattt acccaaataa   1740
agtataggcg atagaaattg aaacctggcg caatagatat agtaccgcaa gggaaagatg   1800
aaaaattata accaagcata atatagcaag gactaacccc tataccttct gcataatgaa   1860
ttaactagaa ataactttgc aaggagagcc aaagctaaga cccccgaaac cagacgagct   1920
acctaagaac agctaaaaga gcacacccgt ctatgtagca aaatagtggg aagatttata   1980
ggtagaggcg acaaacctac cgagcctggt gatagctggt tgtccaagat agaatcttag   2040
ttcaacttta aatttgccca cagaaccctc taaatcccct tgtaaattta actgttagtc   2100
caaagaggaa cagctctttg gacactagga aaaaaccttg tagagagagt aaaaaattta   2160
acacccatag taggcctaaa agcagccacc aattaagaaa gcgttcaagc tcaacaccca   2220
ctacctaaaa aatcccaaac atataactga actcctcaca cccaattgga ccaatctatc   2280
accctataga agaactaatg ttagtataag taacatgaaa acattctcct ccgcataagc   2340
ctgcgtcaga ttaaaacact gaactgacaa ttaacagccc aatatctaca atcaaccaac   2400
aagtcattat taccctcact gtcaacccaa cacaggcatg ctcataagga aaggttaaaa   2460
aaagtaaaag gaactcggca aatcttaccc cgcctgttta ccaaaaacat cacctctagc   2520
atcaccagta ttagaggcac cgcctgccca gtgacacatg tttaacggcc gcggtaccct   2580
aaccgtgcaa aggtagcata atcacttgtt ccttaaatag ggacctgtat gaatggctcc   2640
acgagggttc agctgtctct tacttttaac cagtgaaatt gacctgcccg tgaagaggcg   2700
ggcataacac agcaagacga gaagacccta tggagcttta atttattaat gcaaacagta   2760
cctaacaaac ccacaggtcc taaactacca aacctgcatt aaaaatttcg gttggggcga   2820
cctcggagca gaacccaacc tccgagcagt acatgctaag acttcaccag tcaaagcgaa   2880
ctactatact caattgatcc aataacttga ccaacggaac aagttaccct agggataaca   2940
gcgcaatcct attctagagt ccatatcaac aatagggttt acgacctcga tgttggatca   3000
ggacatcccg atggtgcagc cgctattaaa ggttcgtttg ttcaacgatt aaagtcctac   3060
gtgatctgag ttcagaccgg agtaatccag gtcggtttct atctacttca aattcctccc   3120
tgtacgaaag gacaagagaa ataaggccta cttcacaaag cgccttcccc cgtaaatgat   3180
atcatctcaa cttagtatta tacccacacc cacccaagaa cagggtttgt taagatggca   3240
gagcccggta atcgcataaa acttaaaact ttacagtcag aggttcaatt cctcttctta   3300
acaacatacc catggccaac ctcctactcc tcattgtacc cattctaatc gcaatggcat   3360
tcctaatgct taccgaacga aaaattctag gctatataca actacgcaaa ggccccaacg   3420
ttgtaggccc ctacgggcta ctacaaccct tcgctgacgc cataaaactc ttcaccaaag   3480
agcccctaaa acccgccaca tctaccatca ccctctacat caccgccccg accttagctc   3540
tcaccatcgc tcttctacta tgaacccccc tccccatacc caaccccctg gtcaacctca   3600
acctaggcct cctatttatt ctagccacct ctagcctagc cgtttactca atcctctgat   3660
cagggtgagc atcaaactca aactacgccc tgatcggcgc actgcgagca gtagcccaaa   3720
caatctcata tgaagtcacc ctagccatca ttctactatc aacattacta ataagtggct   3780
```

```
ccctttaacct ctccaccctt atcacaacac aagaacacct ctgattactc ctgccatcat   3840
gaccccttggc cataatatga tttatctcca cactagcaga gaccaaccga accccccttcg   3900
accttgccga aggggagtcc gaactagtct caggcttcaa catcgaatac gccgcaggcc   3960
ccttcgccct attcttcata gccgaataca caaacattat tataataaac accctcacca   4020
ctacaatctt cctaggaaca acatatgacg cactctcccc tgaactctac acaacatatt   4080
ttgtcaccaa gaccctactt ctaacctccc tgttcttatg aattcgaaca gcataccccc   4140
gattccgcta cgaccaactc atacacctcc tatgaaaaaa cttcctacca ctcaccctag   4200
cattacttat atgatatgtc tccataccca ttacaatctc cagcattccc cctcaaacct   4260
aagaaatatg tctgataaaa gagttacttt gatagagtaa ataataggag cttaaacccc   4320
cttatttcta ggactatgag aatcgaaccc atccctgaga atccaaaatt ctccgtgcca   4380
cctatcacac cccatcctaa agtaaggtca gctaaataag ctatcgggcc cataccccga   4440
aaatgttggt tatacccttc ccgtactaat taatcccctg gcccaacccg tcatctactc   4500
taccatcttt gcaggcacac tcatcacagc gctaagctcg cactgatttt ttacctgagt   4560
aggcctagaa ataaacatgc tagcttttat tccagttcta accaaaaaaa taaaccctcg   4620
ttccacagaa gctgccatca agtatttcct cacgcaagca accgcatcca taatccttct   4680
aatagctatc ctcttcaaca atatactctc cggacaatga accataacca atactaccaa   4740
tcaatactca tcattaataa tcataatagc tatagcaata aaactaggaa tagccccctt   4800
tcacttctga gtcccagagg ttacccaagg cacccctctg acatccggcc tgcttcttct   4860
cacatgacaa aaactagccc ccatctcaat catataccaa atctctccct cactaaacgt   4920
aagccttctc ctcactctct caatcttatc catcatagca ggcagttgag gtggattaaa   4980
ccaaacccag ctacgcaaaa tcttagcata ctcctcaatt acccacatag gatgaataat   5040
agcagttcta ccgtacaacc ctaacataac cattcttaat ttaactattt atattatcct   5100
aactactacc gcattcctac tactcaactt aaactccagc accacgaccc tactactatc   5160
tcgcacctga aacaagctaa catgactaac acccttaatt ccatccaccc tcctctccct   5220
aggaggcctg cccccgctaa ccggcttttt gcccaaatgg gccattatcg aagaattcac   5280
aaaaaacaat agcctcatca tccccaccat catagccacc atcaccctcc ttaacctcta   5340
cttctaccta cgcctaatct actccacctc aatcacacta ctccccatat ctaacaacgt   5400
aaaaataaaa tgacagtttg aacatacaaa acccaccccca ttcctcccca cactcatcgc   5460
ccttaccacg ctactcctac ctatctcccc ttttatacta ataatcttat agaaatttag   5520
gttaaataca gaccaagagc cttcaaagcc ctcagtaagt tgcaatactt aatttctgta   5580
acagctaagg actgcaaaac cccactctgc atcaactgaa cgcaaatcag ccactttaat   5640
taagctaagc ccttactaga ccaatgggac ttaaacccac aaacacttag ttaacagcta   5700
agcaccctaa tcaactggct tcaatctact tctcccgccg ccgggaaaaa aggcgggaga   5760
agccccggca ggtttgaagc tgcttcttcg aatttgcaat tcaatatgaa aatcacctcg   5820
gagctggtaa aaagaggcct aacccctgtc tttagattta cagtccaatg cttcactcag   5880
ccattttacc tcacccccac tgatgttcgc cgaccgttga ctattctcta caaaccacaa   5940
agacattgga acactatacc tattattcgg cgcatgagct ggagtcctag gcacagctct   6000
aagcctcctt attcgagccg agctgggcca gccaggcaac cttctaggta acgaccacat   6060
ctacaacgtt atcgtcacag cccatgcatt tgtaataatc ttcttcatag taatacccat   6120
cataatcgga ggctttggca actgactagt tcccctaata atcggtgccc ccgatatggc   6180
```

-continued

```
gtttccccgc ataaacaaca taagcttctg actcttacct ccctctctcc tactcctgct   6240
cgcatctgct atagtggagg ccggagcagg aacaggttga acagtctacc ctcccttagc   6300
agggaactac tcccaccctg gagcctccgt agacctaacc atcttctcct tacacctagc   6360
aggtgtctcc tctatcttag gggccatcaa tttcatcaca acaattatca atataaaacc   6420
ccctgccata acccaatacc aaacgcccct cttcgtctga tccgtcctaa tcacagcagt   6480
cctacttctc ctatctctcc cagtcctagc tgctggcatc actatactac taacagaccg   6540
caacctcaac accaccttct tcgaccccgc cggaggagga gaccccattc tataccaaca   6600
cctattctga tttttcggtc accctgaagt ttatattctt atcctaccag gcttcggaat   6660
aatctcccat attgtaactt actactccgg aaaaaaagaa ccatttggat acataggtat   6720
ggtctgagct atgatatcaa ttggcttcct agggtttatc gtgtgagcac accatatatt   6780
tacagtagga atagacgtag acacacgagc atatttcacc tccgctacca taatcatcgc   6840
tatccccacc ggcgtcaaag tatttagctg actcgccaca ctccacggaa gcaatatgaa   6900
atgatctgct gcagtgctct gagccctagg attcatcttt cttttcaccg taggtggcct   6960
gactggcatt gtattagcaa actcatcact agacatcgta ctacacgaca cgtactacgt   7020
tgtagcccac ttccactatg tcctatcaat aggagctgta tttgccatca taggaggctt   7080
cattcactga tttcccctat tctcaggcta caccctagac caaacctacg ccaaaatcca   7140
tttcactatc atattcatcg gcgtaaatct aactttcttc ccacaacact ttctcggcct   7200
atccggaatg ccccgacgtt actcggacta ccccgatgca tacaccacat gaaacatcct   7260
atcatctgta ggctcattca tttctctaac agcagtaata ttaataattt tcatgatttg   7320
agaagccttc gcttcgaagc gaaaagtcct aatagtagaa gaaccctcca taaacctgga   7380
gtgactatat ggatgccccc caccctacca cacattcgaa gaacccgtat acataaaatc   7440
tagacaaaaa aggaaggaat cgaacccccc aaagctggtt tcaagccaac cccatggcct   7500
ccatgacttt ttcaaaaagg tattagaaaa accatttcat aactttgtca aagttaaatt   7560
ataggctaaa tcctatatat cttaatggca catgcagcgc aagtaggtct acaagacgct   7620
acttccccta tcatagaaga gcttatcacc tttcatgatc acgccctcat aatcattttc   7680
cttatctgct tcctagtcct gtatgccctt ttcctaacac tcacaacaaa actaactaat   7740
actaacatct cagacgctca ggaaatagaa accgtctgaa ctatcctgcc cgccatcatc   7800
ctagtcctca tcgccctccc atccctacgc atcctttaca taacagacga ggtcaacgat   7860
ccctccctta ccatcaaatc aattggccac caatggtact gaacctacga gtacaccgac   7920
tacggcggac taatcttcaa ctcctacata cttcccccat tattcctaga accaggcgac   7980
ctgcgactcc ttgacgttga caatcgagta gtactcccga ttgaagcccc cattcgtata   8040
ataattacat cacaagacgt cttgcactca tgagctgtcc ccacattagg cttaaaaaca   8100
gatgcaattc ccggacgtct aaaccaaacc actttcaccg ctacacgacc gggggtatac   8160
tacggtcaat gctctgaaat ctgtggagca aaccacagtt tcatgcccat cgtcctagaa   8220
ttaattcccc taaaaatctt tgaaataggg cccgtattta ccctatagca ccccctctac   8280
cccctctaga gcccactgta aagctaactt agcattaacc ttttaagtta aagattaaga   8340
gaaccaacac ctctttacag tgaaatgccc caactaaata ctaccgtatg gcccaccata   8400
attacccca tactccttac actattcctc atcacccaac taaaaatatt aaacacaaac   8460
taccacctac ctccctcacc aaagcccata aaaataaaaa attataacaa accctgagaa   8520
ccaaaatgaa cgaaaatctg ttcgcttcat tcattgcccc cacaatccta ggcctacccg   8580
```

```
ccgcagtact gatcattcta tttccccctc tattgatccc cacctccaaa tatctcatca   8640

acaaccgact aatcaccacc caacaatgac taatcaaact aacctcaaaa caaatgataa   8700

ccatacacaa cactaaagga cgaacctgat ctcttatact agtatcctta atcattttta   8760

ttgccacaac taacctcctc ggactcctgc ctcactcatt tacaccaacc acccaactat   8820

ctataaacct agccatggcc atccccttat gagcgggcac agtgattata ggctttcgct   8880

ctaagattaa aaatgcccta gcccacttct taccacaagg cacacctaca ccccttatcc   8940

ccatactagt tattatcgaa accatcagcc tactcattca accaatagcc ctggccgtac   9000

gcctaaccgc taacattact gcaggccacc tactcatgca cctaattgga agcgccaccc   9060

tagcaatatc aaccattaac cttccctcta cacttatcat cttcacaatt ctaattctac   9120

tgactatcct agaaatcgct gtcgccttaa tccaagccta cgttttcaca cttctagtaa   9180

gcctctacct gcacgacaac acataatgac ccaccaatca catgcctatc atatagtaaa   9240

acccagccca tgacccctaa caggggccct ctcagccctc ctaatgacct ccggcctagc   9300

catgtgattt cacttccact ccataacgct cctcatacta ggcctactaa ccaacacact   9360

aaccatatac caatgatggc gcgatgtaac acgagaaagc acataccaag gccaccacac   9420

accacctgtc caaaaaggcc ttcgatacgg gataatccta tttattacct cagaagtttt   9480

tttcttcgca ggatttttct gagcctttta ccactccagc ctagccccta cccccaatt   9540

aggagggcac tggcccccaa caggcatcac cccgctaaat cccctagaag tcccactcct   9600

aaacacatcc gtattactcg catcaggagt atcaatcacc tgagctcacc atagtctaat   9660

agaaaacaac cgaaaccaaa taattcaagc actgcttatt acaattttac tgggtctcta   9720

ttttaccctc ctacaagcct cagagtactt cgagtctccc ttcaccattt ccgacggcat   9780

ctacggctca acatttttttg tagccacagg cttccacgga cttcacgtca ttattggctc   9840

aactttcctc actatctgct tcatccgcca actaatattt cactttacat ccaaacatca   9900

ctttggcttc gaagccgccg cctgatactg gcattttgta gatgtggttt gactatttct   9960

gtatgtctcc atctattgat gagggtctta ctcttttagt ataaatagta ccgttaactt  10020

ccaattaact agttttgaca acattcaaaa aagagtaata aacttcgcct taattttaat  10080

aatcaacacc ctcctagcct tactactaat aattattaca ttttgactac cacaactcaa  10140

cggctacata gaaaaatcca ccccttacga gtgcggcttc gaccctatat cccccgcccg  10200

cgtccctttc tccataaaat tcttcttagt agctattacc ttcttattat ttgatctaga  10260

aattgccctc cttttacccc taccatgagc cctacaaaca actaacctgc cactaatagt  10320

tatgtcatcc ctcttattaa tcatcatcct agccctaagt ctggcctatg agtgactaca  10380

aaaaggatta gactgaaccg aattggtata tagtttaaac aaaacgaatg atttcgactc  10440

attaaattat gataatcata tttaccaaat gcccctcatt tacataaata ttatactagc  10500

atttaccatc tcacttctag gaatactagt atatcgctca cacctcatat cctccctact  10560

atgcctagaa ggaataatac tatcgctgtt cattatagct actctcataa ccctcaacac  10620

ccactccctc ttagccaata ttgtgcctat tgccatacta gtctttgccg cctgcgaagc  10680

agcggtgggc ctagccctac tagtctcaat ctccaacaca tatggcctag actacgtaca  10740

taacctaaac ctactccaat gctaaaacta atcgtcccaa caattatatt actaccactg  10800

acatgacttt ccaaaaaaca cataatttga atcaacacaa ccacccacag cctaattatt  10860

agcatcatcc ctctactatt ttttaaccaa atcaacaaca acctatttag ctgttcccca  10920

accttttcct ccgacccct aacaaccccc ctcctaatac taactacctg actcctaccc  10980
```

-continued

```
ctcacaatca tggcaagcca acgccactta tccagtgaac cactatcacg aaaaaaactc  11040
tacctctcta tactaatctc cctacaaatc tccttaatta taacattcac agccacagaa  11100
ctaatcatat tttatatctt cttcgaaacc acacttatcc ccaccttggc tatcatcacc  11160
cgatgaggca accagccaga acgcctgaac gcaggcacat acttcctatt ctacacccta  11220
gtaggctccc ttcccctact catcgcacta atttacactc acaacaccct aggctcacta  11280
aacattctac tactcactct cactgcccaa gaactatcaa actcctgagc caacaactta  11340
atatgactag cttacacaat agcttttata gtaaagatac ctctttacgg actccactta  11400
tgactcccta aagcccatgt cgaagccccc atcgctgggt caatagtact tgccgcagta  11460
ctcttaaaac taggcggcta tggtataata cgcctcacac tcattctcaa ccccctgaca  11520
aaacacatag cctacccctt ccttgtacta tccctatgag gcataattat aacaagctcc  11580
atctgcctac gacaaacaga cctaaaatcg ctcattgcat actcttcaat cagccacata  11640
gccctcgtag taacagccat tctcatccaa accccctgaa gcttcaccgg cgcagtcatt  11700
ctcataatcg cccacgggct tacatcctca ttactattct gcctagcaaa ctcaaactac  11760
gaacgcactc acagtcgcat cataatcctc tctcaaggac ttcaaactct actcccacta  11820
atagcttttt gatgacttct agcaagcctc gctaacctcg ccttaccccc cactattaac  11880
ctactgggag aactctctgt gctagtaacc acgttctcct gatcaaatat cactctccta  11940
cttacaggac tcaacatact agtcacagcc ctatactccc tctacatatt taccacaaca  12000
caatggggct cactcaccca ccacattaac aacataaaac cctcattcac acgagaaaac  12060
accctcatgt tcatacacct atcccccatt ctcctcctat ccctcaaccc cgacatcatt  12120
accgggtttt cctcttgtaa atatagttta accaaaacat cagattgtga atctgacaac  12180
agaggcttac gaccccttat ttaccgagaa agctcacaag aactgctaac tcatgccccc  12240
atgtctaaca acatggcttt ctcaactttt aaaggataac agctatccat tggtcttagg  12300
ccccaaaaat tttggtgcaa ctccaaataa aagtaataac catgcacact actataacca  12360
ccctaaccct gacttcccta attcccccca tccttaccac cctcgttaac cctaacaaaa  12420
aaaactcata cccccattat gtaaaatcca ttgtcgcatc cacctttatt atcagtctct  12480
tccccacaac aatattcatg tgcctagacc aagaagttat tatctcgaac tgacactgag  12540
ccacaaccca aacaacccag ctctccctaa gcttcaaact agactacttc tccataatat  12600
tcatccctgt agcattgttc gttacatggt ccatcataga attctcactg tgatatataa  12660
actcagaccc aaacattaat cagttcttca aatatctact catcttccta attaccatac  12720
taatcttagt taccgctaac aacctattcc aactgttcat cggctgagag ggcgtaggaa  12780
ttatatcctt cttgctcatc agttgatgat acgcccgagc agatgccaac acagcagcca  12840
ttcaagcaat cctatacaac cgtatcggcg atatcggttt catcctcgcc ttagcatgat  12900
ttatcctaca ctccaactca tgagacccac aacaaatagc ccttctaaac gctaatccaa  12960
gcctcacccc actactaggc ctcctcctag cagcagcagg caaatcagcc caattaggtc  13020
tccacccctg actcccctca gccatagaag gccccacccc agtctcagcc ctactccact  13080
caagcactat agttgtagca ggaatcttct tactcatccg cttccacccc ctagcagaaa  13140
atagcccact aatccaaact ctaacactat gcttaggcgc tatcaccact ctgttcgcag  13200
cagtctgcgc ccttacacaa aatgacatca aaaaaatcgt agccttctcc acttcaagtc  13260
aactaggact cataatagtt acaatcggca tcaaccaacc acacctagca ttcctgcaca  13320
tctgtaccca cgccttcttc aaagccatac tatttatgtg ctccgggtcc atcatccaca  13380
```

-continued

```
accttaacaa tgaacaagat attcgaaaaa taggaggact actcaaaacc atacctctca  13440
cttcaacctc cctcaccatt ggcagcctag cattagcagg aatacctttc ctcacaggtt  13500
tctactccaa agaccacatc atcgaaaccg caaacatatc atacacaaac gcctgagccc  13560
tatctattac tctcatcgct acctccctga caagcgccta tagcactcga ataattcttc  13620
tcaccctaac aggtcaacct cgcttcccca cccttactaa cattaacgaa aataacccca  13680
ccctactaaa ccccattaaa cgcctggcag ccggaagcct attcgcagga tttctcatta  13740
ctaacaacat ttcccccgca tccccccttcc aaacaacaat cccccctctac ctaaaactca  13800
cagccctcgc tgtcactttc ctaggacttc taacagccct agacctcaac tacctaacca  13860
acaaacttaa aataaaatcc ccactatgca cattttattt ctccaacata ctcggattct  13920
accctagcat cacacaccgc acaatcccct atctaggcct tcttacgagc caaaacctgc  13980
ccctactcct cctagaccta acctgactag aaaagctatt acctaaaaca atttcacagc  14040
accaaatctc cacctccatc atcacctcaa cccaaaaagg cataattaaa ctttacttcc  14100
tctctttctt cttcccactc atcctaaccc tactcctaat cacataacct attcccccga  14160
gcaatctcaa ttacaatata tacaccaaca aacaatgttc aaccagtaac tactactaat  14220
caacgcccat aatcatacaa agcccccgca ccaataggat cctcccgaat caaccctgac  14280
ccctctcctt cataaattat tcagcttcct acactattaa agtttaccac aaccaccacc  14340
ccatcatact ctttcaccca cagcaccaat cctacctcca tcgctaaccc cactaaaaca  14400
ctcaccaaga cctcaacccc tgacccccat gcctcaggat actcctcaat agccatcgct  14460
gtagtatatc caaagacaac catcattccc cctaaataaa ttaaaaaaac tattaaaccc  14520
atataacctc cccaaaatt cagaataata acacacccga ccacaccgct aacaatcaat  14580
actaaacccc cataaatagg agaaggctta gaagaaaacc ccacaaaccc cattactaaa  14640
cccacactca acagaaacaa agcatacatc attattctcg cacggactac aaccacgacc  14700
aatgatatga aaaaccatcg ttgtatttca actacaagaa caccaatgac cccaatacgc  14760
aaaactaacc ccctaataaa attaattaac cactcattca tcgacctccc caccccatcc  14820
aacatctccg catgatgaaa cttcggctca ctccttggcg cctgcctgat cctccaaatc  14880
accacaggac tattcctagc catgcactac tcaccagacg cctcaaccgc cttttcatca  14940
atcgcccaca tcactcgaga cgtaaattat ggctgaatca tccgctacct tcacgccaat  15000
ggcgcctcaa tattctttat ctgcctcttc ctacacatcg ggcgaggcct atattacgga  15060
tcatttctct actcagaaac ctgaaacatc ggcattatcc tcctgcttgc aactatagca  15120
acagccttca taggctatgt cctcccgtga ggccaaatat cattctgagg ggccacagta  15180
attacaaact tactatccgc catcccatac attgggacag acctagttca atgaatctga  15240
ggaggctact cagtagacag tcccaccctc acacgattct ttacctttca cttcatcttg  15300
cccttcatta ttgcagccct agcaacactc cacctcctat tcttgcacga aacgggatca  15360
aacaaccccc taggaatcac ctcccattcc gataaaatca ccttccaccc ttactacaca  15420
atcaaagacg ccctcggctt acttctcttc cttctctcct taatgacatt aacactattc  15480
tcaccagacc tcctaggcga cccagacaat tataccctag ccaacccctt aaacacccct  15540
ccccacatca agcccgaatg atatttccta ttcgcctaca caattctccg atccgtccct  15600
aacaaactag gaggcgtcct tgccctatta ctatccatcc tcatcctagc aataatcccc  15660
atcctccata tatccaaaca acaaagcata atatttcgcc cactaagcca atcactttat  15720
tgactcctag ccgcagacct cctcattcta acctgaatcg gaggacaacc agtaagctac  15780
```

-continued

```
ccttttacca tcattggaca agtagcatcc gtactatact tcacaacaat cctaatccta  15840

ataccaacta tctccctaat tgaaaacaaa atactcaaat gggcctgtcc ttgtagtata  15900

aactaataca ccagtcttgt aaaccggaga tgaaaacctt tttccaagga caaatcagag  15960

aaaaagtctt taactccacc attagcaccc aaagctaaga ttctaattta aactattctc  16020

tgttctttca tggggaagca gatttgggta ccacccaagt attgactcac ccatcaacaa  16080

ccgctatgta tttcgtacat tactgccagc caccatgaat attgtacggt accataaata  16140

cttgaccacc tgtagtacat aaaaacccaa tccacatcaa aaccccctcc ccatgcttac  16200

aagcaagtac agcaatcaac cctcaactat cacacatcaa ctgcaactcc aaagccaccc  16260

ctcacccact aggataccaa caaacctacc cacccttaac agtacatagt acataaagcc  16320

atttaccgta catagcacat tacagtcaaa tcccttctcg tccccatgga tgacccccct  16380

cagatagggg tcccttgacc accatcctcc gtgaaatcaa tatcccgcac aagagtgcta  16440

ctctcctcgc tccgggccca taacacttgg gggtagctaa agtgaactgt atccgacatc  16500

tggttcctac ttcagggtca taaagcctaa atagcccaca cgttcccctt aaataagaca  16560

tcacgatg                                                           16568


<210> SEQ ID NO 52
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52

aaaaatttc ccgg                                                        14
```